US009035055B2

(12) United States Patent
Hamano et al.

(10) Patent No.: US 9,035,055 B2
(45) Date of Patent: May 19, 2015

(54) PHOTOELECTRIC CONVERSION MATERIAL, FILM CONTAINING THE MATERIAL, PHOTOELECTRIC CONVERSION DEVICE, PRODUCTION METHOD THEREOF, PHOTOSENSOR, IMAGING DEVICE AND THEIR USE METHODS

(75) Inventors: Mitsumasa Hamano, Kanagawa (JP); Katsuyuki Yofu, Kanagawa (JP); Tetsuro Mitsui, Kanagawa (JP); Kimiatsu Nomura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 757 days.

(21) Appl. No.: 12/877,264

(22) Filed: Sep. 8, 2010

(65) Prior Publication Data

US 2011/0056562 A1 Mar. 10, 2011

(30) Foreign Application Priority Data

Sep. 8, 2009 (JP) ................................ 2009-207230
Mar. 19, 2010 (JP) ................................ 2010-065204

(51) Int. Cl.

| | |
|---|---|
| ***C07D 221/22*** | (2006.01) |
| ***C07C 223/06*** | (2006.01) |
| ***C07C 225/22*** | (2006.01) |
| ***C07D 209/86*** | (2006.01) |
| ***C07D 213/74*** | (2006.01) |
| ***C07D 219/02*** | (2006.01) |
| ***C07D 221/18*** | (2006.01) |
| ***C07D 223/14*** | (2006.01) |
| ***C07D 239/62*** | (2006.01) |
| ***C07D 239/66*** | (2006.01) |
| ***C07D 307/66*** | (2006.01) |
| ***C07D 333/36*** | (2006.01) |
| ***C07D 495/04*** | (2006.01) |
| ***H01L 27/30*** | (2006.01) |
| ***H01L 51/00*** | (2006.01) |
| ***H01L 51/42*** | (2006.01) |
| ***C09B 23/04*** | (2006.01) |
| ***C09B 57/00*** | (2006.01) |

(52) U.S. Cl.
CPC ............ *C07C 223/06* (2013.01); *C07C 225/22* (2013.01); *C07D 209/86* (2013.01); *C07D 213/74* (2013.01); *C07D 219/02* (2013.01); *C07D 221/18* (2013.01); *C07D 223/14* (2013.01); *C07D 239/62* (2013.01); *C07D 239/66* (2013.01); *C07D 307/66* (2013.01); *C07D 333/36* (2013.01); *C07D 495/04* (2013.01); *H01L 27/307* (2013.01); *H01L 51/006* (2013.01); *H01L 51/4253* (2013.01); *C09B 23/04* (2013.01); *C09B 57/008* (2013.01); *C07C 2102/08* (2013.01); *C07C 2103/14* (2013.01); *C07C 2103/18* (2013.01); *C07C 2103/24* (2013.01); *C07C 2103/26* (2013.01); *C07C 2103/50* (2013.01); *Y02E 10/549* (2013.01)

(58) Field of Classification Search
CPC ............. C07C 225/22; C07C 2102/08; C07C 2102/10
USPC ........................................................ 546/61
See application file for complete search history.

(56) References Cited

U.S. PATENT DOCUMENTS

| | | | | |
|---|---|---|---|---|
| 5,965,875 | A | 10/1999 | Merrill | |
| 8,410,356 | B2 | 4/2013 | Kawasaki et al. | |
| 2004/0086748 | A1 | 5/2004 | Nii et al. | |
| 2006/0071253 | A1 | 4/2006 | Nii | |
| 2006/0147750 | A1 | 7/2006 | Ujiie et al. | |
| 2008/0220286 | A1 | 9/2008 | Qiu et al. | |
| 2008/0296564 | A1* | 12/2008 | Nishimura et al. | 257/40 |
| 2009/0179551 | A1 | 7/2009 | Kwon et al. | |
| 2009/0184235 | A1 | 7/2009 | Nomura et al. | |
| 2010/0263726 | A1 | 10/2010 | Kawasaki et al. | |
| 2010/0308312 | A1* | 12/2010 | Mitsui | 257/40 |
| 2012/0080585 | A1 | 4/2012 | Fukuzaki et al. | |

FOREIGN PATENT DOCUMENTS

| | | | |
|---|---|---|---|
| CN | 1827732 | A | 9/2006 |
| CN | 101313047 | A | 11/2008 |
| CN | 101867018 | A | 10/2010 |
| CN | 102460760 | A | 5/2012 |

(Continued)

OTHER PUBLICATIONS

G. Bordeau et al. "Trinaphthylamines as Robust Organic Materials for Two-Photon-Induced Fluorescence"; Journal of American Chemical Society; 2008; vol. 130; No. 50; p. 16836-16837.

Japanese Office Action "Notification of Reasons for Refusal" dated Nov. 9, 2010; Japanese Application No. 2010-200508 with English translation.

The first Office Action issued by the State Intellectual Property Office of People's Republic of China on Nov. 25, 2013, which corresponds to Chinese Patent Application No. 201010278958.9 and is related to U.S. Appl. No. 12/877,264; with English translation.

(Continued)

*Primary Examiner* — Wenwen Cai
(74) *Attorney, Agent, or Firm* — Studebaker & Brackett PC

(57) ABSTRACT

An organic compound and a photoelectric conversion device containing the organic compound are disclosed. The organic compound and device realize high photoelectric conversion efficiency, low dark current and high-speed responsivity. It has been found that when this organic compound and an n-type semiconductor are used in combination, high-speed responsivity can be realized while maintaining high heat resistance, an aspect of which has not been seen when the connection part between a donor part and an acceptor part is a phenylene group.

27 Claims, 2 Drawing Sheets

(56) References Cited

FOREIGN PATENT DOCUMENTS

| | | | |
|---|---|---|---|
| EP | 2242124 | A2 | 10/2010 |
| EP | 2439803 | A1 | 4/2012 |
| JP | 2001-031961 | A | 2/2001 |
| JP | 2002-076391 | A | 3/2002 |
| JP | 2003-332551 | A | 11/2003 |
| JP | 2006-100508 | A | 4/2006 |
| JP | 2006-124333 | A | 5/2006 |
| JP | 2007-123707 | A | 5/2007 |
| JP | 2008-247887 | A | 10/2008 |
| JP | 2009-9931 | A | 1/2009 |
| JP | 2009-516680 | A | 4/2009 |
| JP | 2009-167348 | A | 7/2009 |
| JP | 2010-103457 | A | 5/2010 |
| JP | 2010-168511 | A | 8/2010 |
| JP | 2010-251180 | A | 11/2010 |
| TW | 200844210 | A | 11/2008 |
| WO | 2007/061218 | A1 | 5/2007 |
| WO | 2010/140645 | A1 | 12/2010 |

OTHER PUBLICATIONS

"Preliminary Notice of First Office Action," issued by the Taiwanese The extended European search report issued on Oct. 2, 2013, which corresponds to EP10175757.3 and is related to U.S. Appl. No. 12/877,264.

The second Office Action issued by the State Intellectual Property Office of People's Republic of China on Aug. 6, 2014, which corresponds to Chinese Patent Application No. 201010278958.9 and is related to U.S. Appl. No. 12/877,264; with English translation.

The extended European search report issued by the European Patent Office on Sep. 10, 2014, which corresponds to European Patent Application No. 14174939.0-1454 and is related to U.S. Appl. No. 12/877,264. Patent Office on Aug. 13, 2014, which corresponds to Taiwanese Patent Application No. 99130377 and is related to U.S. Appl. No. 12/877,264; with English language translation.

An Office Action; "Communication pursuant to Article 94(3) EPC," issued by the European Patent Office on Sep. 5, 2014, which corresponds to European Patent Application No. 10 175 757.3-1454 and is related to U.S. Appl. No. 12/877,264.

* cited by examiner

PHOTOELECTRIC CONVERSION MATERIAL, FILM CONTAINING THE MATERIAL, PHOTOELECTRIC CONVERSION DEVICE, PRODUCTION METHOD THEREOF, PHOTOSENSOR, IMAGING DEVICE AND THEIR USE METHODS

BACKGROUND OF THE INVENTION

1. Field of the Invention

The present invention relates to a novel compound useful as a photoelectric conversion device material, a film containing the material, a photoelectric conversion device, a production method thereof, a photosensor, an imaging device and their use methods.

2. Description of the Related Art

Conventional photosensors in general are a device fabricated by forming a photodiode (PD) in a semiconductor substrate such as silicon (Si). As for the solid-state imaging device, there is widely used a flat solid-state imaging device where PD are two-dimensionally arrayed in a semiconductor substrate and a signal according to a signal charge generated by photoelectric conversion in each PD is read out through a CCD or CMOS circuit.

The method for realizing a color solid-state imaging device is generally fabrication of a structure where on the light incident surface side of the flat solid-state imaging device, a color filter transmitting only light at a specific wavelength is disposed for color separation. In particular, a single-plate solid-state imaging device in which color filters transmitting blue (B) light, green (G) light and red (R) light, respectively, are regularly disposed on each of two-dimensionally arrayed PD is well known as a system widely used at present in a digital camera and the like.

In this single-plate solid-state imaging device, since the color filter transmits only light at a limited wavelength, light failed in transmitting through the color filter is not utilized and the light utilization efficiency is bad. Also, in recent years, fabrication of a multipixel device is proceeding, and the pixel size and in turn, the area of a photodiode part become small, which brings about problems of reduction in the aperture ratio and reduction in the light collection efficiency.

In order to solve these problems, a system of stacking, in the longitudinal direction, photoelectric conversion parts capable of detecting light at different wavelengths has been proposed. As regards such a system, in so far as visible light is concerned, there are disclosed, for example, a system utilizing wavelength dependency of the absorption coefficient of Si, where a vertical stack structure is formed and colors are separated by the difference in the depth (Patent Document 1), and a system where a first light-receiving part using an organic semiconductor and second and third light-receiving parts each composed of Si are formed (Patent Document 2).

However, such a system is disadvantageous in that the color separation is poor, because the absorption range is overlapped among respective portions in the depth direction of Si and the spectroscopic property is bad. As for other methods to solve the problems, a structure where a photoelectric conversion film by amorphous silicon or an organic photoelectric conversion film is formed on a signal reading substrate, is known as a technique for increasing the aperture ratio.

Also, several examples are known for a photoelectric conversion device, an imaging device, a photosensor and a solar cell each using an organic photoelectric conversion film. The photoelectric conversion device using an organic photoelectric conversion film faces the task in particular of increasing the photoelectric conversion efficiency and decreasing the dark current, and as a method for improving these, there are disclosed, for example, introduction of a pn-junction or introduction of a bulk heterojunction structure for the former and introduction of a blocking layer for the latter.

In an attempt to increase the photoelectric conversion efficiency by the introduction of pn-junction or bulk heterojunction structure, an increase in the dark current often becomes a problem. Also, the degree of improvement in the photoelectric conversion efficiency differs depending on the combination of materials and in some cases, the ratio of photosignal amount/dark time noise does not increase from that before introduction of the structure above. In the case of employing the method above, what materials are combined is important and in particular, when reduction in the dark time noise is intended, this is difficult to achieve by conventionally reported combinations of materials.

Furthermore, the kind of the material used and the film structure are not only one of main factors for the photoelectric conversion efficiency (exciton dissociation efficiency, charge transport performance) and dark current (e.g., amount of dark time carrier) but also a governing factor for the signal responsivity, though this is scarcely mentioned in past reports. In use as a solid-state imaging device, all of high photoelectric conversion efficiency, low dark current and high response speed need to be satisfied, but there has not been specifically disclosed what an organic photoelectric conversion material or a device structure satisfies this requirement.

A photoelectric conversion film containing fullerenes is described in Patent Document 3, but only by fullerenes, it is impossible to satisfy all of the above-described high photoelectric conversion efficiency, low dark current and high response speed. Also, a solar cell using a bulk heterojunction film by a plurality of organic semiconductors, with at least one organic semiconductor being a crystal grain, is described in Patent Document 4, where, however, disclosure on the dark current and high-speed response is not found and application or the like to a photoelectric conversion device for imaging devices is neither described nor suggested.

In addition, conventional photoelectric conversion materials when heated sometimes cause sensitivity reduction or increase of the dark current and have room for more improvement in view of heat resistance.

[Patent Document 1] U.S. Pat. No. 5,965,875

[Patent Document 2] JP-A-2003-332551 (the term "JP-A" as used herein means an "unexamined published Japanese patent application")

[Patent Document 3] JP-A-2007-123707

[Patent Document 4] JP-A-2002-076391

SUMMARY OF THE INVENTION

An object of the present invention is to provide a photoelectric conversion device and a solid-state imaging device, in which sufficiently high sensitivity and high heat resistance are obtained and high-speed responsivity is exhibited.

In an organic photoelectric conversion device, for realizing high photoelectric conversion efficiency, low dark current and high-speed responsivity, the organic photoelectric conversion film used preferably satisfies the following requirements.

1. In terms of high efficiency and high-speed response, the signal charge after dissociation of an exciton needs to be swiftly transmitted to both electrodes without loss. High mobility and high charge transportability with a small number of carrier trapping sites are necessary.

2. In terms of high photoelectric conversion efficiency, it is preferred that the exciton stabilizing energy is small and the exciton can be swiftly dissociated by the effect of an externally applied electric field or an electric field generated in the inside by pn-junction or the like (high exciton dissociation efficiency).

3. In order to reduce as much the carrier generated in the inside at dark time as possible, it is preferred to select a film structure or material that allows little presence of an intermediate level in the inside or impurities working out to one of causes thereof.

4. In the case of stacking a plurality of layers, an energy level matching the adjacent layer is required and if an energetic barrier is formed, this inhibits charge transport.

Furthermore, in view of the application to a production process having a heating step such as placement of a color filter, laying of a protective film and soldering of a device or with consideration for the enhancement of storability, the material for the photoelectric conversion device and the film containing the material are required to have high heat resistance.

In the case of forming the organic photoelectric conversion film by a vapor deposition method, the decomposition temperature is preferably higher than the temperature allowing for vapor deposition, because the thermal decomposition during vapor deposition can be suppressed. The coating method is advantageous in that the film can be formed without subjecting to limitation by the decomposition above and a low cost can be realized, but film formation by a vapor deposition method is preferred because uniform film formation is easy and possible mixing of impurities can be reduced.

The present inventors have made intensive studies, as a result, the following selection and combination of materials have been found as techniques ensuring that the requirements above are satisfied and high photoelectric conversion efficiency, low dark current, high-speed responsivity and heat resistance can be realized.

According to the studies by the present inventors, it has been found that a compound containing, as the donor part, a triarylamine moiety with a substituent or a triheteroarylamine moiety, where the connection part between the donor part and the acceptor part is a naphthylene group, is a novel compound useful as a photoelectric conversion material.

Furthermore, it has been found that when this novel compound and an n-type semiconductor (preferably fullerenes) are used in combination, high-speed responsivity can be realized while maintaining high heat resistance, an aspect of which has not been seen when the connection part between the donor part and the acceptor part is a phenylene group. The present invention has been accomplished based on these findings.

The above-described object can be attained by the following techniques.

(1) A compound represented by the following formula (I):

Formula (I):

(I)

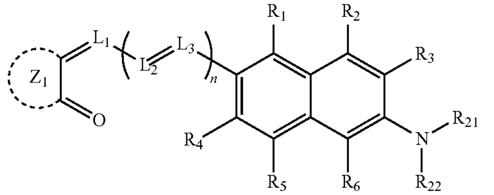

wherein $Z_1$ is a ring containing two carbon atoms and represents a 5-membered ring, a 6-membered ring or a condensed ring containing at least either a 5-membered ring or a 6-membered ring, each of $L_1$, $L_2$ and $L_3$ independently represents an unsubstituted methine group or a substituted methine group, n represents an integer of 0 or more, each of $R_1$, $R_2$, $R_3$, $R_4$, $R_5$ and $R_6$ independently represents a hydrogen atom or a substituent, $R_1$ and $R_2$, $R_2$ and $R_3$, $R_4$ and $R_5$, or $R_5$ and $R_6$ may be combined with each other to form a ring, and each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded.

(2) The compound according to the above (1), wherein said compound represented by formula (I) is a compound represented by the following formula (II):

Formula (II):

(II)

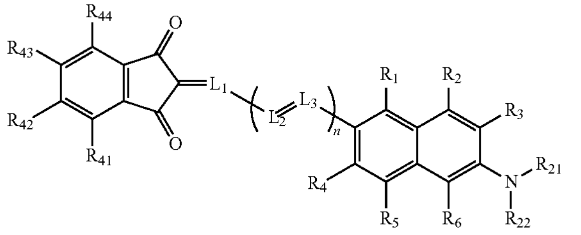

wherein $L_1$, $L_2$, $L_3$, n, $R_1$, $R_2$, $R_3$, $R_4$, $R_5$, $R_6$, $R_{21}$ and $R_{22}$ have the same meanings as those in formula (I), and each of $R_{41}$, $R_{42}$, $R_{43}$ and $R_{44}$ independently represents a hydrogen atom or a substituent.

(3) The compound according to the above (1), wherein said compound represented by formula (I) is a compound represented by the following formula (III):

Formula (III):

(III)

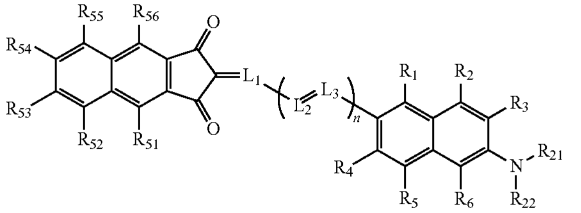

wherein $L_1$, $L_2$, $L_3$, n, $R_1$, $R_2$, $R_3$, $R_4$, $R_5$, $R_6$, $R_{21}$ and $R_{22}$ have the same meanings as these in formula (I), and each of $R_{51}$, $R_{52}$, $R_{53}$, $R_{54}$, $R_{55}$ and $R_{56}$ independently represents a hydrogen atom or a substituent.

(4) The compound according to the above (1), wherein said compound represented by formula (I) is a compound represented by the following formula (IV):

Formula (IV):

(IV)

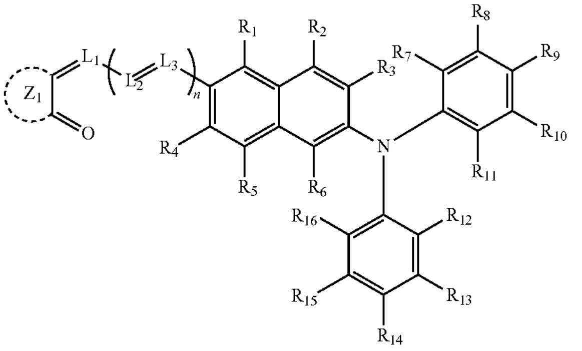

wherein $Z_1$, $L_1$, $L_2$, $L_3$, n, $R_1$, $R_2$, $R_3$, $R_4$, $R_5$ and $R_6$ have the same meanings as those in formula (I), each of $R_7$ to $R_{11}$ and $R_{12}$ to $R_{16}$ independently represents a hydrogen atom or a substituent, provided that a case where all of $R_7$ to $R_{11}$ and $R_{12}$ to $R_{16}$ are a hydrogen atom is excluded, adjacent members out of $R_7$ to $R_{11}$ and out of $R_{12}$ to $R_{16}$ may be combined with each other to form a ring, and each of the pair $R_3$ and $R_7$ and the pair $R_6$ and $R_{16}$ may be connected.

(5) The compound according to the above (2), wherein, wherein each of $R_{41}$ to $R_{44}$ in formula (II) independently is a hydrogen atom, a halogen atom, an alkyl group, an aryl group, a heterocyclic group, an alkoxy group, an aryloxy group, an amino group, an alkylthio group, an alkenyl group or a cyano group.

(6) The compound according to the above (3), wherein, wherein each of $R_{51}$ to $R_{56}$ in formula (III) independently is a hydrogen atom, a halogen atom, an alkyl group, an aryl group, a heterocyclic group, an alkoxy group, an aryloxy group, an amino group, an alkylthio group, an alkenyl group or a cyano group.

(7) The compound according to the above (4), wherein, wherein each of $R_7$ to $R_{11}$ and $R_{12}$ to $R_{16}$ in formula (IV) independently is a hydrogen atom, a halogen atom, an alkyl group, an aryl group, a heterocyclic group, a hydroxyl group, a nitro group, an alkoxy group, an aryloxy group, a heterocyclic oxy group, an amino group, an alkylthio group, an arylthio group, an alkenyl group, a cyano group or a heterocyclic thio group.

(8) The compound according to any one of the above (1) to (7), wherein, wherein each of $R_1$ to $R_6$ in formulae (I) to (IV) independently is a hydrogen atom, an alkyl group, an aryl group, a heterocyclic group, an alkoxy group or an aryloxy group.

(9) The compound according to any one of the above (1) to (8), wherein in formulae (I) to (IV), each of $L_1$, $L_2$ and $L_3$ is an unsubstituted methine group.

(10) The compound according to any one of the above (1) to (9), wherein in formulae (I) to (IV), n is 0.

(11) A compound represented by the following formula (V):

Formula (V):

(V)

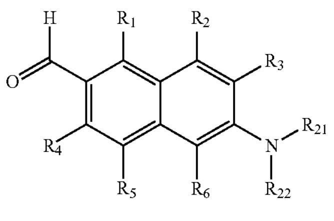

wherein each of $R_1$, $R_2$, $R_3$, $R_4$, $R_5$ and $R_6$ independently represents a hydrogen atom or a substituent, $R_1$ and $R_2$, $R_2$ and $R_3$, $R_4$ and $R_5$, or $R_5$ and $R_6$ may be combined with each other to form a ring, and each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded.

(12) A photoelectric conversion material containing the compound according to any one of the above (1) to (10).

(13) A film containing the compound according to any one of the above (1) to (10).

(14) The film according to the above (13), which further comprises an n-type organic semiconductor.

(15) The film according to the above (14), wherein the film is a non-luminescent film.

(16) A photoelectric conversion device comprising an electrically conductive film, an organic photoelectric conversion film, and a transparent electrically conductive film, wherein said organic photoelectric conversion film contains the compound according to any one of claims the above (1) to (10).

(17) The photoelectric conversion device according to the above (16), wherein said organic photoelectric conversion film contains an n-type organic semiconductor.

(18) The photoelectric conversion device according to the above (17), wherein the organic photoelectric conversion film is a non-luminescent film.

(19) The photoelectric conversion device according to the above (17) or (18), wherein said n-type organic semiconductor is a fullerene or a fullerene derivative.

(20) The photoelectric conversion device according to the above (19), wherein said fullerene is $C_{60}$.

(21) The photoelectric conversion device according to the above (19) or (20), wherein said organic photoelectric conversion film has a bulk heterojunction structure formed in a state of the compound according to any one of the above (1) to (10) and said fullerene or fullerene derivative being mixed.

(22) The photoelectric conversion device according to any one of the above (19) to (21), wherein the ratio between the compound represented by formula (I) according to the above (1) and said fullerene or fullerene derivative (said fullerene or fullerene derivative/the compound represented by formula (I)×100(%)), which are contained in said organic photoelectric conversion film, is 50% (volume ratio) or more.

(23) The photoelectric conversion device according to any one of the above (16) to (22), wherein said photoelectric conversion device is fabricated by stacking said electrically conductive film, said organic photoelectric conversion film and said transparent electrically conductive film in this order.

(24) The photoelectric conversion device according to any one of the above (16) to (23), wherein said organic photoelectric conversion film is deposited by a vacuum deposition method.

(25) The photoelectric conversion device according to any one of the above (16) to (24), wherein light is incident on said organic photoelectric conversion film through said transparent electrically conductive film.

(26) The photoelectric conversion device according to any one of the above (16) to (25), wherein said transparent electrically conductive film comprises a transparent electrically conductive metal oxide.

(27) The photoelectric conversion device according to any one of the above (16) to (26), wherein the transparent electrically conductive film is formed directly on said organic photoelectric conversion film.

(28) The photoelectric conversion device according to any one of the above (16) to (27), which further comprises a charge blocking layer.

(29) The photoelectric conversion device according to any one of the above (16) to (28), wherein the absorption spectrum (in a chloroform solution) of said compound represented by formula (I) has a molar extinction coefficient of 30,000 $M^{-1}$ $cm^{-1}$ or more in the visible region at a wavelength of 400 to 700 nm

(30) A use method of the photoelectric conversion device according to any one of the above (16) to (29), with said electrically conductive film and said transparent electrically conductive film defining a pair of electrodes, the method comprising a step of applying an electric field of $1\times10^{-4}$ to $1\times10^{7}$ V/cm between said pair of electrodes.

(31) A method for producing the photoelectric conversion device according to any one of the above (16) to (29), comprising a step of co-depositing said compound represented by formula (I) and fullerene or fullerene derivative by vacuum heating deposition.

(32) A photosensor comprising the photoelectric conversion device according to any one of the above (16) to (29).

(33) An imaging device containing the photoelectric conversion device according to any one of the above (16) to (29).

According to the present invention, a photoelectric conversion device and an imaging device, each having sufficiently high sensitivity, high heat resistance and high-speed responsivity, can be provided.

DESCRIPTION OF REFERENCE NUMERALS AND SIGNS

10*a*, 10*b* Photoelectric conversion device
11 Lower electrode (electrically conductive film)
12 Photoelectric conversion layer (photoelectric conversion film)
15 Upper electrode (transparent electrically conductive film)
16A Electron blocking layer
16B Hole blocking layer
100 Imaging Device

DETAILED DESCRIPTION OF THE INVENTION

[Photoelectric Conversion Device]

The photoelectric conversion device of the present invention is a photoelectric conversion device comprising an electrically conductive film, an organic photoelectric conversion film, and a transparent electrically conductive film, wherein the organic photoelectric conversion film contains a compound represented by formula (I). In a preferred mode, the electrically conductive film, the organic photoelectric conversion film and the transparent electrically conductive film are stacked in this order. The organic photoelectric conversion film contains at least a photoelectric conversion layer and may additionally contain a charge blocking layer (an electron blocking layer, a hole blocking layer).

Figure 1A:
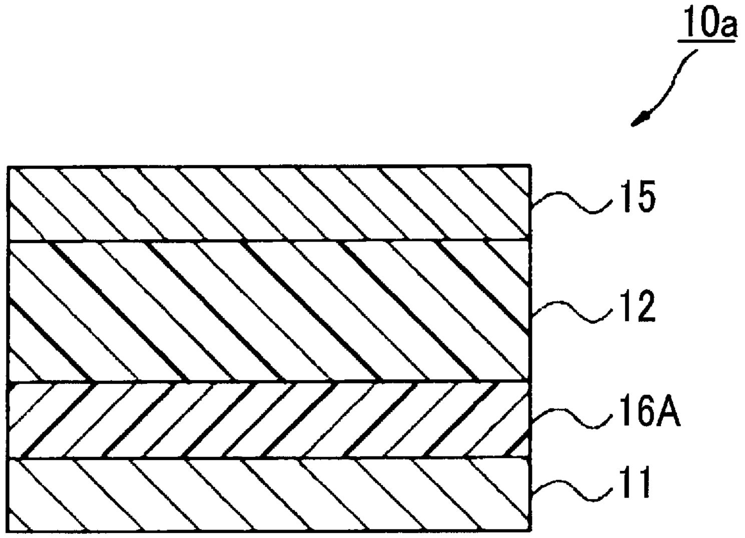
FIG. 1A and FIG. 1B each is a schematic cross-sectional view showing one configuration example of the photoelectric conversion device.
Figure 1B:
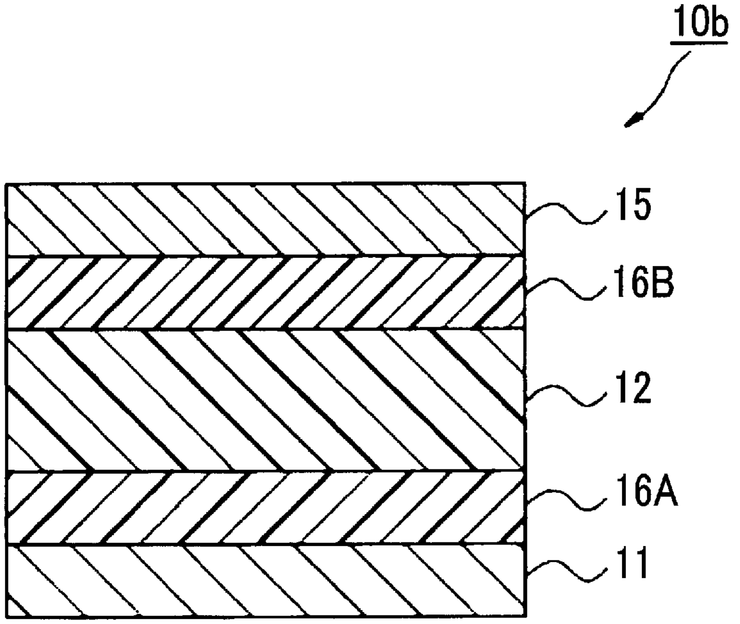

FIG. 1A and FIG. 1B show a configuration example of the photoelectric conversion device according to an embodiment of the present invention.

The photoelectric conversion device 10*a* shown in FIG. 1A has a configuration where an electron blocking layer 16A formed on a lower electrode 11, a photoelectric conversion layer 12 formed on the electron blocking layer 16A, and a transparent electrically conductive film (hereinafter referred to as an upper electrode) 15 functioning as an upper electrode are stacked in this order on an electrically conductive film (hereinafter referred to as a lower electrode) 11 functioning as a lower electrode.

FIG. 1B shows another configuration example of the photoelectric conversion device. The photoelectric conversion device 10*b* shown in FIG. 1B has a configuration where an electron blocking layer 16A, a photoelectric conversion layer 12, a hole blocking layer 16B and an upper electrode 15 are stacked in this order on a lower electrode 11. Incidentally, in FIG. 1A and FIG. 1B, the order of stacking an electron blocking layer, a photoelectric conversion layer and a hole blocking layer may be reversed according to usage or properties.

In such a configuration, light is preferably incident on the organic photoelectric conversion film through the transparent electrically conductive film.

Also, in using such a photoelectric conversion device, an electric field can be applied. In this case, the electrically conductive film and the transparent electrically conductive film define a pair of electrodes, and an electric field of, for example, $1\times10^{-4}$ to $1\times10^{7}$ V/cm can be applied between the pair of electrodes.

The present invention also relates to a use method of the photoelectric conversion device, with the electrically conductive film and the transparent electrically conductive film defining a pair of electrodes, the method comprising a step of applying an electric field of $1\times10^{-4}$ to $1\times10^{7}$ V/cm between the pair of electrodes.

Furthermore, the present invention relates to a production method of a photoelectric conversion device, comprising a step of co-depositing the compound represented by formula (I) and the later-described fullerene or fullerene derivative by vacuum heating deposition.

The elements constituting the photoelectric conversion device according to this embodiment are described below.

(Electrode)

Each of the electrodes (the upper electrode (transparent electrically conductive film) 15 and the lower electrode (electrically conductive film) 11) is composed of an electrically conductive material. Examples of the electrically conductive material which can be used include a metal, an alloy, a metal oxide, an electroconductive compound, and a mixture thereof.

Light is incident from the upper electrode 15 and therefore, the upper electrode 15 needs to be sufficiently transparent to light that is to be detected. Specific examples thereof include an electrically conductive metal oxide such as tin oxide doped with antimony or fluorine (ATO, FTO), tin oxide, zinc oxide, indium oxide, indium tin oxide (ITO) and indium zinc oxide (IZO); a metal thin film such as gold, silver, chromium and nickel; a mixture or laminate of such a metal and such an electrically conductive metal oxide; an inorganic electrically conductive substance such as copper iodide and copper sulfide; an organic electrically conductive material such as polyaniline, polythiophene and polypyrrole; and a laminate of such a material and ITO. Among these, an electrically conductive metal oxide is preferred in view of high electrical conductivity, transparency and the like. The transparent electrically conductive film is preferably formed directly on the organic photoelectric conversion film. The upper electrode 15 is deposited on the organic photoelectric conversion layer 12 and therefore, is preferably deposited by a method causing no deterioration of the properties of the organic photoelectric conversion layer 12.

The lower electrode 11 includes, according to usage, a case where transparency is imparted, a case where, conversely, a material capable of reflecting light is used without imparting transparency, and the like. Specific examples thereof include an electrically conductive metal oxide such as tin oxide doped with antimony or fluorine (ATO, FTO), tin oxide, zinc oxide, indium oxide, indium tin oxide (ITO) and indium zinc oxide (IZO); a metal such as gold, silver, chromium, nickel, titanium, tungsten and aluminum; an electrically conductive compound such as oxide and nitride of the metal (for example, titanium nitride (TiN)); a mixture or laminate of such a metal and such an electrically conductive metal oxide; an inorganic electrically conductive substance such as copper iodide and copper sulfide; an organic electrically conductive material such as polyaniline, polythiophene and polypyrrole; and a laminate of such a material and ITO or titanium nitride.

The method for forming the electrode is not particularly limited and may be appropriately selected by taking into consideration the aptitude for the electrode material. Specifically, the electrode can be formed, for example, by a wet system such as printing and coating, a physical system such as vacuum deposition. sputtering and ion plating, or a chemical system such as CVD and plasma CVD.

In the case where the material of the electrode is ITO, the electrode can be formed by a method such as electron beam method, sputtering method, resistance heating deposition method, chemical reaction method (e.g., sol-gel method) and coating of a dispersion of indium tin oxide. The film produced using ITO may be further subjected to, for example, a UV-ozone treatment or a plasma treatment. In the case where the material of the electrode is TiN, various methods including a reactive sputtering method are used, and the film formed can be further subjected to a UV-ozone treatment, a plasma treatment or the like.

The upper electrode 15 is preferably produced in a plasma-free state. When the upper electrode 15 is produced in a plasma-free state, the effect of plasma on the substrate can be reduced and good photoelectric conversion properties can be obtained. Here, the plasma-free state means a state where plasma is not generated during deposition of the upper electrode 15, or a state where the distance from a plasma source to the substrate is 2 cm or more, preferably 10 cm or more, more preferably 20 cm or more, and the amount of plasma reaching the substrate is reduced.

Examples of the apparatus generating no plasma during deposition of the upper electrode 15 include an electron beam deposition apparatus (EB deposition apparatus) and a pulsed laser deposition apparatus. As for the EB deposition apparatus or pulsed laser deposition apparatus, apparatuses described, for example, in Yutaka Sawada (supervisor), *Tomei Doden Maku no Shin Tenkai* (*New Development of Transparent Conductive Film*), CMC (1999), Yutaka Sawada (supervisor), *Tomei Doden Maku no Shin Tenkai II* (*New Development of Transparent Conductive Film II*), CMC (2002), *Tomei Doden Maku no Gijutsu* (*Technology of Transparent Conductive Film*), JSPS, Ohmsha (1999), and references cited therein can be used. In the following, the method of depositing the transparent electrode film by using an EB deposition apparatus is referred to as an EB deposition method, and the method of depositing the transparent electrode film by using a pulsed laser deposition apparatus is referred to as a pulsed laser deposition method.

As for the apparatus capable of realizing a state where the distance from a plasma source to the substrate is 2 cm or more and the amount of plasma reaching the substrate is reduced (hereinafter referred to as a "plasma-free deposition apparatus"), an opposed-target sputtering apparatus, an arc plasma deposition method and the like are considered, and examples of such an apparatuses which can be used include those described in Yutaka Sawada (supervisor), *Tomei Doden Maku no Shin Tenkai* (*New Development of Transparent Conductive Film*), CMC (1999), Yutaka Sawada (supervisor), *Tomei Doden Makuno Shin Tenkai II* (*New Development of Transparent Conductive Film II*), CMC (2002), *Tomei Doden Maku no Gijutsu* (*Technology of Transparent Conductive Film*), JSPS, Ohmsha (1999), and references cited therein.

In the case where the upper electrode 15 is a transparent electrically conductive film such as TCO, a DC short or an increase of leak current sometimes occurs. One of causes thereof is considered because fine cracks introduced into the photoelectric conversion layer 12 are coveraged by a dense film such as TCO to increase the conduction with the first electrode film 11 on the opposite side. Therefore, in the case of an electrode having relatively poor film quality such as A1, the leak current hardly increases. The increase of leak current can be greatly suppressed by controlling the film thickness of the upper electrode 15 with respect to the film thickness (that is, the crack depth) of the photoelectric conversion layer 12. The thickness of the upper electrode 15 is preferably 1/5 or less, more preferably 1/10 or less, of the thickness of the photoelectric conversion layer 12.

Usually, when the thickness of the electrically conductive film is made smaller than a certain range, an abrupt increase of the resistance value is incurred, but in the solid-state imaging device where the photoelectric conversion device according to this embodiment is incorporated, the sheet resistance may be, preferably, from 100 to 10,000 Ω/sq. and the latitude as to in which range the film thickness can be reduced is large. Also, as the thickness of the upper electrode (transparent electrically conductive film) 15 is smaller, the quantity of light absorbed is reduced and the light transmittance is generally increased. The increase of light transmittance brings about an increase of light absorption in the photoelectric conversion layer 12 and an increase of photoelectric conversion performance, and this is very preferred. Considering the suppression of leak current and the increase of resistance value of thin film as well as the increase of transmittance, which are associated with reduction in the film thickness, the thickness of the upper electrode 15 is preferably from 5 to 100 nm, more preferably from 5 to 20 nm (Organic Photoelectric Conversion Film)

The organic photoelectric conversion film contains a compound represented by the following formula (I). It is preferred that the compound represented by the following formula (I) is contained as a photoelectric conversion material in the organic photoelectric conversion layer 12.

Formula (I):

(I)

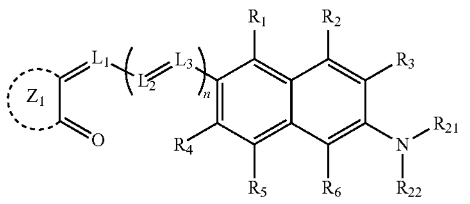

In the formula (I), $Z_1$ is a ring containing two carbon atoms and represents a 5-membered ring, a 6-membered ring or a condensed ring containing at least either a 5-membered ring or a 6-membered ring, each of $L_1$, $L_2$ and $L_3$ independently represents an unsubstituted methine group or a substituted methine group, n represents an integer of 0 or more, each of $R_1$, $R_2$, $R_3$, $R_4$, $R_5$ and $R_6$ independently represents a hydrogen atom or a substituent, $R_1$ and $R_2$, $R_2$ and $R_3$, $R_4$ and $R_5$, or $R_5$ and $R_6$ may combine with each other to form a ring, and each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded.

As described above, a compound where the connection part between the donor part (the portion of —$NR_{21}R_{22}$) and the acceptor part (the portion which is connected to the naphthylene group via $L_1$ to $L_3$) is a naphthylene group is used as a photoelectric conversion material together with fullerenes, whereby a photoelectric conversion device having excellent heat resistance and high-speed responsivity can be obtained. This is considered because thanks to the naphthylene group as the connection part between the donor part and the acceptor part, the interaction with fullerenes is enhanced and the response speed is improved. Also, the compound above has sufficient sensitivity.

In formula (I), each of $L_1$, $L_2$ and $L_3$ independently represents an unsubstituted methine group or a substituted methine group. Substituents in the substituted methine group may be combined with each other to form a ring. The ring includes a 6-membered ring (e.g., benzene ring). Examples of the substituent of the substituted methine group include the substituent W. It is preferred that all of $L_1$, $L_2$ and $L_3$ are an unsubstituted methine group.

n represents an integer of 0 or more, preferably represents an integer of 0 to 3, and is more preferably 0. When n becomes large, the absorption wavelength region is allowed to reside on a long wavelength side, but the thermal decomposition temperature becomes low. From the standpoint of having appropriate absorption in the visible region and suppressing thermal decomposition at the vapor deposition of film, n is preferably 0.

Each of $R_1$ to $R_6$ independently represents a hydrogen atom or a substituent. In the case where each of $R_1$ to $R_6$ represents a substituent, examples of the substituent represented by $R_1$ to $R_6$ include the later-described substituent W, and especially, a halogen atom, an alkyl group, an aryl group, a heterocyclic group, a hydroxyl group, a nitro group, an alkoxy group, an aryloxy group, a hetero ring oxy group, an amino group, an alkylthio group, an arylthio group, an alkenyl group, a cyano group, a hetero ring thio group are preferable.

Each of $R_1$ to $R_6$ is independently, preferably a hydrogen atom, a halogen atom, an alkyl group, an aryl group, a heterocyclic group, a hydroxyl group, a nitro group, an alkoxy group, an aryloxy group, a heterocyclic oxy group, an amino group, an alkylthio group, an arylthio group, an alkenyl group, a cyano group or a heterocyclic thio group, more preferably a hydrogen atom, an alkyl group, an aryl group, and a heterocyclic group, an alkoxy group, an aryloxy group, further more preferably a hydrogen atom, an alkyl group having a carbon number of 1 to 20, an aryl group having a carbon number of 6 to 20, or a heterocyclic group having a carbon number of 4 to 16, an alkoxy group having a carbon number of 1 to 20, an aryloxy group having a carbon number of 6 to 20, more preferably a hydrogen atom, an alkyl group having a carbon number of 1 to 12, or an aryl group having a carbon number of 6 to 14, an alkoxy group having a carbon number of 1 to 12, an aryloxy group, having a carbon number of 6 to 10, still more preferably a hydrogen atom, an alkyl group having a carbon number of 1 to 6, or an aryl group having a carbon number of 6 to 10, yet still more preferably a hydrogen atom. The alkyl group may be branched. Also, in the case where each of $R_1$ to $R_6$ is a substituent, it may have a further substituent. Examples of the further substituent include the later-described W.

Specific preferred examples of $R_1$ to $R_6$ include a hydrogen atom, a methyl group, an ethyl group, a propyl group, a butyl group, a hexyl group, a cyclohexyl group, a phenyl group and a naphthyl group.

$R_1$ and $R_2$, $R_2$ and $R_3$, $R_4$ and $R_5$, or $R_5$ and $R_6$ may be combined with each other to form a ring.

Examples of the ring formed include the later-described ring R. Among these, preferred are, for example, a benzene ring, a naphthalene ring, an anthracene ring, a pyridine ring and a pyrimidine ring.

Each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded.

The aryl group represented by $R_{21}$ and $R_{22}$ is preferably an aryl group having a carbon number of 6 to 30, more preferably an aryl group having a carbon number of 6 to 20. Specific examples of the aryl group include a phenyl group, a naphthyl group, a biphenylyl group, a terphenyl group, an anthryl group and a fluorenyl group.

The substituent of the substituted aryl group in $R_{21}$ and $R_{22}$ is preferably an alkyl group (e.g., methyl, ethyl, tert-butyl), an alkoxy group (e.g., methoxy, ethoxy, isopropoxy), an aryl group (e.g., phenyl, naphthyl, phenanthryl, anthryl) or a heteroaryl group (e.g., thienyl, furanyl, pyridyl, carbazolyl).

The aryl group or substituted aryl group represented by $R_{21}$ and $R_{22}$ is preferably a phenyl group, a substituted phenyl group, a biphenyl group, a naphthyl group, a phenanthryl group, an anthryl group, a fluorenyl group or a substituted fluorenyl group (preferably a 9,9'-dialkyl-2-fluorenyl group).

In the case where each of $R_{21}$ and $R_{22}$ is a heteroaryl group, the heteroaryl group is preferably a heteroaryl group composed of a 5-, 6- or 7-membered ring or a condensed ring thereof. Examples of the heteroatom contained in the heteroaryl group include an oxygen atom, a sulfur atom and a nitrogen atom. Specific examples of the ring constituting the heteroaryl group include a furan ring, a thiophene ring, a pyrrole ring, a pyrroline ring, a pyrrolidine ring, an oxazole ring, an isoxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazane ring, a tetrazole ring, a pyrane ring, a thiine ring, a pyridine ring, a piperidine ring, an oxazine ring, a morpholine ring, a thiazine ring, a pyridazine ring, a pyrimidine ring, a pyrazine ring, a piperazine ring and a triazine ring.

Examples of the condensed ring include a benzofuran ring, an isobenzofuran ring, a benzothiophene ring, an indole ring, an indoline ring, an isoindole ring, a benzoxazole ring, a benzothiazole ring, an indazole ring, a benzimidazole ring, a quinoline ring, an isoquinoline ring, a cinnoline ring, a phthalazine ring, a quinazoline ring, a quinoxaline ring, a dibenzofuran ring, a carbazole ring, a xanthene ring, an acridine ring, a phenanthridine ring, a phenanthroline ring, a phenazine ring, a phenoxazine ring, a thianthrene ring, a thienothiophene ring, an indolizine ring, a quinolidine ring, a quinuclidine ring, a naphthylidine ring, a purine ring and a pteridine ring.

The substituent of the substituted heteroaryl group in $R_{21}$ and $R_{22}$ is preferably an alkyl group (e.g., methyl, ethyl, tert-butyl), an alkoxy group (e.g., methoxy, ethoxy, isopropoxy), an aryl group (e.g., phenyl, naphthyl, phenanthryl, anthryl) or a heteroaryl group (e.g., thienyl, furanyl, pyridyl, carbazolyl).

The ring constituting the heteroaryl group or substituted heteroaryl group represented by $R_{21}$ and $R_{22}$ is preferably a thiophene ring, a substituted thiophene ring, a furan ring, a substituted furan ring, a thienothiophene ring, a substituted thienothiophene ring or a carbazolyl group.

Each of $R_{21}$ and $R_{22}$ is independently, preferably a phenyl group, a naphthyl group, a fluorenyl group, a biphenyl group, an anthracenyl group or a phenanthrenyl group, more preferably a phenyl group, a naphthyl group or a fluorenyl group. In the case where each of $R_{21}$ and $R_{22}$ has a substituent, the substituent is preferably an alkyl group, an alkyl halide group, an alkoxy group, an aryl group or a heteroaryl group, more preferably a methyl group, an isopropyl group, a tert-butyl group, a trifluoromethyl group, a phenyl group or a carbazolyl group.

$Z_1$ is a ring containing two carbon atoms and represents a 5-membered ring, a 6-membered ring or a condensed ring containing at least either a 5-membered ring or a 6-membered ring. The ring is preferably a ring which is usually used as an acidic nucleus in a merocyanine dye, and specific examples thereof include the followings:

(a) a 1,3-dicarbonyl nucleus, such as 1,3-indandione nucleus, 1,3-cyclohexanedione, 5,5-dimethyl-1,3-cyclohexanedione and 1,3-dioxane-4,6-dione, (b) a pyrazolinone nucleus, such as 1-phenyl-2-pyrazolin-5-one, 3-methyl-1-phenyl-2-pyrazolin-5-one and 1-(2-benzothiazoyl)-3-methyl-2-pyrazolin-5-one, (c) an isoxazolinone nucleus, such as 3-phenyl-2-isoxazolin-5-one and 3-methyl-2-isoxazolin-5-one, (d) an oxyindole nucleus, such as 1-alkyl-2,3-dihydro-2-oxyindole, (e) a 2,4,6-triketohexahydropyrimidine nucleus, such as barbituric acid, 2-thiobarbituric acid and a derivative thereof; examples of the derivative include a 1-alkyl form such as 1-methyl and 1-ethyl, a 1,3-dialkyl form such as 1,3-dimethyl, 1,3-diethyl and 1,3-dibutyl, a 1,3-diaryl form such as 1,3-diphenyl, 1,3-di(p-chlorophenyl) and 1,3-di(p-ethoxycarbonylphenyl), a 1-alkyl-1-aryl form such as 1-ethyl-3-phenyl, and a heterocyclic disubstituted form at 1-position and 3-position, such as 1,3-di(2-pyridyl), (f) a 2-thio-2,4-thiazolidinedione nucleus, such as rhodanine and a derivative thereof; examples of the derivative include a 3-alkylrhodanine such as 3-methylrhodanine, 3-ethylrhodanine and 3-allylrhodanine, a 3-arylrhodanine such as 3-phenylrhodanine, and a rhodanine substituted with heterocyclic ring at 3-position, such as 3-(2-pyridyl)rhodanine, (g) a 2-thio-2,4-oxazolidinedione (2-thio-2,4-(3H,5H)-oxazoledione) nucleus, such as 3-ethyl-2-thio-2,4-oxazolidinedione, (h) a thianaphthenone nucleus, such as 3(2H)-thianaphthenone-1,1-dioxide, (i) a 2-thio-2,5-thiazolidinedione nucleus, such as 3-ethyl-2-thio-2,5-thiazolidinedione, (j) a 2,4-thiazolidinedione nucleus, such as 2,4-thiazolidinedione, 3-ethyl-2,4-thiazolidinedione and 3-phenyl-2,4-thiazolidinedione, (k) a thiazolin-4-one nucleus, such as 4-thiazolinone and 2-ethyl-4-thiazolinone, (l) a 2,4-imidazolidinedione (hydantoin) nucleus, such as 2,4-imidazolidinedione and 3-ethyl-2,4-imidazolidinedione, (m) a 2-thio-2,4-imidazolidinedione (2-thiohydantoin) nucleus, such as 2-thio-2,4-imidazolidinedione and 3-ethyl-2-thio-2,4-imidazolidinedione, (n) a 2-imidazolin-5-one nucleus, such as 2-propylmercapto-2-imidazolin-5-one, (o) a 3,5-pyrazolidinedione nucleus, such as 1,2-diphenyl-3,5-pyrazolidinedione and 1,2-dimethyl-3,5-pyrazolidinedione, (p) a benzothiophen-3-one nucleus, such as benzothiophen-3-one, oxobenzothiophen-3-one and dioxobenzothiophen-3-one, and (q) an indanone nucleus, such as 1-indanone, 3-phenyl-1-indanone, 3-methyl-1-indanone, 3,3-diphenyl-1-indanone and 3,3-dimethyl-1-indanone.

The ring represented by $Z_1$ is preferably a 1,3-dicarbonyl nucleus, a pyrazolinone nucleus, a 2,4,6-triketohexahydropyrimidine nucleus (including a thioketone form, such as barbituric acid nucleus and 2-thiobarbituric acid nucleus), a 2-thio-2,4-thiazolidinedione nucleus, a 2-thio-2,4-oxazolidinedione nucleus, a 2-thio-2,5-thiazolidinedione nucleus, a 2,4-thiazolidinedione nucleus, a 2,4-imidazolidinedione nucleus, a 2-thio-2,4-imidazolidinedione nucleus, a 2-imidazolin-5-one nucleus, a 3,5-pyrazolidinedione nucleus, a benzothiophen-3-one nucleus or an indanone nucleus, more preferably a 1,3-dicarbonyl nucleus, a 2,4,6-triketohexahydropyrimidine nucleus (including a thioketone form, such as barbituric acid nucleus and 2-thiobarbituric acid nucleus), a 3,5-pyrazolidinedione nucleus, a benzothiophen-3-one nucleus or an indanone nucleus, still more preferably a 1,3-dicarbonyl nucleus or a 2,4,6-triketohexahydropyrimidine nucleus (including a thioketone form, such as barbituric acid nucleus and 2-thiobarbituric acid nucleus), yet still more preferably a 1,3-indandione nucleus, a barbituric acid nucleus, a 2-thiobarbituric acid nucleus, or a derivative thereof.

The ring represented by $Z_1$ is preferably a ring represented by the following formula:

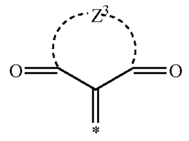

$Z^3$ represents an atomic group necessary for forming a 5- or 6-membered ring. $Z^3$ can be selected from the above-described rings represented by $Z_1$ and is preferably a 1,3-dicarbonyl nucleus or a 2,4,6-triketohexahydropyrimidine nucleus (including a thioketone form), more preferably a 1,3-indandione nucleus, a barbituric acid nucleus, a 2-thiobarbituric acid nucleus or a derivative thereof. * represents the bonding position.

By controlling the interaction between acceptor parts, high hole transportability can be brought out when depositing the film by vapor co-deposition with an n-type semiconductor (e.g., fullerenes). The interaction can be controlled by the structure of the acceptor part and the introduction of a substituent working out to a steric hindrance. In the barbituric acid nucleus and 2-thiobarbituric acid nucleus, both two hydrogens at two N-positions are preferably substituted for by a substituent, whereby the intermolecular interaction can be controlled. Examples of the substituent include the later-described substituent W, and the substituent is preferably an alkyl group, more preferably a methyl group, an ethyl group, a propyl group or a butyl group.

In the case where the ring represented by $Z_1$ is a 1,3-indandione nucleus, a group represented by the following formula (VI) or a group represented by the following formula (VII) is preferred.

Formula (VI):

(VI)

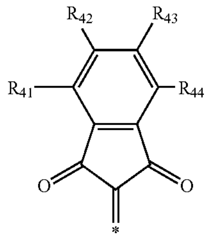

In formula (VI), each of $R_{41}$ to $R_{44}$ independently represents a hydrogen atom or a substituent, and * represents the bonding position;

Formula (VII):

(VII)

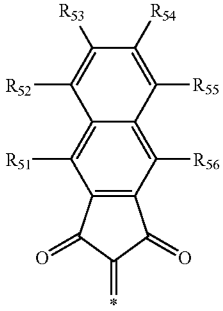

In formula (VII), each of $R_{51}$, $R_{52}$, $R_{53}$, $R_{54}$, $R_{55}$ and $R_{56}$ independently represents a hydrogen atom or a substituent, and * represents the bonding position.

In formulae (VI) and (VII), in the case where each of $R_{41}$ to $R_{44}$ and $R_{51}$ to $R_{56}$ represents a substituent, examples of the substituents represented by each of $R_{41}$ to $R_{44}$ and $R_{51}$ to $R_{56}$, for example, include the later-described substituent W, and especially, a halogen atom, an alkyl group, an aryl group, a heterocyclic group, a hydroxyl group, a nitro group, an alkoxy group, an aryloxy group, a hetero ring oxy group, an amino group, an alkylthio group, an arylthio group, an alkenyl group, a cyano group, a hetero ring thio group are preferable.

Each of $R_{41}$ to $R_{44}$ and $R_{51}$ to $R_{56}$ is independently, preferably a hydrogen atom, a halogen atom, an alkyl group, an aryl group, a heterocyclic group, a hydroxyl group, a nitro group, an alkoxy group, an aryloxy group, a heterocyclic oxy group, an amino group, an alkylthio group, an arylthio group, an alkenyl group, a cyano group or a heterocyclic thio group, more preferably a hydrogen atom, a halogen atom, an alkyl group, an aryl group, a heterocyclic group, an alkoxy group, an aryloxy group, an amino group, an alkylthio group, an alkenyl group, a cyano group, further more preferably a hydrogen atom, a halogen atom, an alkyl group having a carbon number of 1 to 20, an alkenyl group having a carbon number of 2 to 20, an alkoxy group having a carbon number of 1 to 20, an aryl group having a carbon number of 6 to 20, an aryloxy group having a carbon number of 6 to 20 or a heterocyclic group composed of a 5-, 6- or 7-membered ring or a condensed ring thereof, still more preferably a hydrogen atom, an alkyl group having a carbon number of 1 to 12, an alkenyl group having a carbon number of 2 to 12, an alkoxy group having a carbon number of 1 to 12, an aryl group having a carbon number of 6 to 10, an aryloxy group having a carbon number of 6 to 10 or a heterocyclic group composed of a 5- or 6-membered ring or a condensed ring thereof, yet still more preferably a hydrogen atom. In the case where each of $R_{41}$ to $R_{44}$ and $R_{51}$ to $R_{56}$ is a substituent, the substituent may have a further substituent. Examples of the further substituent include the later-described substituent W.

The alkyl group may be linear or branched. Examples of the heteroatom contained in the heterocyclic group include an oxygen atom, a sulfur atom and a nitrogen atom.

Specific examples of the alkyl group, alkenyl group, aryl group and the like include those exemplified in the alkyl group, alkenyl group and aryl group of the later-described substituent W.

Adjacent members out of $R_{41}$ to $R_{44}$ and out of $R_{51}$ to $R_{56}$ may be combined with each other to form a ring. Examples of the ring formed include the later-described ring R. The ring formed is preferably, for example, a benzene ring, a naphthalene ring, an anthracene ring, a pyridine ring, a pyrimidine ring or a pyrazine ring.

In formula (VI), the case where all of $R_{41}$ to $R_{44}$ are a hydrogen atom is preferred. In formula (VII), the case where all of $R_{51}$ to $R_{56}$ are a hydrogen atom is preferred.

In the case where $Z_1$ is a group represented by formula (VI) or a group represented by formula (VII), the compound represented by formula (I) becomes a compound represented by formula (II) or a compound represented by the following formula (III), respectively.

The compound represented by formula (I) is preferably a compound represented by the following formula (II) or a compound represented by the following formula (III):

Formula (II):

(II)

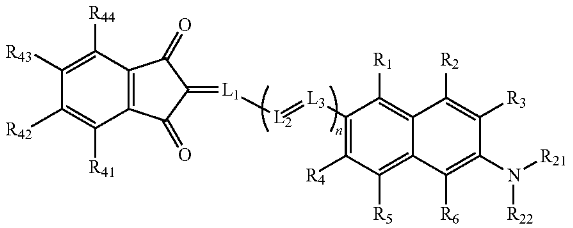

In the formula, $L_1$, $L_2$, $L_3$, n, $R_1$, $R_2$, $R_3$, $R_4$, $R_5$, $R_6$, $R_{21}$ and $R_{22}$ have the same meanings as those in formula (I), and the preferred ranges are also the same. $R_{41}$, $R_{42}$, $R_{43}$ and $R_{44}$ have the same meanings as those in formula (VI), and the preferred ranges are also the same.

Formula (II):

(III)

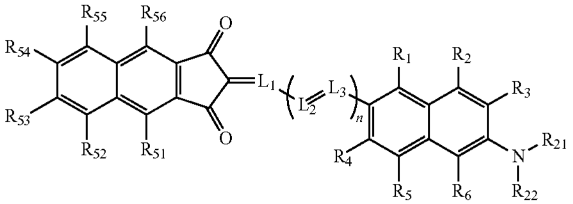

In the formula, $L_1$, $L_2$, $L_3$, n, $R_1$, $R_2$, $R_3$, $R_4$, $R_5$, $R_6$, $R_{21}$ and $R_{22}$ have the same meanings as those in formula (I), and the preferred ranges are also the same. $R_{51}$, $R_{52}$, $R_{53}$, $R_{54}$, $R_{55}$ and $R_{56}$ have the same meanings as those in formula (VII), and the preferred ranges are also the same.

In the case where the ring formed by $Z_1$ of formula (I) is a 2,4,6-triketohexahydropyrimidine nucleus (including a thioketone form), $Z_1$ is preferably a group represented by the following formula (VIII):

Formula (VIII):

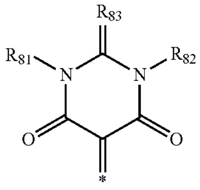

Each of $R_{81}$ and $R_{82}$ independently represents a hydrogen atom or a substituent, $R_{83}$ represents an oxygen atom, a sulfur atom or a substituent, and * represents the bonding position.

In the case of a group represented by formula (VIII), each of $R_{81}$ and $R_{82}$ independently represents a hydrogen atom or a substituent. As to the substituent, for example, those described as the substituent W may be applied. Each of $R_{81}$ and $R_{82}$ is independently, preferably an alkyl group, an aryl group or a heterocyclic group (e.g., 2-pyridyl), more preferably an alkyl group having a carbon number of 1 to 6 (e.g., methyl, ethyl, n-propyl, tert-butyl).

$R_{83}$ represents an oxygen atom, a sulfur atom or a substituent, but $R_{83}$ preferably represents an oxygen atom or a sulfur atom. The substituent is preferably a substituent with the bonding part being a nitrogen atom or a carbon atom. In the case of a nitrogen atom, those substituted with an alkyl group (having a carbon number of 1 to 12) or an aryl group (having a carbon number of 6 to 12) are preferred, and specific examples thereof include a methylamino group, an ethylamino group, a butylamino group, a hexylamino group, a phenylamino group and a naphthylamino group. In the case where the bonding part is a carbon atom, it may be sufficient if at least one electron-withdrawing group is further substituted. The electron-withdrawing group includes a carbonyl group, a cyano group, a sulfoxide group, a sulfonyl group and a phosphoryl group and preferably further has a substituent. Examples of this substituent include the substituent W. The substituent as $R_{83}$ preferably forms a 5- or 6-membered ring containing the carbon atom, and specific examples thereof include those having the following structures.

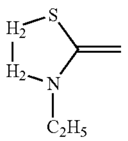
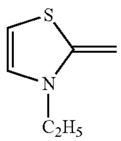
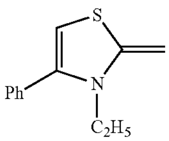
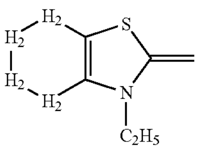
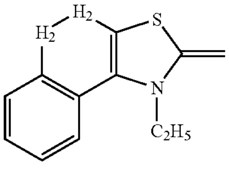

-continued

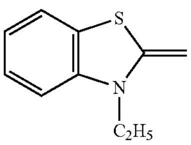
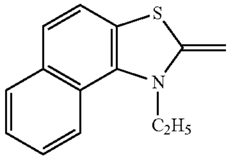
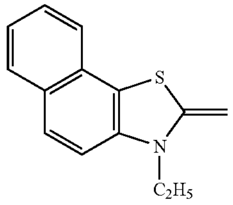
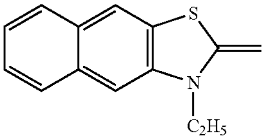
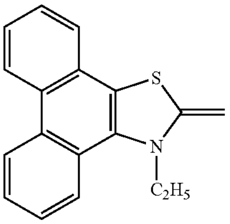
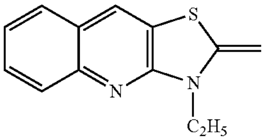
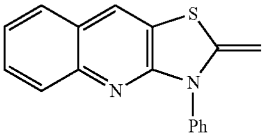
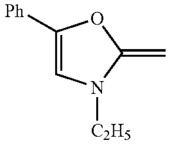
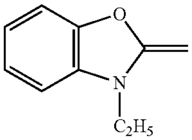
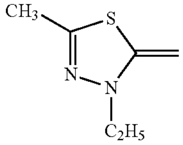
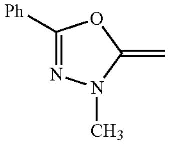
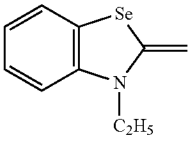
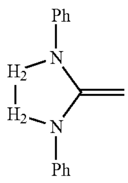
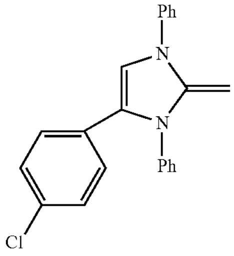
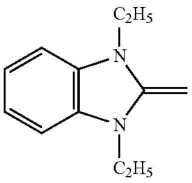
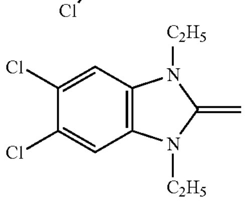
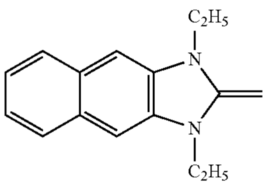
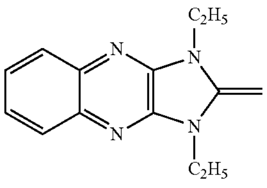
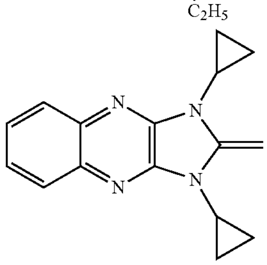

-continued
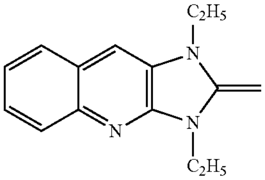
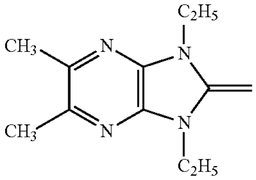
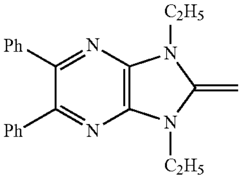
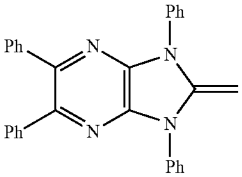
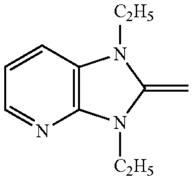
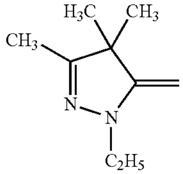
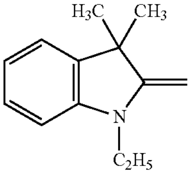
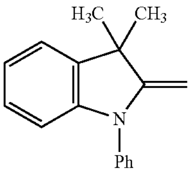
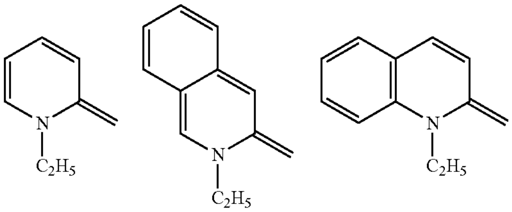
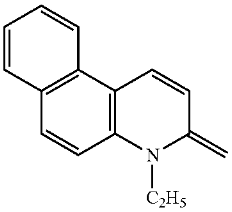
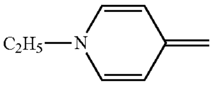
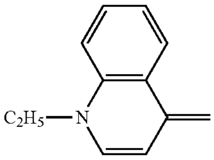
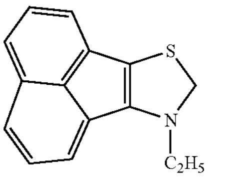
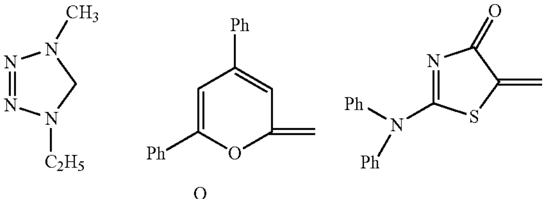
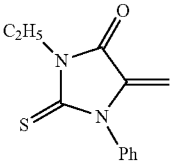
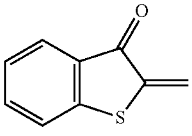
-continued
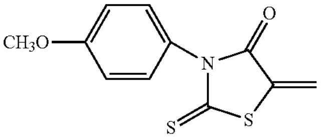
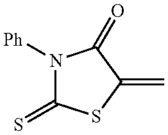
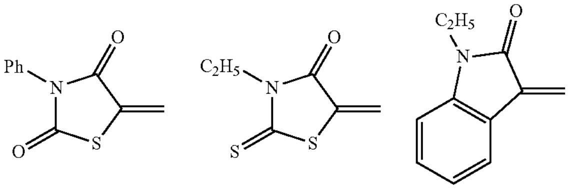
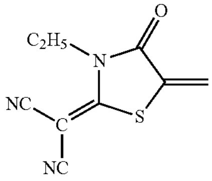
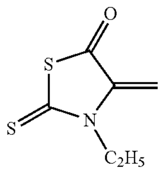
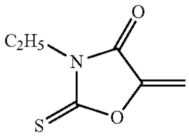
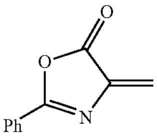
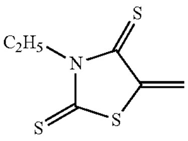
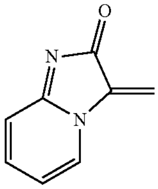
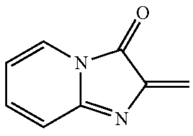
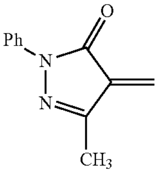
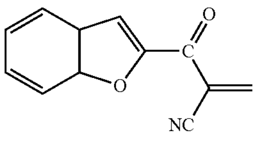
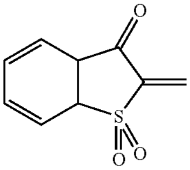
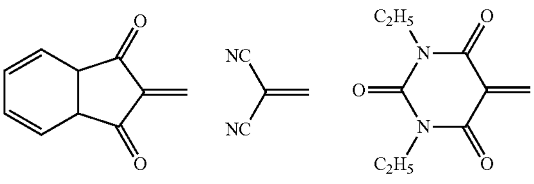
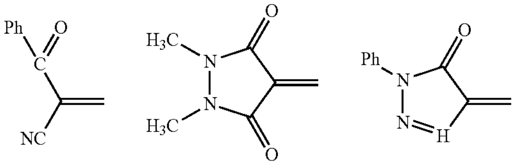
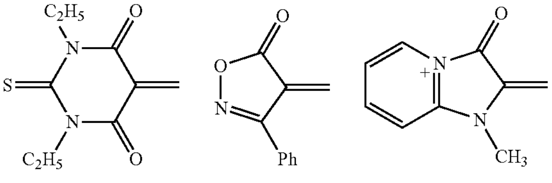

-continued

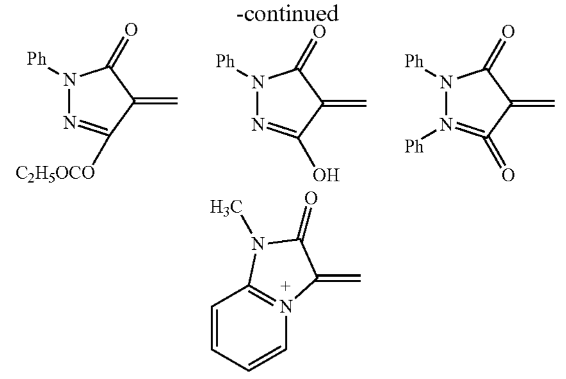

In the groups above, Ph indicates a phenyl group.

The compound represented by formula (I) is preferably a compound represented by the following formula (IV):

Formula (IV):

(IV)

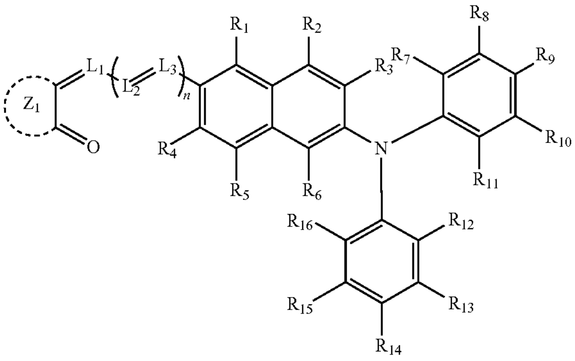

In the formula, $Z_1$, $L_1$, $L_2$, $L_3$, n, $R_1$, $R_2$, $R_3$, $R_4$, $R_5$ and $R_6$ have the same meanings as those in formula (I), and the preferred ranges are also the same.

Each of $R_7$ to $R_{11}$ and $R_{12}$ to $R_{16}$ independently represents a hydrogen atom or a substituent, provided that a case where all of $R_7$ to $R_{11}$ and $R_{12}$ to $R_{16}$ are a hydrogen atom is excluded. Adjacent members out of $R_7$ to $R_{11}$ and out of $R_{12}$ to $R_{16}$ may combine with each other to form a ring. Furthermore, each of the pair $R_3$ and $R_7$ and the pair $R_6$ and $R_{16}$ and the pair $R_{11}$ and $R_{12}$ may connect.

In formula (IV), each of $R_7$ to $R_{11}$ and $R_{12}$ to $R_{16}$ independently represents a hydrogen atom or a substituent. However, it is not allowed that all of $R_7$ to $R_{11}$ and $R_{12}$ to $R_{16}$ are a hydrogen atom. Incidentally, when $R_3$ connects with $R_7$ or $R_6$ connects with $R_{16}$, all other members $R_8$ to $R_{11}$ and $R_{12}$ to $R_{15}$ may be a hydrogen atom. Moreover, when $R_{11}$ connects with $R_{12}$, all other members $R_7$ to $R_{10}$ and $R_{13}$ to $R_{16}$ may be a hydrogen atom.

In the case where each of $R_7$ to $R_{11}$ and $R_{12}$ to $R_{16}$ represents a substituent, examples of the substituent represented by $R_7$ to $R_{11}$ and $R_{12}$ to $R_{16}$ include the later-described substituent W, and especially, a halogen atom, an alkyl group, an aryl group, a heterocyclic group, a hydroxyl group, a nitro group, an alkoxy group, an aryloxy group, a hetero ring oxy group, an amino group, an alkylthio group, an arylthio group, an alkenyl group, a cyano group, a hetero ring thio group are preferable.

Each of $R_7$ to $R_{11}$ and $R_{12}$ to $R_{16}$ is independently preferably a hydrogen atom, a halogen atom, an alkyl group, an aryl group, a heterocyclic group, a hydroxyl group, a nitro group, an alkoxy group, an aryloxy group, a heterocyclic oxy group, an amino group, an alkylthio group, an arylthio group, an alkenyl group, a cyano group or a heterocyclic thio group, more preferably a hydrogen atom, a halogen atom, an alkyl group, an alkenyl group, an alkoxy group, an aryl group, an aryloxy group or a heterocyclic group, more preferably a hydrogen atom, a halogen atom, an alkyl group having a carbon number of 1 to 20, an alkenyl group having a carbon number of 2 to 20, an alkoxy group having a carbon number of 1 to 20, an aryl group having a carbon number of 6 to 20, an aryloxy group having a carbon number of 6 to 20, or a heterocyclic group composed of a 5-, 6- or 7-membered ring or a condensed ring thereof, still more preferably a hydrogen atom, a halogen atom, an alkyl group having a carbon number of 1 to 12, an alkenyl group having a carbon number of 2 to 12, an alkoxy group having a carbon number of 1 to 12, an aryl group having a carbon number of 6 to 10, an aryloxy group having a carbon number of 6 to 10, or a heterocyclic group composed of a 5- or 6-membered ring or a condensed ring thereof.

The alkyl group may be linear or branched. Examples of the heteroatom contained in the heterocyclic group include an oxygen atom, a sulfur atom and a nitrogen atom.

Specific examples of the alkyl group, alkenyl group, aryl group and the like include those exemplified in the alkyl group, alkenyl group and aryl group of the later-described substituent W.

Adjacent members out of $R_7$ to $R_{11}$ and out of $R_{12}$ to $R_{16}$ may combine with each other to form a ring. Examples of the ring formed include the later-described ring R. The ring formed is preferably, for example, a benzene ring, a naphthalene ring, an anthracene ring, a pyridine ring or a pyrimidine ring.

Furthermore, each of the pair $R_3$ and $R_7$ and the pair $R_6$ and $R_{16}$ may be connected. In the case where $R_3$ connects with $R_7$ or $R_6$ connects with $R_{16}$, a condensed ring by four or more rings containing a naphthylene group and a phenyl group results. The connection between $R_3$ and $R_7$ or between $R_6$ and $R_{16}$ may be a single bond.

Specific examples of the compound represented by formula (I) are illustrated below, but the present invention is not limited thereto.

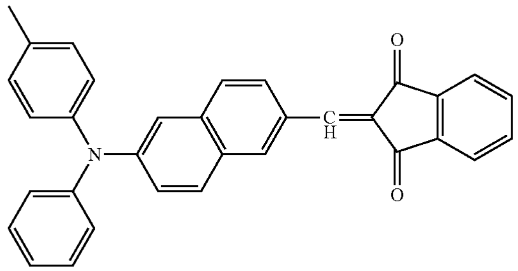

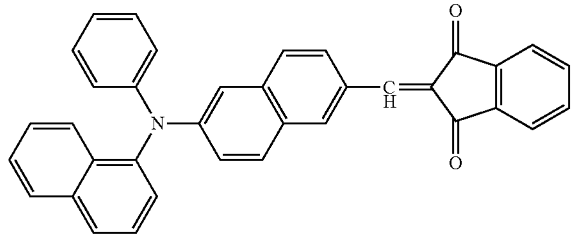

-continued
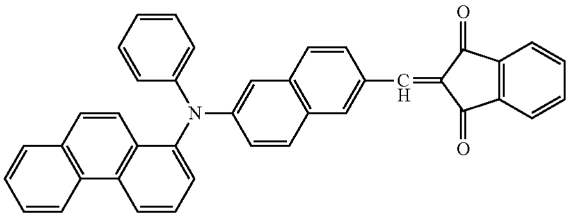
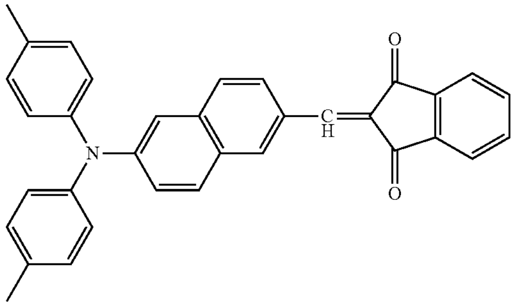
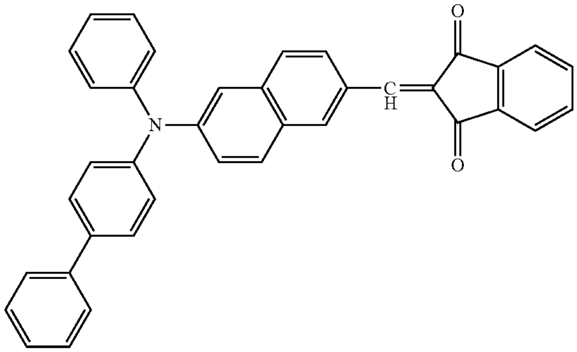
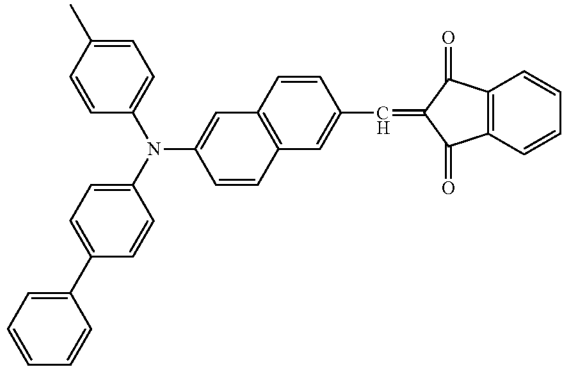
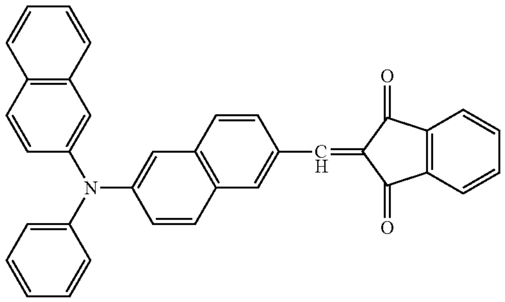
-continued
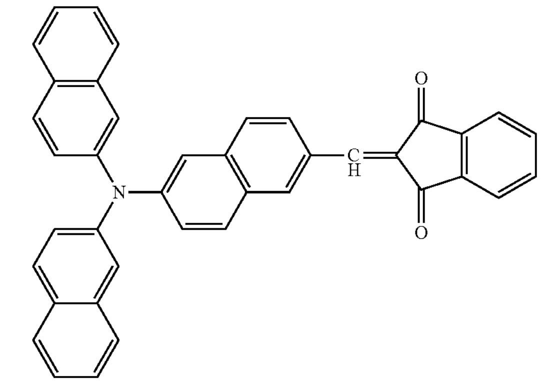
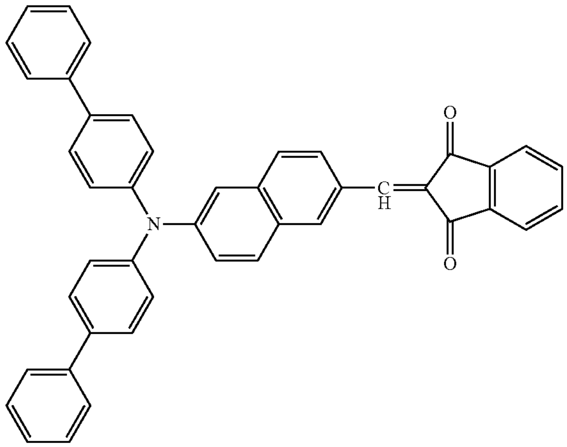
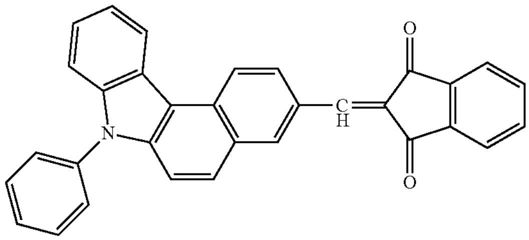
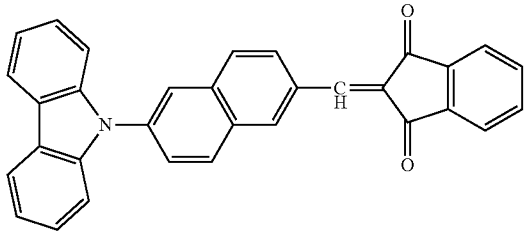
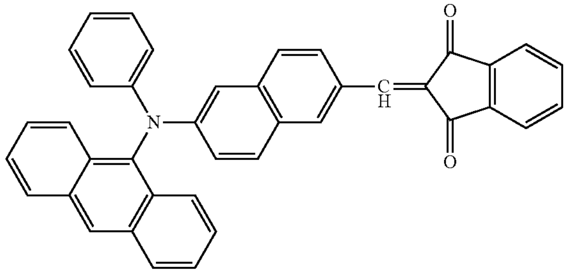

-continued
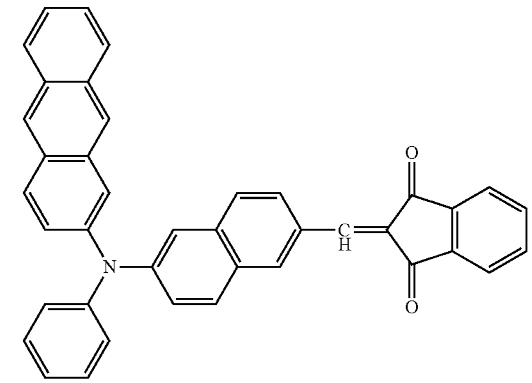
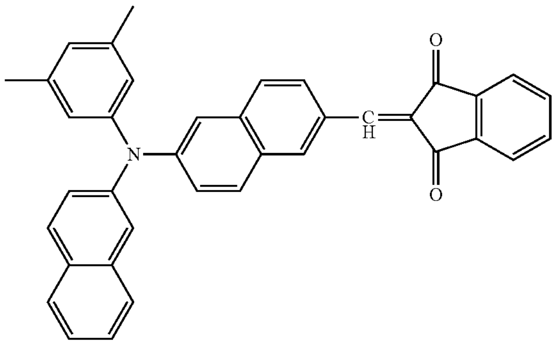
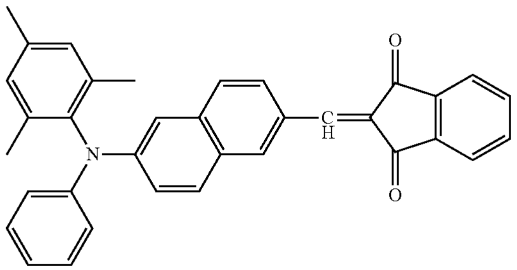
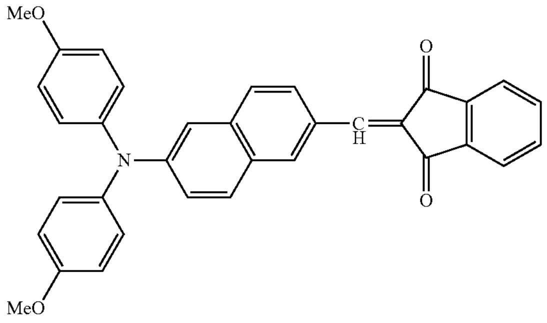
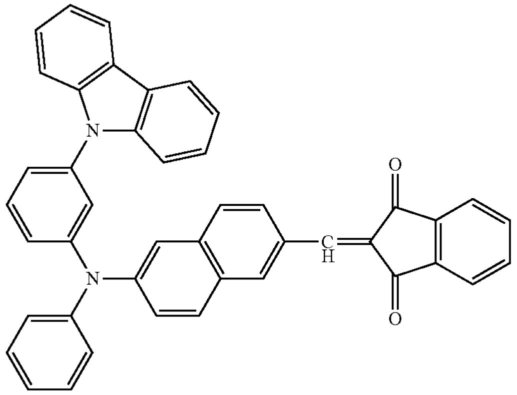
-continued
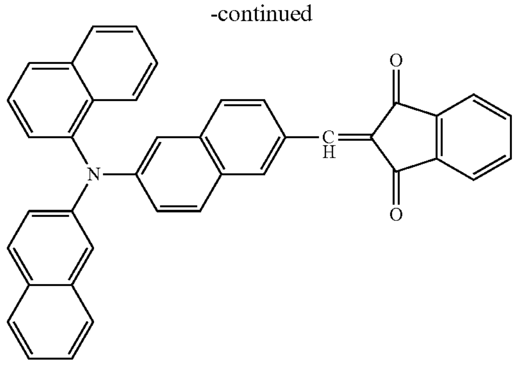
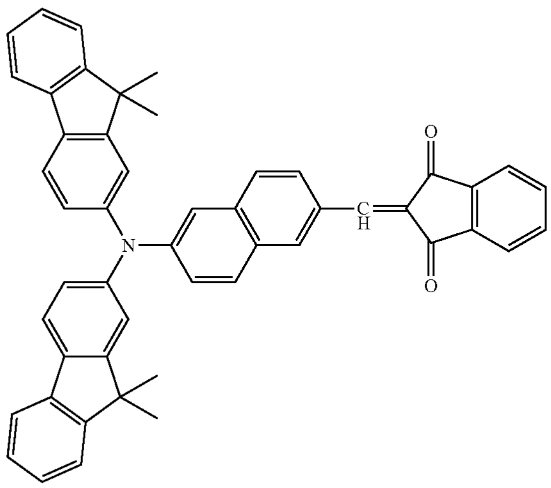
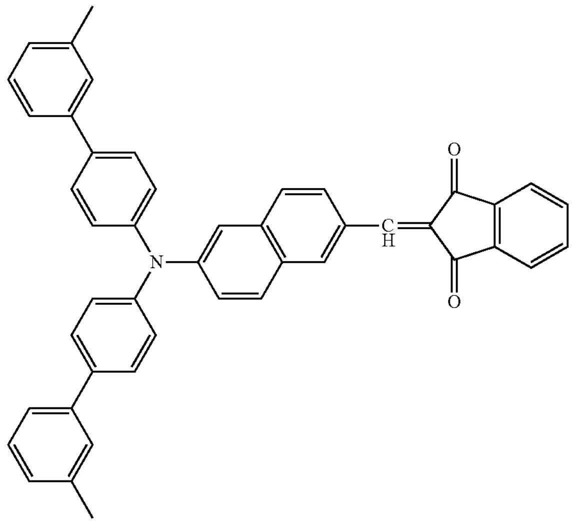

-continued
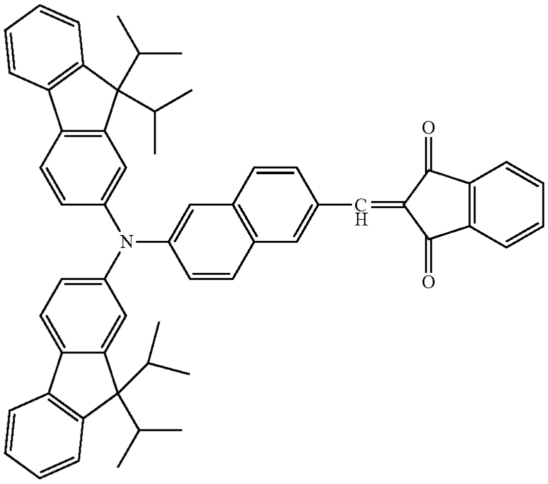
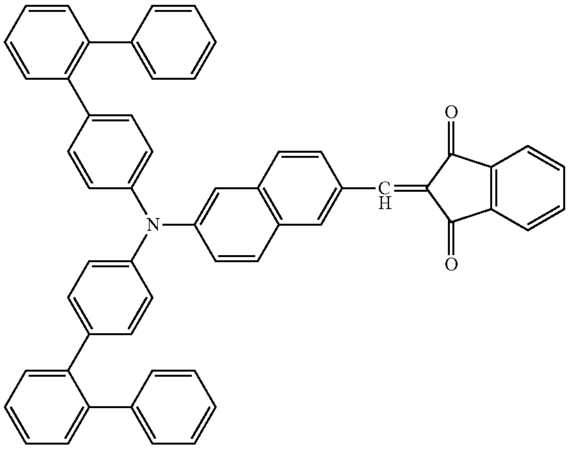
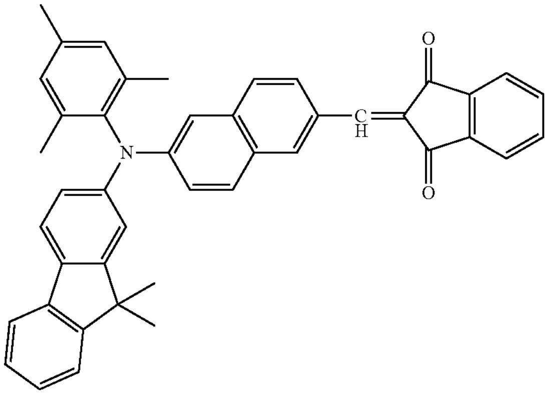
-continued
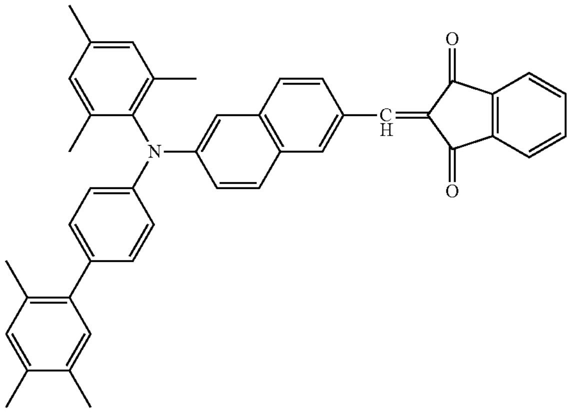
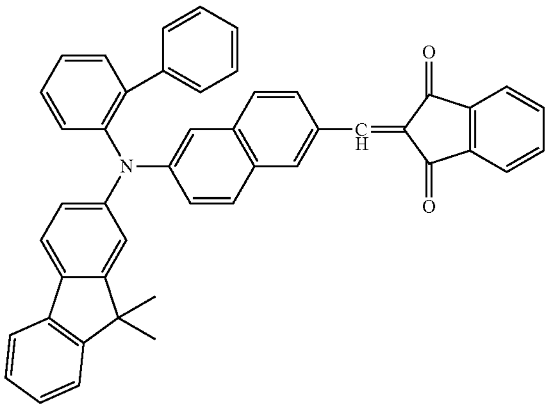
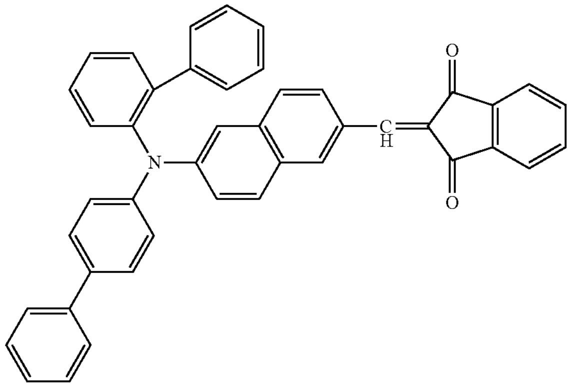
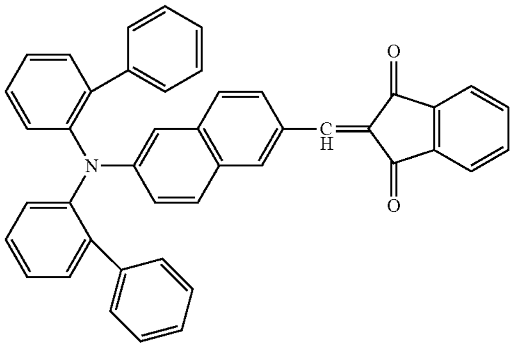

-continued
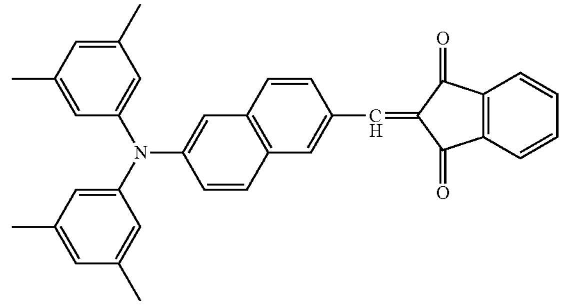
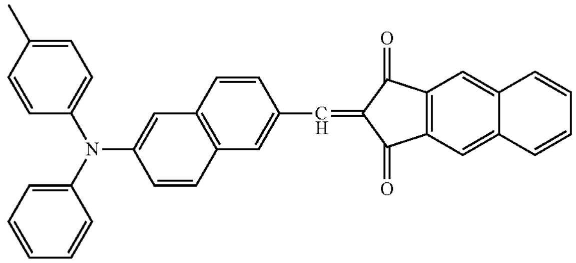
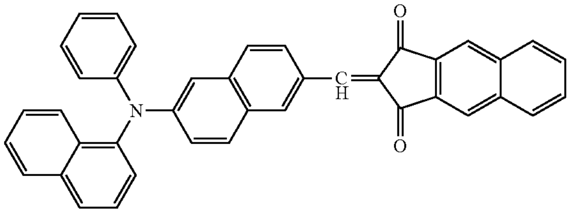
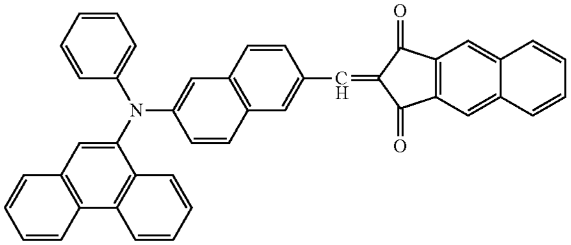
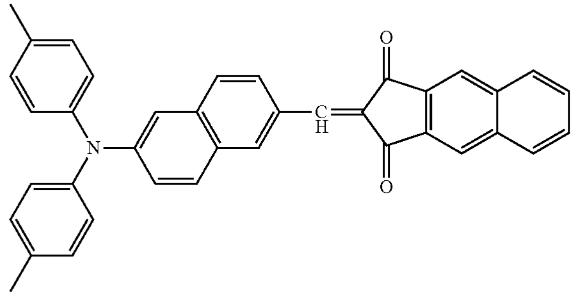
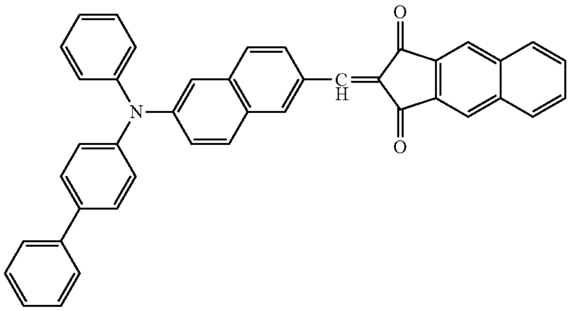
-continued
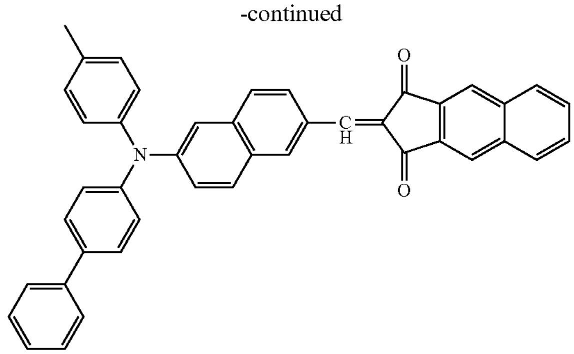
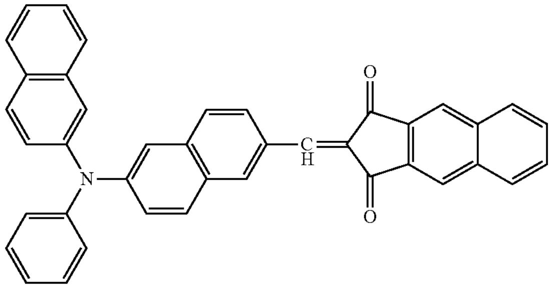
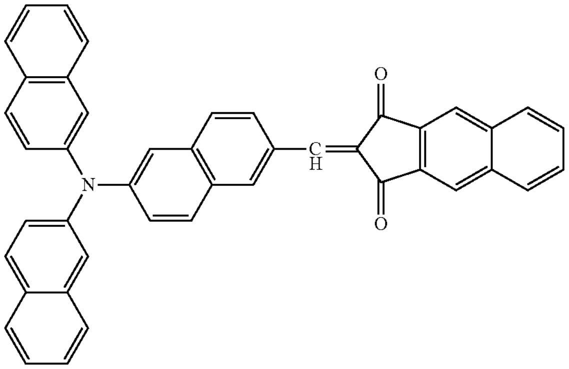
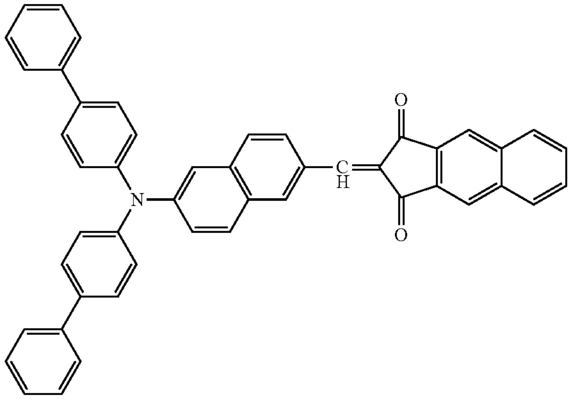
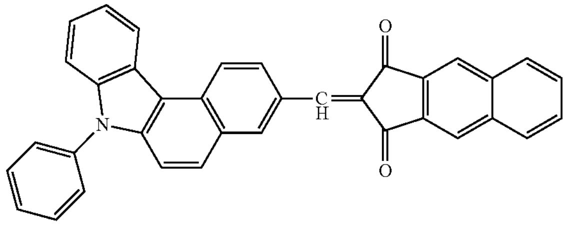

-continued
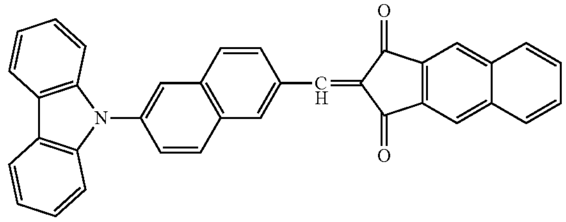
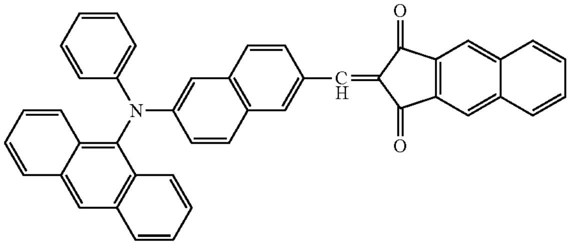
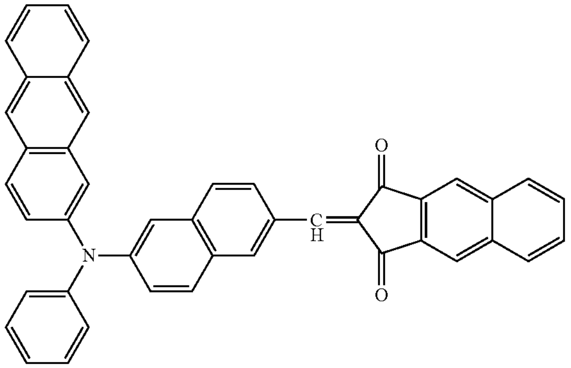
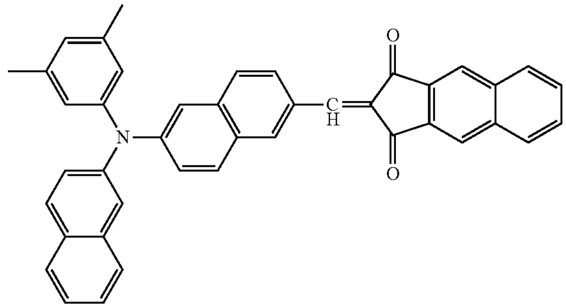
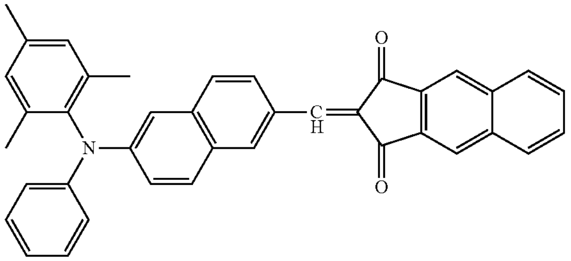
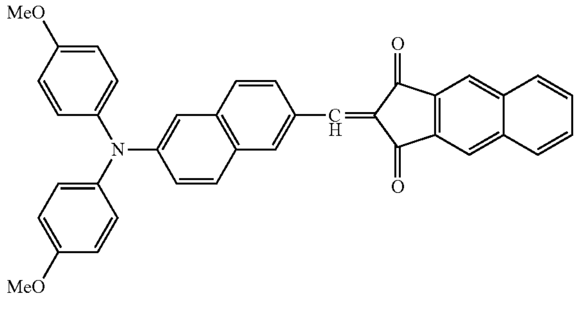
-continued
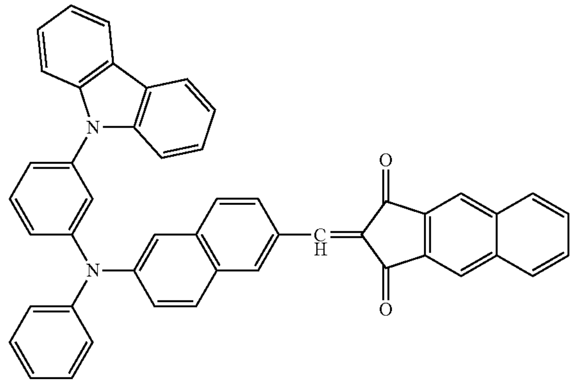
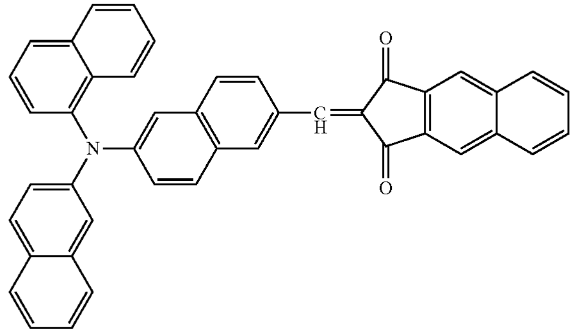
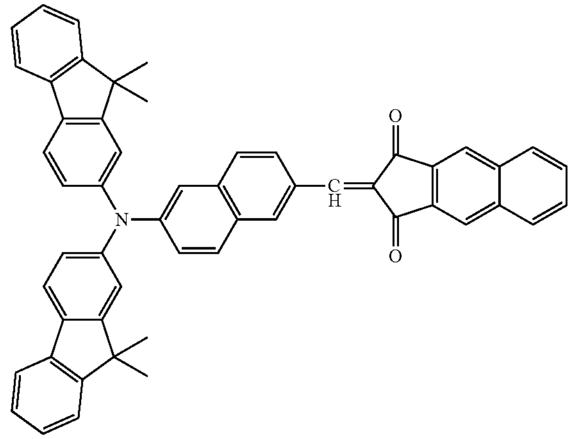
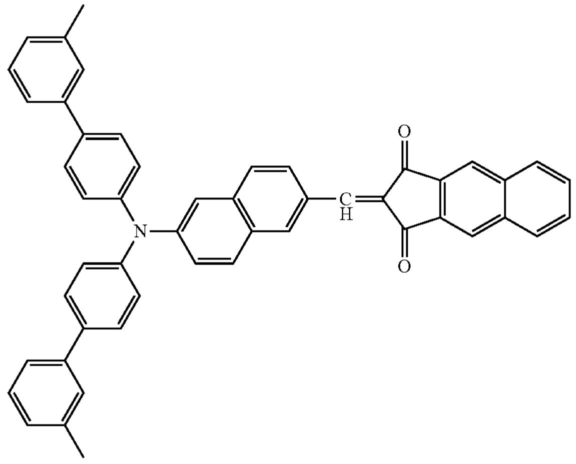

-continued
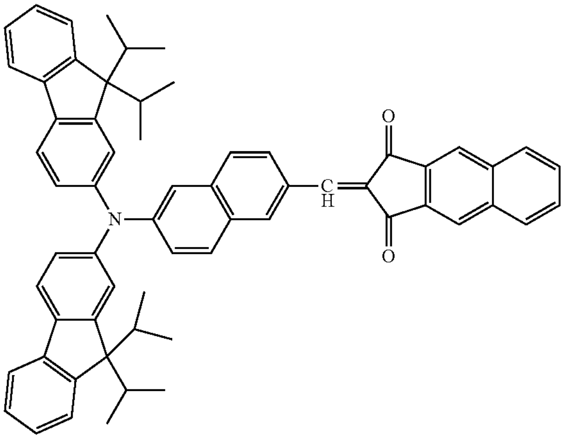
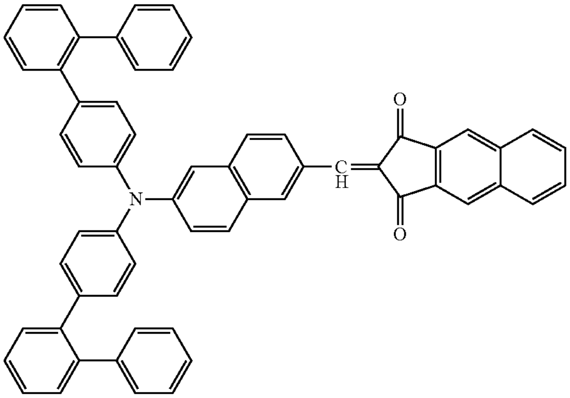
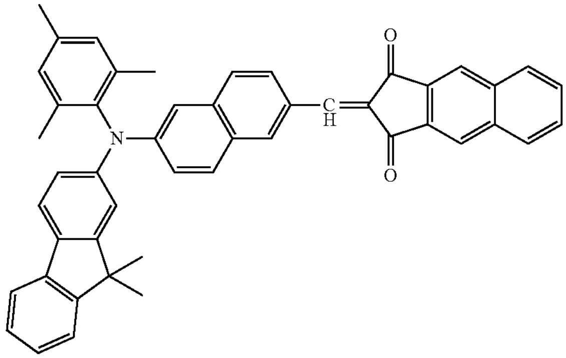
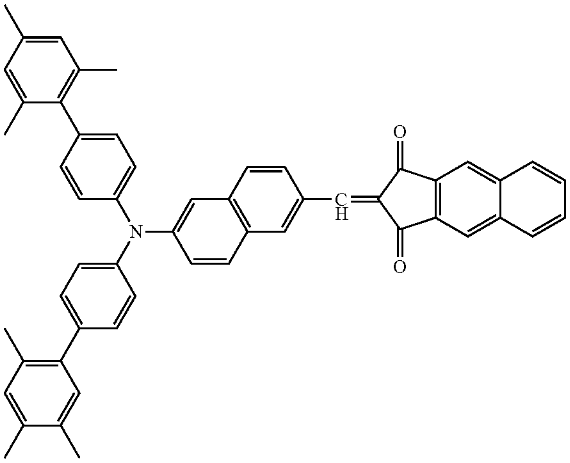
-continued
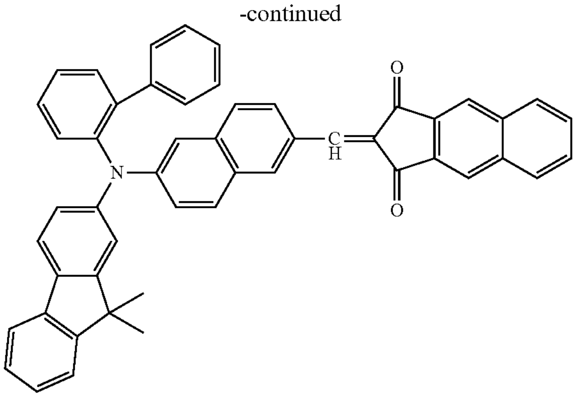
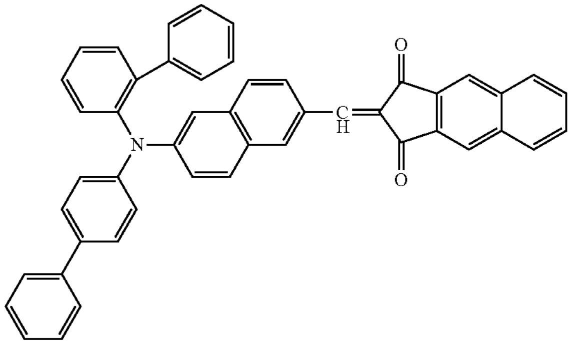
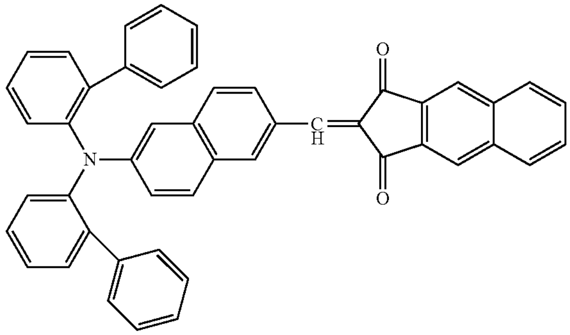
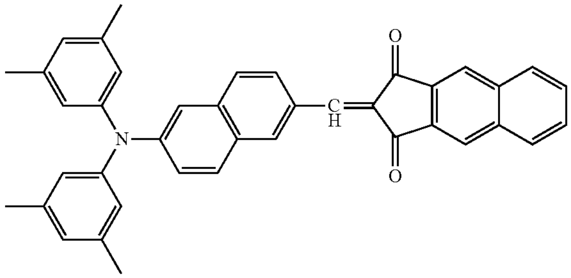
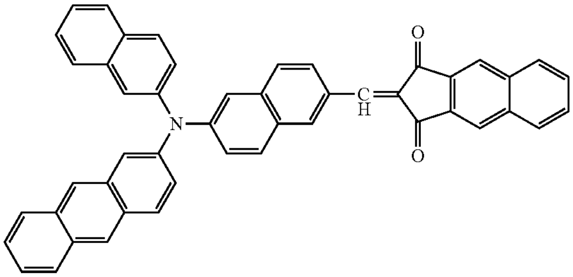

-continued
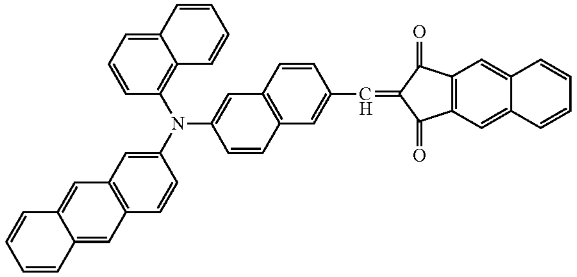
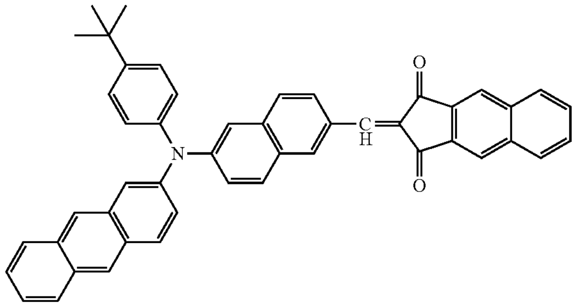
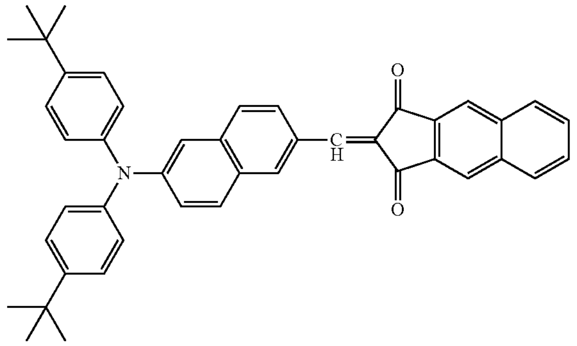
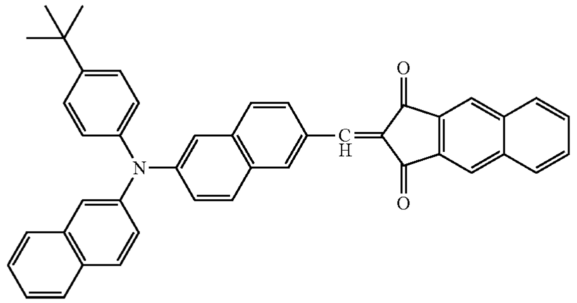
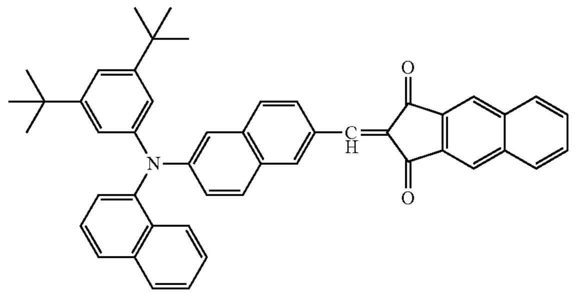
-continued
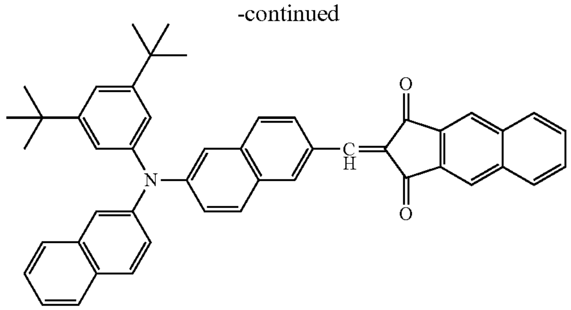
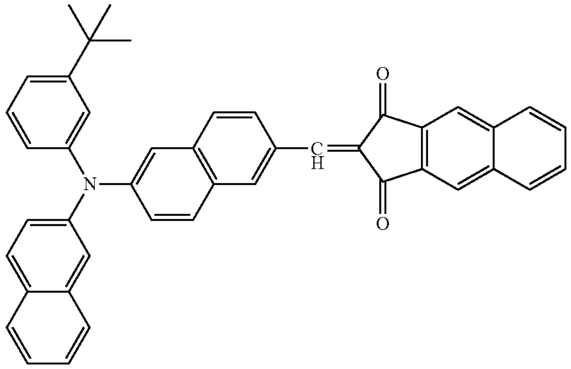
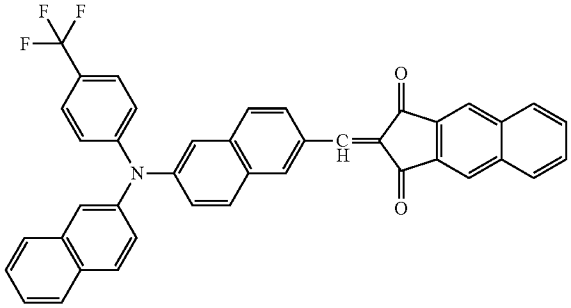
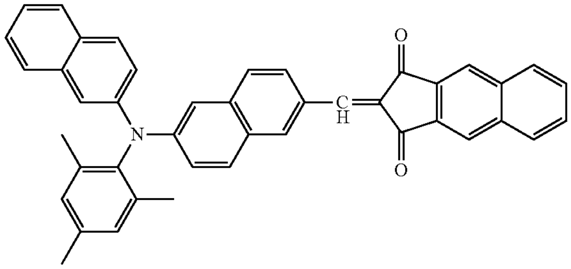
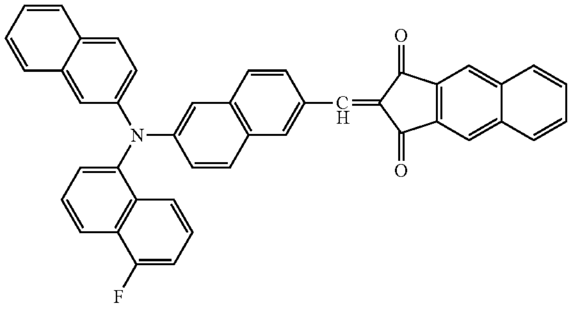

-continued
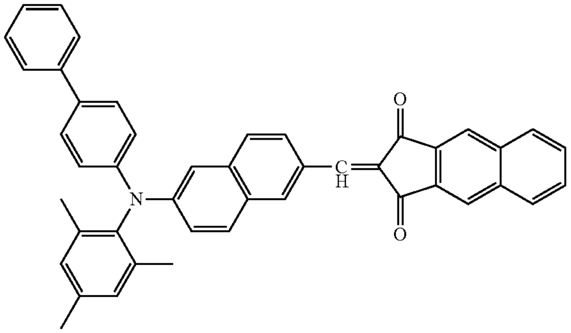
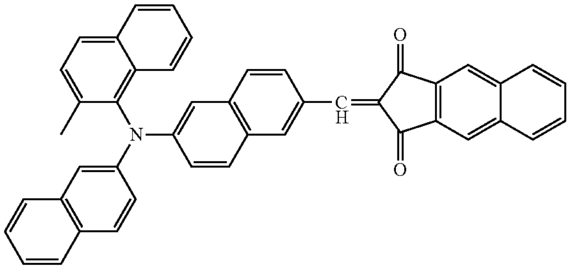
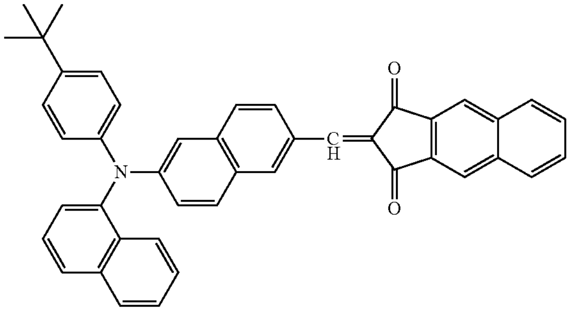
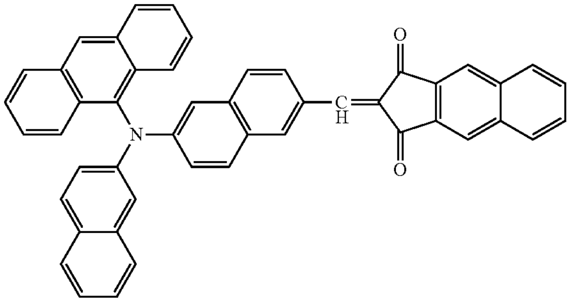
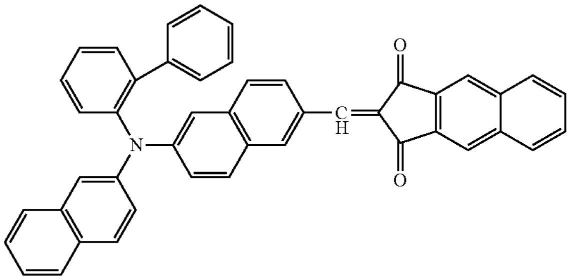
-continued
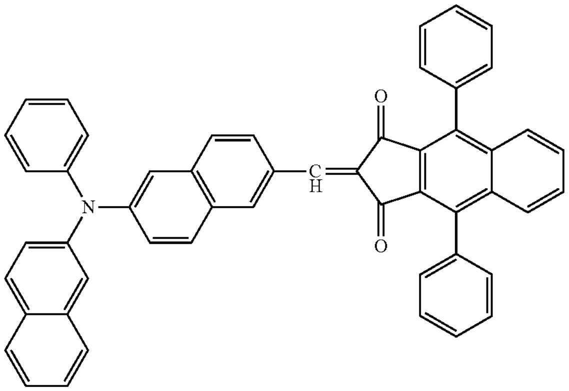
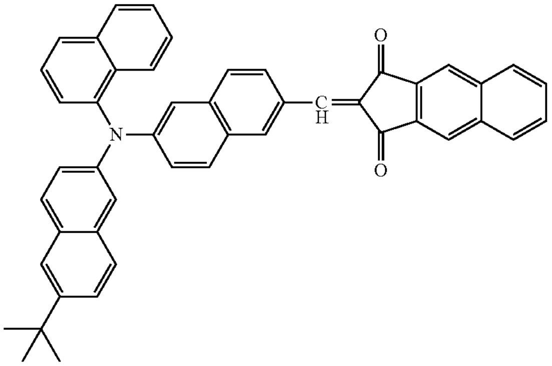
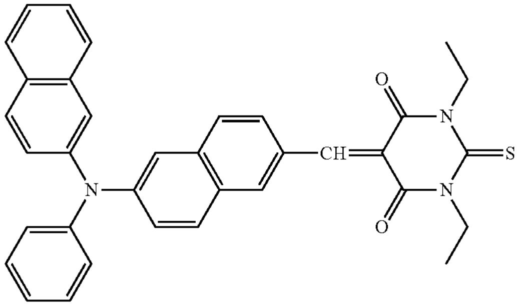
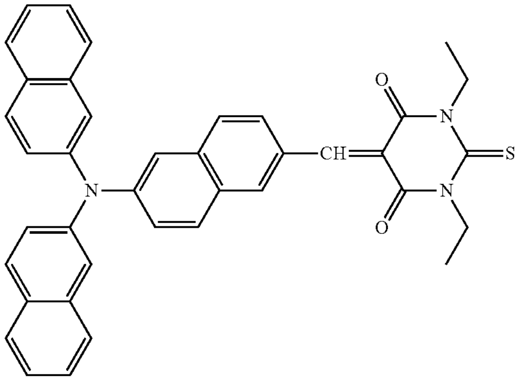

-continued
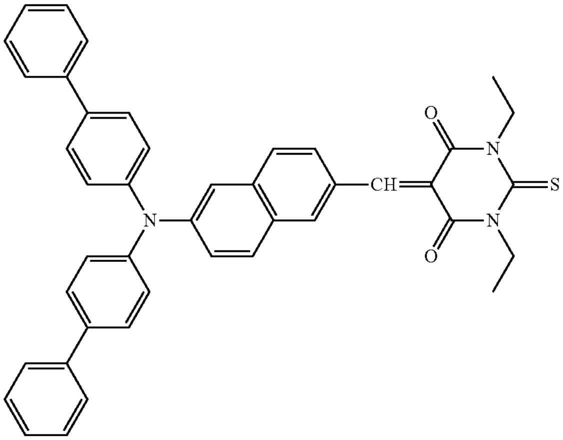
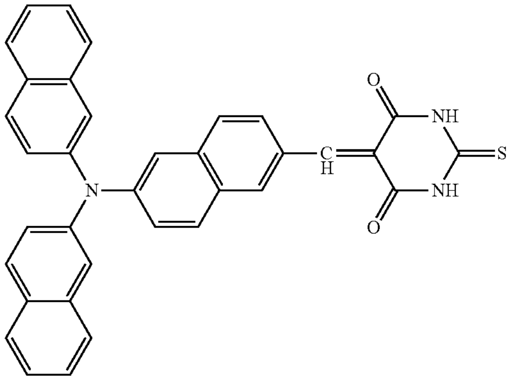
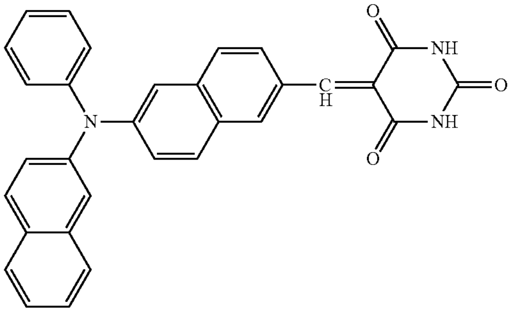
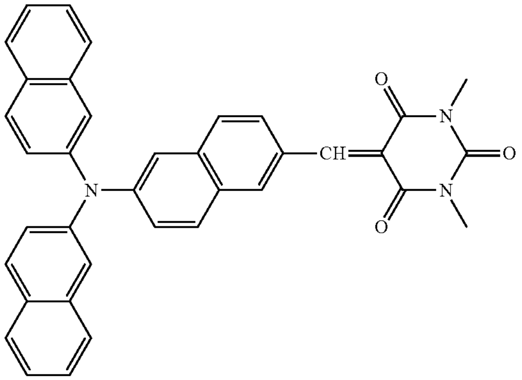
-continued
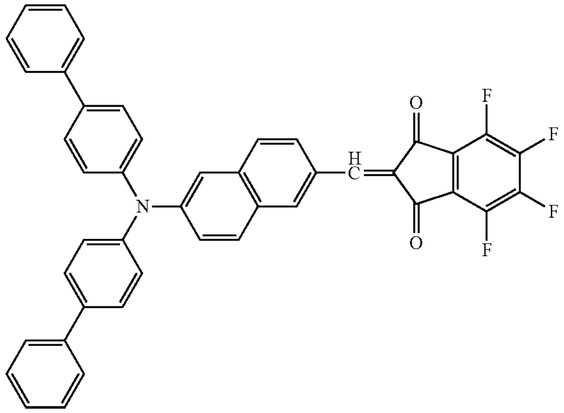
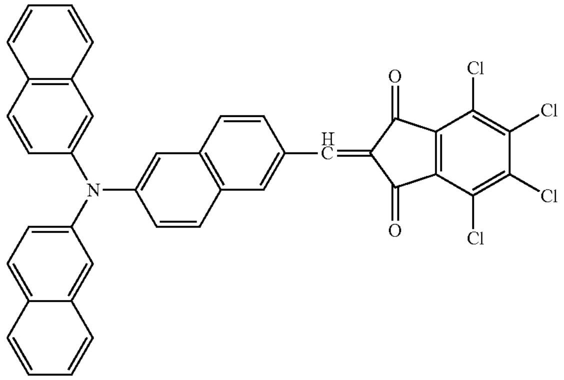
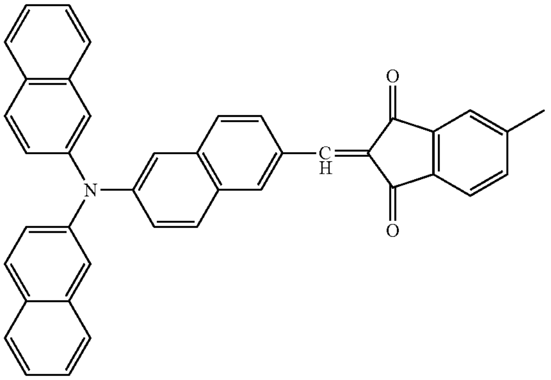
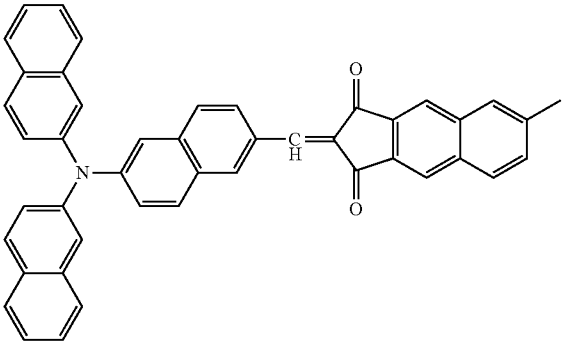

-continued
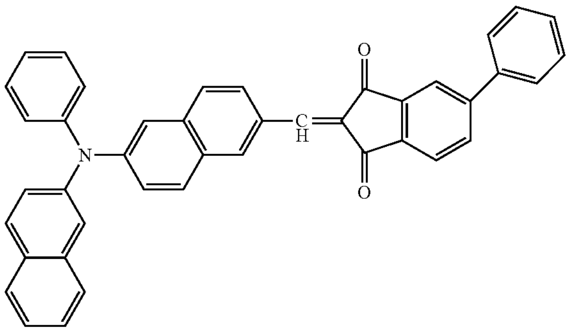
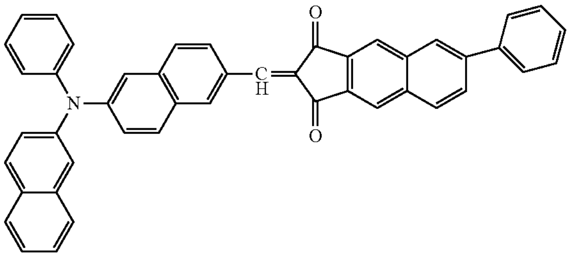
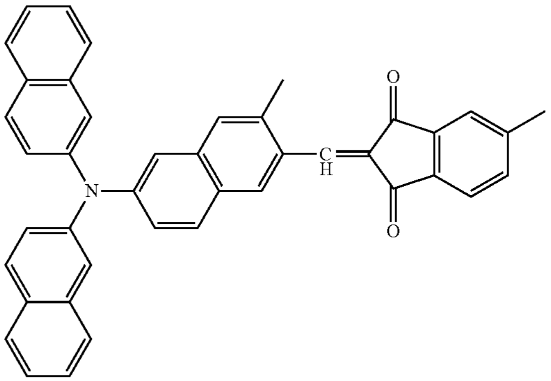
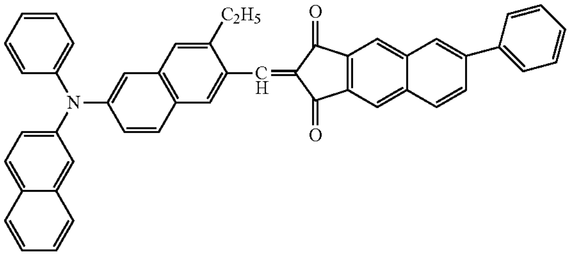
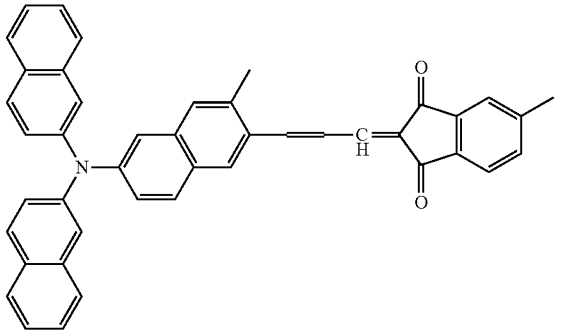
-continued
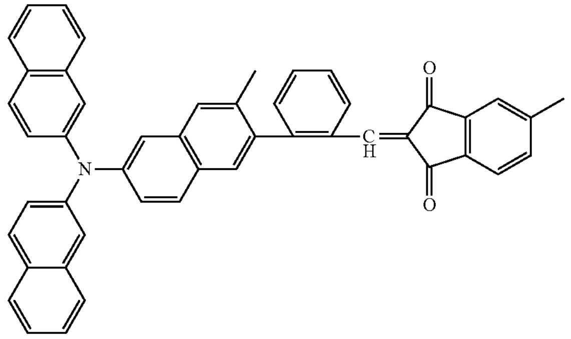
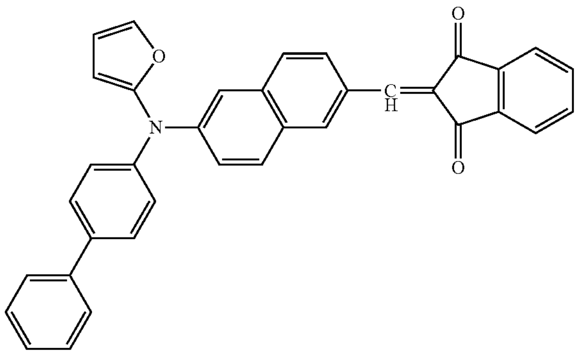
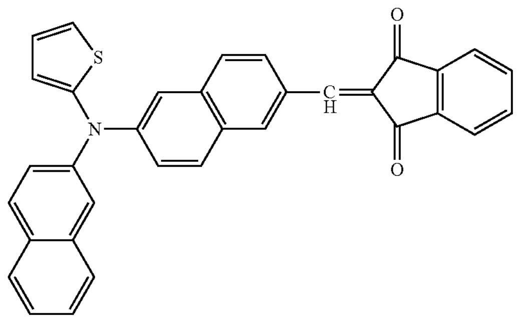
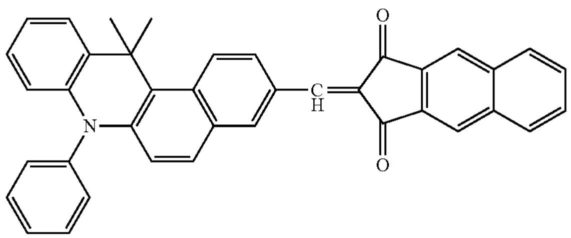
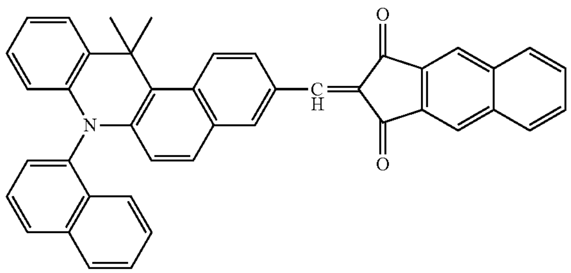

-continued
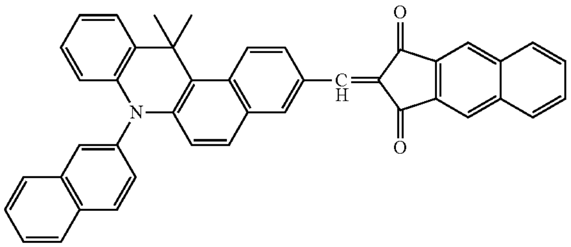
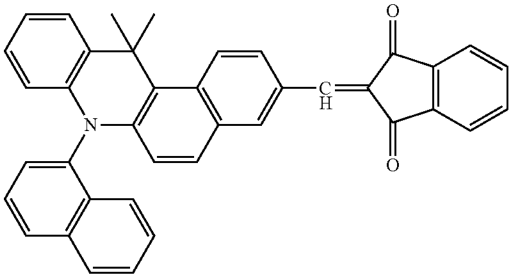
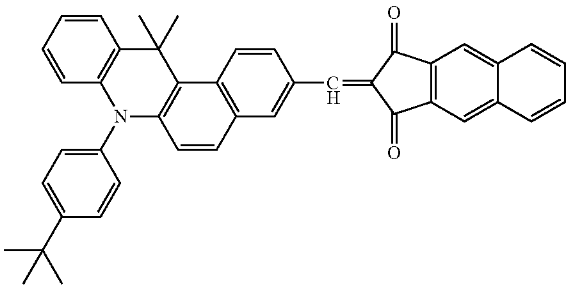
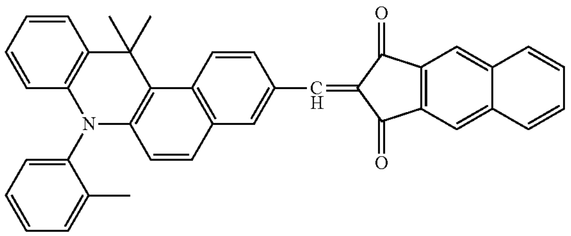
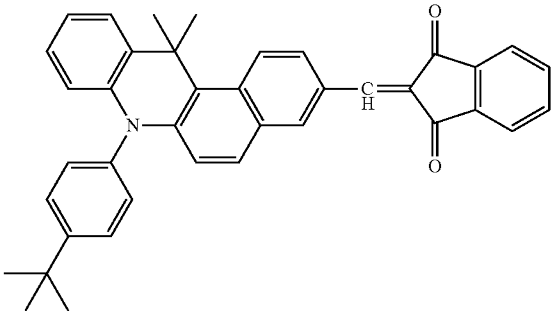
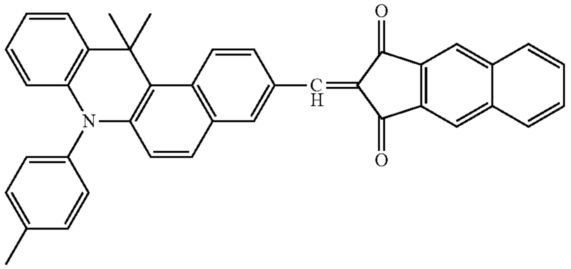
-continued
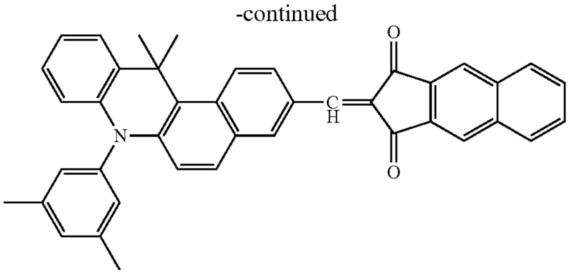
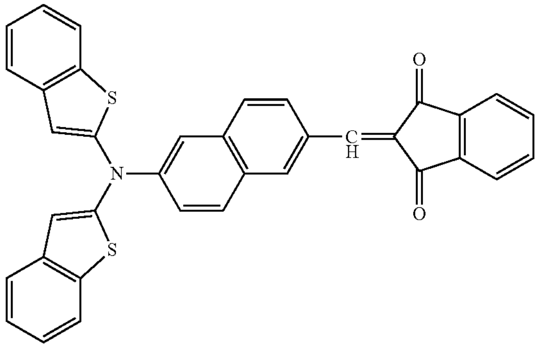
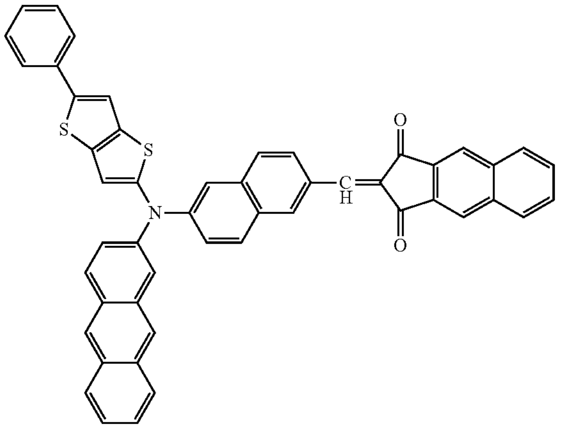
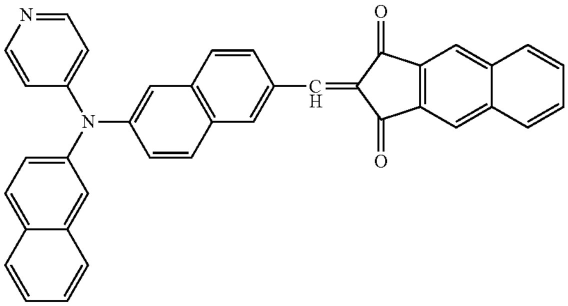
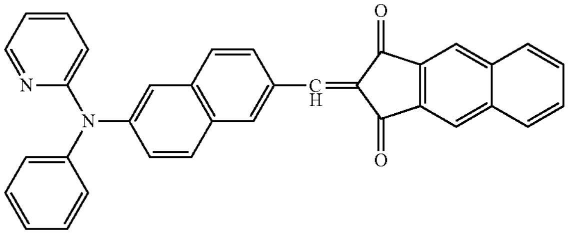

-continued

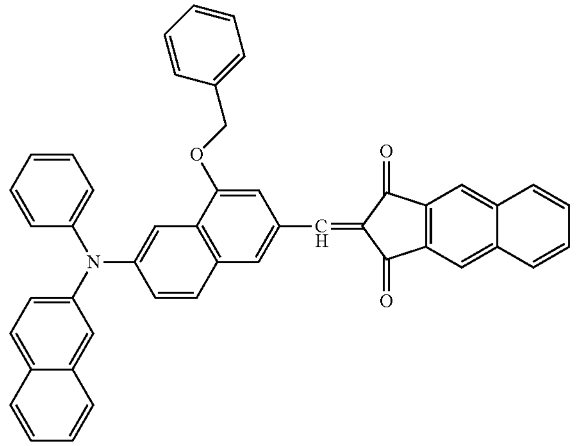

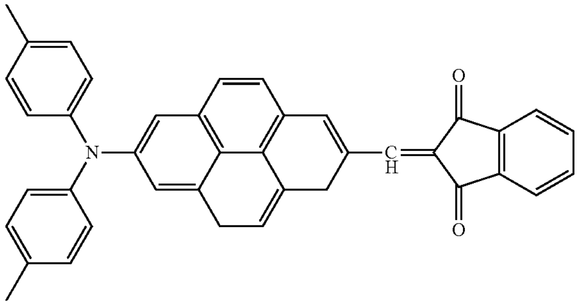 [SMILES: Cc1ccc(N(c2ccc(C)cc2)c2cc3c4c5c(ccc4c2)C=C(C=C2C(=O)c4ccccc4C2=O)CC5=CC3)cc1]

Out of the compounds described above, the compounds represented by formulae (I) to (IV) are novel compounds not found in literatures and are useful particularly as a photoelectric conversion material used in photosensors and photocells. Also, as other applications, the compounds can be used, for example, as a coloring material, a liquid crystal material, an organic semiconductor material, an organic luminescence device material, a charge transport material, a medical material, a fluorescent diagnostic agent material and the like.

The compounds represented by formulae (I) to (IV) can be synthesized, for example, according to the following reactions.

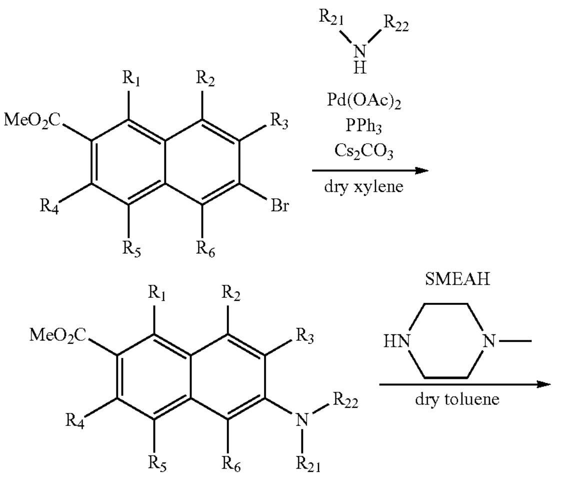

1a

-continued

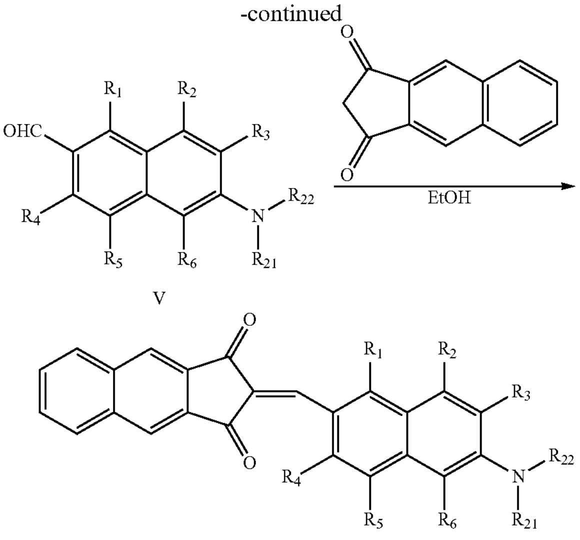

V (IIIa)

In these formulae, $R_1$, $R_2$, $R_3$, $R_4$, $R_5$, $R_6$, $R_{21}$ and $R_{22}$ have the same meanings as above.

In the synthesis example above, out of the compounds represented by formula (I), a compound where $Z_1$ is a 1,3-benzoindandione nucleus is described, but also in the case where $Z_1$ is other structures, the compound can be synthesized in the same manner as above by changing the 1,3-benzoindandione to other compounds.

The compound represented by formula (V), which is an intermediate compound in the reaction formula above, is a novel compound. The present invention also relates to the compound represented by formula (V).

Formula (V):

(V)

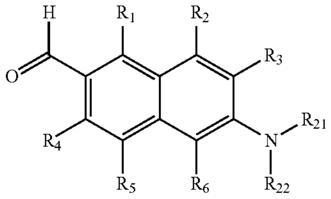

(wherein each of $R_1$, $R_2$, $R_3$, $R_4$, $R_5$ and $R_6$ independently represents a hydrogen atom or a substituent, $R_1$ and $R_2$, $R_2$ and $R_3$, $R_4$ and $R_5$, or $R_5$ and $R_6$ may combine with each other to form a ring, and each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded).

In formula (V), $R_1$, $R_2$, $R_3$, $R_4$, $R_5$, $R_6$, $R_{21}$ and $R_{22}$ have the same meanings as those in formula (I), and the preferred ranges are also the same.

Each reaction in the synthesis example above can be performed by utilizing a known technique. The reaction of a bromo form with amine is known as a Buchwald-Hartwig reaction (see, *Org. Synth.*, 2004, 10, 423, and *Org. Synth.*, 2002, 78, 23). The reduction reaction from the ester form to the aldehyde form can be performed by referring to *Synthesis,*

2003, 822. The reaction of the aldehyde form and benzoindandione can be performed by referring to *Ber. Deutsch. Chem. Ges.*, 1898, 31, 2596.

(Molecular Weight)

In view of suitability for film production, the molecular weight of the compounds represented by formulae (I) to (IV) is preferably from 300 to 1,500, more preferably from 350 to 1,200, still more preferably from 400 to 900. If the molecular weight is too small, the thickness of the photoelectric conversion film produced is reduced due to volatilization, whereas if the molecular weight is excessively large, the compound cannot be vapor-deposited and a photoelectric conversion device cannot be fabricated.

(Melting Point)

In view of deposition stability, the melting point of the compounds represented by formulae (I) to (IV) is preferably 200° C. or more, more preferably 220° C. or more, still more preferably 240° C. or more. If the melting point is low, the compound melts out before vapor deposition, making it impossible to stably produce a film, and in addition, the decomposition product of the compound increases to deteriorate the photoelectric conversion performance.

(Absorption Spectrum)

From the standpoint of broadly absorbing light in the visible region, the peak wavelength in the absorption spectrum of the compounds represented by formulae (I) to (IV) is preferably from 450 to 700 nm, more preferably from 480 to 700 nm, still more preferably from 510 to 680 nm.

(Molar Extinction Coefficient of Peak Wavelength)

From the standpoint of efficiently utilizing light, the molar extinction coefficient of the compounds represented by formulae (I) to (IV) is preferably higher. In the visible region at a wavelength of 400 to 700 nm, the absorption spectrum (in a chloroform solution) preferably has a molar extinction coefficient of 20,000 $M^{-1}$ $cm^{-1}$, more preferably 30,000 $M^{-}$1 $cm^{-1}$ or more, still more preferably 40,000 $M^{-1}$ $cm^{-1}$ or more.

The organic photoelectric conversion film preferably further contains an n-type organic semiconductor in addition to the compound represented by formula (I). It is preferred that the n-type organic semiconductor is contained in the photoelectric conversion layer 12 together with the compound represented by formula (I).

The n-type organic semiconductor is an acceptor-type organic semiconductor and indicates an organic compound having a property of readily accepting an electron, mainly typified by an electron-transporting organic compound. More specifically, this is an organic compound having a larger electron affinity when two organic compounds are used in contact. Accordingly, for the acceptor-type organic compound, any organic compound can be used as long as it is an organic compound having an electron accepting property. Examples thereof include a fullerene or fullerene derivative, a fused aromatic carbocyclic compound (a naphthalene derivative, an anthracene derivative, a phenanthrene derivative, a tetracene derivative, a pyrene derivative, a perylene derivative and a fluoranthene derivative), a 5- to 7-membered heterocyclic compound containing a nitrogen atom, an oxygen atom or a sulfur atom (e.g., pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyralidine, pyrrolopyridine, thiadiazolopyridine, dibenzazepine, tribenzazepine), a polyarylene compound, a fluorene compound, a cyclopentadiene compound, a silyl compound, and a metal complex having a nitrogen-containing heterocyclic compound as a ligand.

The n-type semiconductor is preferably a fullerene or a fullerene derivative.

The fullerene indicates fullerene $C_{60}$, fullerene $C_{70}$, fullerene $C_{76}$, fullerene $C_{78}$, fullerene $C_{80}$, fullerene $C_{82}$, fullerene $C_{84}$, fullerene $C_{90}$, fullerene $C_{96}$, fullerene $C_{240}$, fullerene $C_{540}$, a mixed fullerene or a fullerene nanotube, and the fullerene derivative indicates a compound obtained by adding a substituent to such a fullerene. The substituent is preferably an alkyl group, an aryl group or a heterocyclic group.

The compounds described in JP-A-2007-123707 are preferred as the fullerene derivative.

As for the fullerene and fullerene derivative, the compounds described, for example, in *Kikan Kagaku Sosetsu* (*Scientific Review Quarterly*), No. 43, edited by The Chemical Society of Japan (1999), JP-A-10-167994, JP-A-11-255508, JP-A-11-255509, JP-A-2002-241323 and JP-A-2003-196881 may also be used.

Out of a fullerene and a fullerene derivative, a fullerene is preferred, and fullerene $C_{60}$ is more preferred.

The organic photoelectric conversion film preferably has a bulk heterojunction structure formed in a state of the compound represented by formula (I) and a fullerene or a fullerene derivative being mixed. The bulk heterojunction structure refers to a film in which a p-type organic semiconductor (compound represented by formula (I)) and an n-type organic semiconductor are mixed and dispersed within the photoelectric conversion layer and can be formed by, for example, a vapor co-deposition method. The heterojunction structure contained therein compensates for a drawback that the carrier diffusion length in the photoelectric conversion layer is short, whereby the photoelectric conversion efficiency of the photoelectric conversion layer can be enhanced. Incidentally, the bulk heterojunction structure is described in detail, for example, in JP-A-2005-303266, paragraphs [0013] and [0014], or the like.

The volume ratio of the fullerene or fullerene derivative to the compound represented by formula (I) (the fullerene or fullerene derivative/the compound represented by formula (I)×100(%)) in the organic photoelectric conversion film is preferably 50% or more, more preferably from 80 to 1,000% (volume ratio), still more preferably from 100 to 700% (volume ratio).

(Non-Luminescent Film)

In the organic photoelectric conversion film, the film in which the compound represented by any of formulae (I) to (IV) and the n-type organic semiconductor are mixed is a non-luminescent film and has a characteristic feature different from OLED. The non-luminescent film is a film having a luminescence quantum efficiency of 1% or less, and the luminescence quantum efficiency is more preferably 0.5% or less, still more preferably 0.1% or less.

The organic photoelectric conversion film can be deposited by a dry deposition method or a wet deposition method. Specific examples of the dry deposition method include a physical vapor deposition method such as vacuum deposition method, sputtering method, ion plating method and MBE method, and a CVD method such as plasma polymerization. As for the wet deposition method, a cast method, a spin coating method, a dipping method, an LB method and the like are used. A dry deposition method is preferred, and a vacuum deposition method is more preferred. In the case of depositing the layer by a vacuum deposition method, the production conditions such as vacuum degree and vapor deposition temperature can be set in accordance with conventional methods.

The thickness of the photoelectric conversion layer is preferably from 10 to 1,000 nm, more preferably from 50 to 800 nm, still more preferably from 100 to 500 nm. With a thickness of 100 nm or more, a suitable effect of suppressing a dark current is obtained, and with a thickness of 1,000 nm or less, a suitable photoelectric conversion efficiency is obtained.

[Charge Blocking Layer: Electron Blocking Layer, Hole Blocking Layer]

(Electron Blocking Layer)

For the electron blocking layer, an electron-donating organic material can be used. Specifically, examples of the low molecular material which can be used include an aromatic diamine compound such as N,N'-bis(3-methylphenyl)-(1,1'-biphenyl)-4,4'-diamine (TPD) and 4,4'-bis[N-(naphthyl)-N-phenylamino]biphenyl (α-NPD), oxazole, oxadiazole, triazole, imidazole, imidazolone, a stilbene derivative, a pyrazolone derivative, tetrahydroimidazole, a polyarylalkane, butadiene, 4,4',4"-tris(N-(3-methylphenyl) N-phenylamino)triphenylamine (m-MTDATA), a porphyrin compound such as porphin, copper tetraphenylporphin, phthalocyanine, copper phthalocyanine and titanium phthalocyanine oxide, a triazole derivative, an oxadiazole derivative, an imidazole derivative, a polyarylalkane derivative, a pyrazoline derivative, a pyrazolone derivative, a phenylenediamine derivative, an arylamine derivative, a fluorene derivative, an amino-substituted chalcone derivative, an oxazole derivative, a styryl-anthracene derivative, a fluorenone derivative, a hydrazone derivative, and a silazane derivative. As for the polymer material, a polymer of such as phenylenevinylene, fluorene, carbazole, indole, pyrene, pyrrole, picolin, thiophene, acetylene and diacetylene, or a derivative thereof may be used. A compound having a sufficient hole transportability may be used even if it is not an electron-donating compound.

Specifically, the compounds described in JP-A-2008-72090, paragraphs [0083] to [0089] are preferred.

(Hole Blocking Layer)

For the hole-blocking layer, an electron-accepting organic material can be used.

Examples of the electron-accepting material which can be used include an oxadiazole derivative such as 1,3-bis(4-tert-butylphenyl-1,3,4-oxadiazolyl)phenylene (OXD-7); an anthraquinodimethane derivative; a diphenylquinone derivative; a bathocuproine, a bathophenanthroline and a derivative thereof; a triazole compound; a tris(8-hydroxyquinolinato) aluminum complex; a bis(4-methyl-8-quinolinato)aluminum complex; a distyrylarylene derivative; and a silole compound. Also, a material having sufficient electron transportability may be used even if it is not an electron-accepting organic material. A porphyrin-based compound, a styryl-based compound such as DCM (4-dicyanomethylene-2-methyl-6-(4-(dimethylaminostyryl))-4H pyran), and a 4H pyran-based compound can be used. Specifically, the compounds described in JP-A-2008-72090, paragraphs [0073] to [0078] are preferred.

The thickness of each of the electron blocking layer and the hole blocking layer is preferably from 10 to 200 nm, more preferably from 30 to 150 nm, still more preferably from 50 to 100 nm, because if this thickness is too small, the effect of suppressing a dark current is decreased, whereas if it is excessively large, the photoelectric conversion efficiency is reduced. When the photoelectric conversion device includes a charge blocking layer, it is more preferred that it includes the electron blocking layer.

[Photosensor]

The photoelectric conversion device is roughly classified into a photocell and a photosensor, and the photoelectric conversion device of the present invention is suited for a photosensor. The photosensor may be a photosensor using the above-described photoelectric conversion device alone or may be in the mode of a line sensor where the photoelectric conversion devices are linearly arranged, or a two-dimensional sensor where the photoelectric conversion devices are arranged on a plane. The photoelectric conversion device of the present invention functions as an imaging device, in the line sensor, by converting the optical image information into electric signals with use of an optical system and a drive part like, for example, a scanner and, in the two-dimensional sensor, by forming an image of optical image information on a sensor by means of an optical system and converting it into electric signals like an imaging module.

The photocell is a power generating unit and therefore, the efficiency of converting light energy into electric energy is an important performance, but the dark current that is a current in a dark place does not become a problem in function. Furthermore, a heating step in the later stage, such as placement of a color filter, is not required. In the photosensor, high-precision conversion of light/dark signals into electric signals is an important performance and in turn, the efficiency of converting light quantity into a current is also an important performance. Moreover, a signal when output in a dark place works out to a noise and therefore, low dark current is required. Furthermore, the resistance to a step in the later stage is also important.

[Imaging Device]

Configuration examples of an imaging device equipped with the photoelectric conversion device are described below. In the following configuration examples, the members and the like having the same configuration/action as the members described above are indicated by the same or like symbols or numerical references in the figure, and their description is simplified or omitted.

The imaging device is a device of converting optical information of an image into electric signals, where a plurality of photoelectric conversion devices are arranged in the same plane on a matrix and where light signals can be converted into electric signals in each photoelectric conversion device (pixel) and each pixel can sequentially output the electric signals to the outside of the imaging device. Therefore, the imaging device has one photoelectric conversion device and one or more transistors per one pixel.

Figure 2:
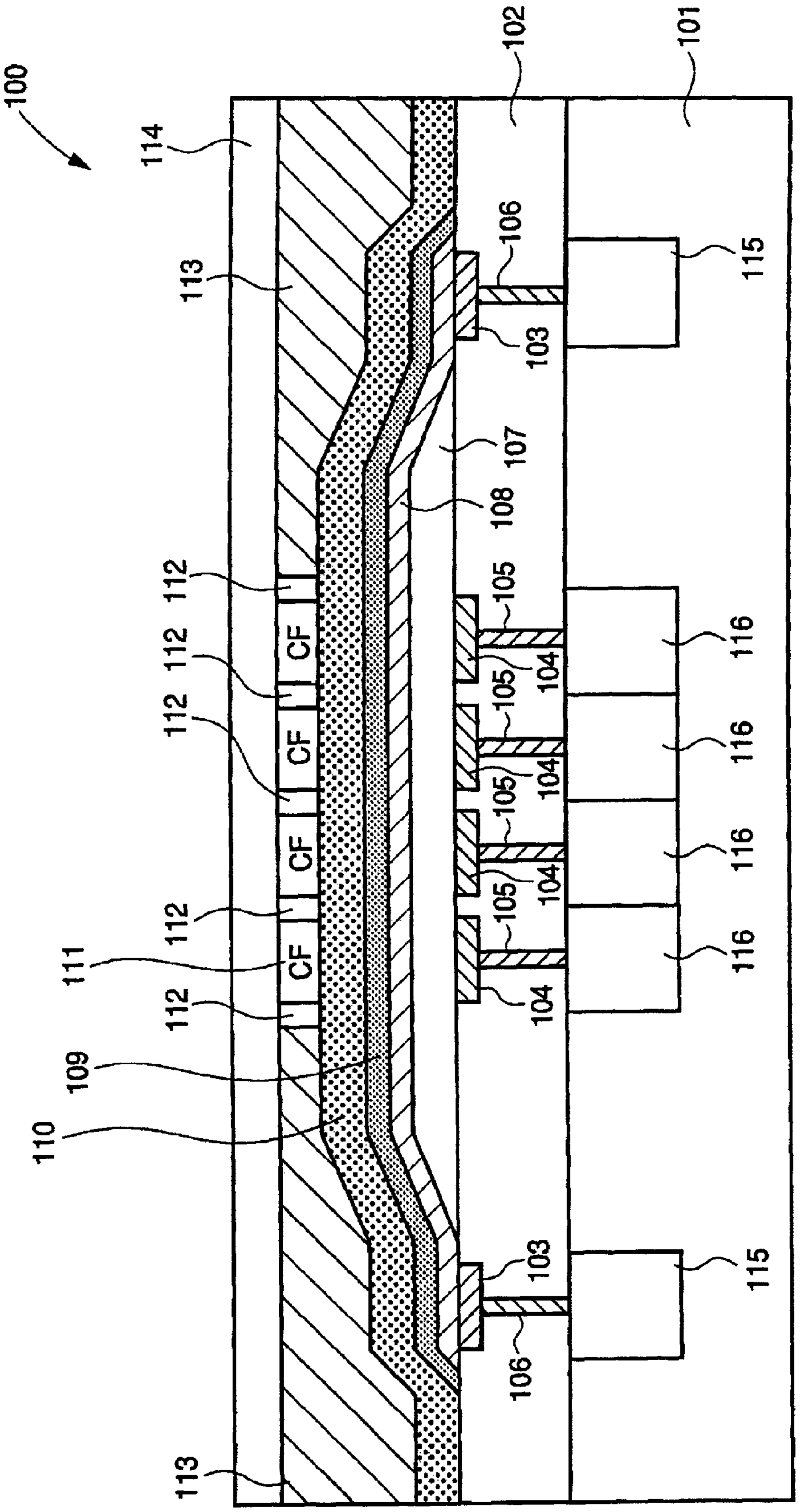
FIG. 2 is a schematic cross-sectional view of an imaging device.

FIG. 2 is a cross-sectional schematic view roughly showing the configuration of the imaging device for explaining one embodiment of the present invention. This imaging device is used by mounting it. for example, in an imaging apparatus such as digital camera and digital video camera, an electronic endoscope, or an imaging module such as cellular phone.

The imaging device has a plurality of photoelectric conversion devices in such a configuration as shown in FIGS. 1A and 1B and a circuit board having formed thereon a read-out circuit for reading out signals according to electric charges generated in the photoelectric conversion film of each photoelectric conversion device, wherein the plurality of photoelectric conversion devices are one-dimensionally or two-dimensionally arrayed on the same plane above the circuit board.

The imaging device 100 shown in FIG. 2 comprises a substrate 101, an insulating layer 102, a connection electrode 103, a pixel electrode (lower electrode) 104, a connection part 105, a connection part 106, a photoelectric conversion film 107, an opposite electrode (upper electrode) 108, a buffer layer 109, a passivation layer 110, a color filter (CF) 111, a partition wall 112, a light-shielding layer 113, a protective layer 114, an opposite electrode voltage supply part 115, and a read-out circuit 116.

The pixel electrode 104 has the same function as the electrode 11 of the photoelectric conversion device 10*a* shown in FIGS. 1A and 1B, and the opposite electrode 108 has the same function as the electrode 15 of the photoelectric conversion device 10*a* shown in FIGS. 1A and 1B. The photoelectric conversion film 107 has the same configuration as the layer provided between the electrode 11 and the electrode 15 of the photoelectric conversion device 10*a* shown in FIGS. 1A and 1B.

The substrate 101 is a glass substrate or a semiconductor substrate such as Si. An insulating layer 102 is formed on the substrate 101, and a plurality of pixel electrodes 104 and a plurality of connection electrodes 103 are formed on the surface of the insulating layer 102.

The photoelectric conversion film 107 is a layer shared in common by all photoelectric conversion devices provided on the plurality of pixel electrodes 104 to cover them.

The opposite electrode 108 is one electrode provided on the photoelectric conversion film 107 and shared in common by all photoelectric conversion devices. The opposite electrode 108 is formed to extend even on the connection electrode 103 disposed outside of the photoelectric conversion film 107 and is electrically connected to the connection electrode 103.

The connection part 106 is buried in the insulating layer 102 and is, for example, a plug for electrically connecting the connection electrode 103 and the opposite electrode voltage supply part 115. The opposite electrode voltage supply part 115 is formed on the substrate 101 and applies a predetermined voltage to the opposite electrode 108 through the connection part 106 and the connection electrode 103. In the case where the voltage applied to the opposite electrode 108 is higher than the source voltage of the imaging device, the predetermined voltage is supplied by raising the source voltage through a voltage raising circuit such as charge pump.

The read-out circuit 116 is provided on the substrate 101 to correspond to each of the plurality of pixel electrodes 104 and read out signals according to electric charges trapped by the corresponding pixel electrode 104. The read-out circuit 116 is composed of, for example, CCD, CMOS circuit or TFT circuit and light-shielded by a light-shielding layer (not shown) disposed in the insulating layer 102. The read-out circuit 116 is electrically connected to the corresponding pixel electrode 104 through the connection part 105.

The buffer layer 109 is formed on the opposite electrode 108 to cover the opposite electrode 108. The passivation layer 110 is formed on the buffer layer 109 to cover the buffer layer 109. The color filter 111 is formed at the position facing each pixel electrode 104 on the passivation layer 110. The partition wall 112 is provided between color filters 111 for enhancing the light transmission efficiency of the color filter 111.

The light-shielding layer 113 is formed on the passivation layer 110 in the area other than the region where the color filter 111 and the partition wall 112 are provided, and prevents light from entering the photoelectric conversion film 107 formed in the area other than the effective pixel region. The protective layer 114 is formed on the color filter 111, the partition wall 112 and the light-shielding layer 113 and protects the entire imaging device 100.

In the thus-configured imaging device 100, upon incidence of light, the light enters the photoelectric conversion film 107, and electric charges are generated there. Out of electric charges generated, holes are trapped by the pixel electrode 104, and voltage signals according to the amount of holes trapped are output by the read-out circuit 116 to the outside of the imaging device 100.

The production method of the imaging device 100 is as follows.

Connection parts 105 and 106, a plurality of connection electrodes 103, a plurality of pixel electrodes 104, and an insulating layer 102 are formed on a circuit board where an opposite electrode voltage supply part 115 and a read-out circuit 116 are formed. The plurality of pixel electrodes 104 are disposed, for example, in a square grid pattern on the insulating layer 102.

Subsequently, a photoelectric conversion film 107 is formed on the plurality of pixel electrode 104, for example, by vacuum heating deposition. Then, an opposite electrode 108 is formed on the photoelectric conversion film 107, for example, by sputtering in vacuum, and a buffer layer 109 and a passivation layer 110 are sequentially formed on the opposite electrode 108, for example, by vacuum heating deposition. Furthermore, a color filter 111, a partition wall 112 and a light-shielding layer 113 are formed, and a protective layer 114 is then formed, whereby an imaging device 100 is completed.

Also in the production method of the imaging device 100, even when a step of placing the imaging device 100 in a non-vacuum atmosphere on the way to fabrication is added between the step of forming a photoelectric conversion layer contained in the photoelectric conversion film 107 and the step of forming the passivation layer 110, the plurality of photoelectric conversion devices can be prevented from performance deterioration. Thanks to the addition of this step, the production cost can be reduced while preventing performance deterioration of the imaging device 100.

The passivation layer 110 as a constituent element of the above-described imaging device 100 is described in detail below.

[Passivation Layer]

The passivation layer 110 is required to satisfy the following conditions:

first, must block the intrusion of a factor that is contained in the solution, plasma and the like in each device production step and deteriorates an organic photoelectric conversion material, so as to protect the photoelectric conversion layer, secondly, must block the intrusion of a factor that deteriorates the organic photoelectric conversion material, such as water molecule, after the device production, so as to prevent deterioration of the photoelectric conversion film 107 over long-term storage/use, thirdly, must keep the already formed photoelectric conversion layer from deterioration when forming the passivation layer 110, and fourth, since incident light reaches the photoelectric conversion film 107 through the passivation layer 110, the passivation layer 110 must be transparent to light at the wavelength that is detected by the photoelectric conversion film 107.

The passivation layer 110 may have a thin-film configuration composed of a single material, but by having a multilayer configuration and imparting different functions to respective layers, an effect of, for example, relieving the stress of the entire passivation layer 110, suppressing the formation of a defect such as crack and pinhole due to dust generation or like in the production process, or facilitating the optimization of material development can be expected. For example, the passivation layer 110 can be formed in a two-layer configuration where a layer fulfilling its original purpose of preventing penetration of a deterioration factor such as water molecule is formed and a "passivation auxiliary layer" imparted with a function that is hard to achieve by the layer above is stacked thereon. A configuration composed of three or more layers may also be formed, but in view of the production cost, the number of layers is preferably smaller.

[Formation of Passivation Layer 110 by Atomic Layer Deposition Method (ALD Method)]

The performance of the photoelectric conversion material is significantly deteriorated due to the presence of a deterioration factor such as water molecule. Accordingly, the entire photoelectric conversion film needs to be encapsulated by covering it, for example, with a ceramic such as water molecule-impermeable dense metal oxide, metal nitride or metal nitride oxide or a diamond-like carbon (DLC). Conventionally, aluminum oxide, silicon oxide, silicon nitride, silicon nitride oxide, a stacked configuration thereof, or a stacked configuration of such a ceramic and an organic polymer is formed as a passivation layer by various vacuum deposition techniques. In the case of such a conventional passivation layer, a thin film can hardly grow in a bump that is formed due to a structured material on the substrate surface, a micro defect on the substrate surface, a particle adhering to the substrate surface, or the like (because the bump forms a shadow), and the film thickness becomes significantly thin as compared with the flat part. Therefore, the bump portion works out to a penetration route of a deterioration factor. In order to completely cover the bump with a passivation layer, the entire passivation layer is preferably made thick by forming it to have a film thickness of 1 μm or more in the flat part.

In an imaging device 100 having a pixel dimension of less than 2 μm, particularly about 1 μm, when the distance between the color filter 111 and the photoelectric conversion layer, that this, the film thickness of the passivation layer 110, is large, the incident light is diffracted/diffused within the passivation layer 110 to cause color mixing. To avoid this, the imaging device 100 having a pixel dimension of about 1 μm is preferably fabricated using a passivation layer material/a production method capable of causing no deterioration of the device performance even when the film thickness of the entire passivation layer 110 is decreased.

The atomic layer deposition (ALD) method is a kind of CVD method, and this is a technique of forming a thin film by alternately repeating the adsorption/reaction of an organic metal compound molecule, a metal halide molecule and a metal hydride molecule as thin film materials to the substrate surface and the decomposition of an unreacted group contained therein. The thin film material on reaching the substrate surface is in the state of the above-described low molecule and when a very small space allowing intrusion of a low molecule is present, a thin film can be grown. Therefore, a bump portion that is difficult to cover by the conventional thin film formation method can be completely covered (the thickness of the thin film grown in the bump portion is the same as the thickness of a thin film grown in the flat portion), that is, the bump covering property is very excellent. A bump formed due to a structured material on the substrate surface, a micro defect on the substrate surface, a particle adhering to the substrate surface, or the like can be completely covered and therefore, such a bump portion does not provide a penetration route to a deterioration factor for the photoelectric conversion material. When the passivation layer 110 is formed by the atomic layer deposition method, the required film thickness of the passivation layer can be more effectively reduced than in conventional techniques.

In the case of forming the passivation layer 110 by the atomic layer deposition method, a material corresponding to the above-described ceramic preferred for the passivation layer 110 can be appropriately selected. However, the material is limited to a material capable of undergoing thin film growth at a relatively low temperature, because the photoelectric conversion film of the present invention uses a photoelectric conversion material. According to the atomic layer deposition method using an alkyl aluminum or an aluminum halide as the material, a dense aluminum oxide thin film can be formed at a temperature of less than 200° C. at which the photoelectric conversion material is not deteriorated. In particular, when trimethyl aluminum is used, an aluminum oxide thin film can be advantageously formed even at about 100° C. Also in the case of silicon oxide or titanium oxide, similarly to the aluminum oxide, a dense thin film can be advantageously formed at less than 200° C. by appropriately selecting the material.

[Substituent W]

The substituent W is described below.

Examples of the substituent W include a halogen atom, an alkyl group (including a cycloalkyl group, a bicycloalkyl group and a tricycloalkyl group), an alkenyl group (including a cycloalkenyl group and a bicycloalkenyl group), an alkynyl group, an aryl group, a heterocyclic group (may also be called a hetero-ring group), a cyano group, a hydroxy group, a nitro group, a carboxy group, an alkoxy group, an aryloxy group, a silyloxy group, a heterocyclic oxy group, an acyloxy group, a carbamoyloxy group, an alkoxycarbonyloxy group, an aryloxycarbonyloxy group, an amino group (including an anilino group), an ammonio group, an acylamino group, an aminocarbonylamino group, an alkoxycarbonylamino group, an aryloxycarbonylamino group, a sulfamoylamino group, an alkylsulfonylamino group, an arylsulfonylamino group, a mercapto group, an alkylthio group, an arylthio group, a heterocyclic thio group, a sulfamoyl group, a sulfo group, an alkylsulfinyl group, an arylsulfinyl group, an alkylsulfonyl group, an arylsulfonyl group, an acyl group, an aryloxycarbonyl group, an alkoxycarbonyl group, a carbamoyl group, an arylazo group, a heterocyclic azo group, an imido group, a phosphino group, a phosphinyl group, a phosphinyloxy group, a phosphinylamino group, a phosphono group, a silyl group, a hydrazino group, a ureido group, a boronic acid group ($—B(OH)_2$), a phosphato group ($—OPO(OH)_2$), a sulfato group ($—OSO_3H$) and other known substituents.

More preferably, W represents, for example, the following (1) to (17):

(1) a halogen atom, such as fluorine atom, chlorine atom, bromine atom and iodine atom;

(2) an alkyl group, a linear, branched or cyclic alkyl group:

(2-a) an alkyl group, preferably an alkyl group having a carbon number of 1 to 30 (e.g., methyl, ethyl, n-propyl, isopropyl, tert-butyl, n-octyl, eicosyl, 2-chloroethyl, 2-cyanoethyl, 2-ethylhexyl), and (2-b) a cycloalkyl group, preferably a substituted or unsubstituted cycloalkyl group having a carbon number of 3 to 30 (e.g., cyclohexyl, cyclopentyl, 4-n-dodecylcyclohexyl);

(3) an alkenyl group, a linear, branched or cyclic alkenyl group having a carbon number of 2 to 30 (e.g., vinyl, allyl, styryl);

(4) an alkynyl group, preferably an alkynyl group having a carbon number of 2 to 30 (e.g., ethynyl, propargyl, trimethylsilylethynyl);

(5) an aryl group, preferably an aryl group having a carbon number of 6 to 30 (e.g., phenyl, p-tolyl, naphthyl, m-chlorophenyl, o-hexadecanoylaminophenyl, ferrocenyl);

(6) a heterocyclic group, preferably a monovalent group obtained by removing one hydrogen atom from a 5- or 6-membered aromatic or non-aromatic heterocyclic compound, more preferably a 5- or 6-membered aromatic heterocyclic group having a carbon number of 2 to 50 (e.g., 2-furyl, 2-thienyl, 2-pyrimidinyl, 2-benzothiazolyl; the heterocyclic group may also be a cationic heterocyclic group such as 1-methyl-2-pyridinio and 1-methyl-2-quinolinio);

(7) an alkoxy group, preferably an alkoxy group having a carbon number of 1 to 30 (e.g., methoxy, ethoxy, isopropoxy, tert-butoxy, n-octyloxy, 2-methoxyethoxy);

(8) an aryloxy group, preferably an aryloxy group having a carbon number of 6 to 30 (e.g., phenoxy, 2-methylphenoxy, 4-tert-butylphenoxy, 3-nitrophenoxy, 2-tetradecanoylaminophenoxy);

(9) an amino group, preferably an amino group, an alkylamino group having a carbon number of 1 to 30, or an anilino group having a carbon number of 6 to 30, such as amino, methylamino, dimethylamino, anilino, N-methyl-anilino and diphenylamino;

(10) an alkylthio group, preferably an alkylthio group having a carbon number of 1 to 30 (e.g., methylthio, ethylthio, n-hexadecylthio);

(11) an arylthio group, preferably an arylthio group having a carbon number of 6 to 30 (e.g., phenylthio, p-chlorophenylthio, m-methoxyphenylthio);

(12) a heterocyclic thio group, preferably a substituted or unsubstituted heterocyclic thio group having a carbon number of 2 to 30 (e.g., 2-benzothiazolylthio, 1-phenyltetrazol-5-ylthio);

(13) an alkyl- or aryl-sulfinyl group, preferably a substituted or unsubstituted alkylsulfinyl group having a carbon number of 1 to 30, or a substituted or unsubstituted arylsulfinyl group having a carbon number of 6 to 30, such as methylsulfinyl, ethylsulfinyl, phenylsulfinyl and p-methylphenylsulfinyl;

(14) an alkyl- or aryl-sulfonyl group, preferably an alkylsulfonyl group having a carbon number of 1 to 30, or an arylsulfonyl group having a carbon number of 6 to 30, such as methylsulfonyl, ethylsulfonyl, phenylsulfonyl and p-methylphenylsulfonyl;

(15) an acyl group, preferably a formyl group, an alkylcarbonyl group having a carbon number of 2 to 30, an arylcarbonyl group having a carbon number of 7 to 30, or a heterocyclic carbonyl group having a carbon number of 4 to 30 and being bonded to a carbonyl group through a carbon atom, such as acetyl, pivaloyl, 2-chloroacetyl, stearoyl, benzoyl, p-n-octyloxyphenylcarbonyl, 2-pyridylcarbonyl and 2-furylcarbonyl;

(16) a phosphino group, preferably a phosphino group having a carbon number of 2 to 30 (e.g., dimethylphosphino, diphenylphosphino, methylphenoxyphosphino); and

(17) a silyl group, preferably a silyl group having a carbon number of 3 to 30 (e.g., trimethylsilyl, triethylsilyl, triisopropylsilyl, tert-butyldimethylsilyl, phenyldimethylsilyl).

[Ring R]

The ring R includes an aromatic or non-aromatic hydrocarbon ring, a heterocyclic ring, and a polycyclic condensed ring formed by further combining these rings. Examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolidine ring, a quinoline ring, a phthalazine ring, a naphthylidine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiine ring, a phenothiazine ring and a phenazine ring.

EXAMPLES

Example 1

<Synthesis of Compound (1)>

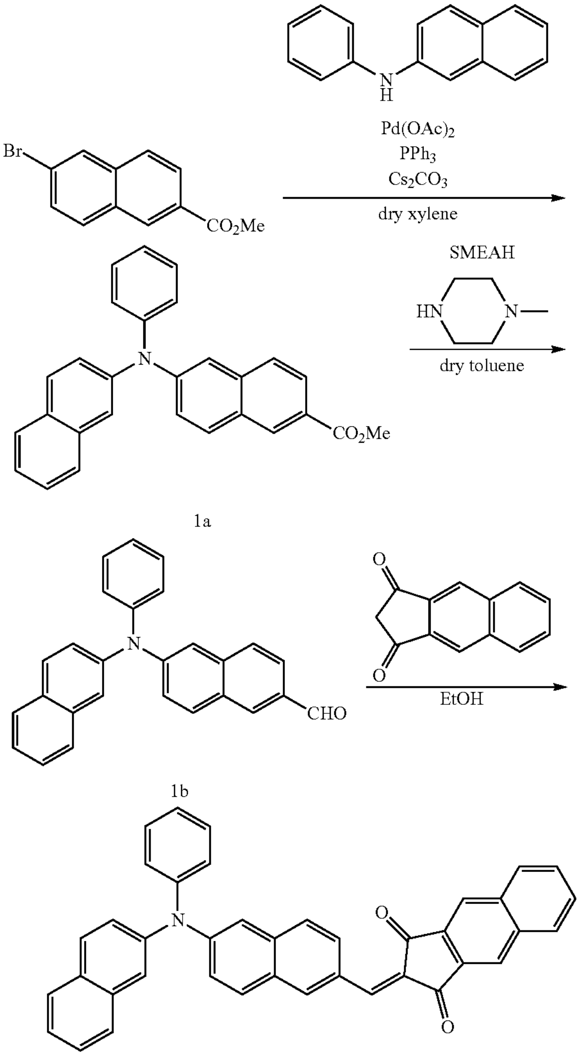

1a

1b

Compound (1)

(Synthesis of Compound 1a)

To 10 ml of dehydrated xylene, 4.0 g of N-phenyl-2-naphthylamine (produced by Tokyo Chemical Industry Co., Ltd.), 4.0 g of methyl 6-bromo-2-naphthoate (produced by Wako Pure Chemical Industries, Ltd.), 170 mg of palladium acetate, 590 mg of triphenylphosphine and 9.8 g of cesium carbonate were added, followed by refluxing for 3 hours. The reaction mixture was suction-filtered and after distilling off the solvent by an evaporator, the residue was purified on a silica gel column (developing solvent: toluene). The solvent was distilled off to obtain 6.2 g of Compound (1a).

(Synthesis of Compound 1b)

To 30 ml of dehydrated toluene, 23.6 ml of SMEAH (a toluene solution (about 70%) of sodium hydrogenated bis(2-methoxyethoxy)aluminum (produced by Wako Pure Chemical Industries, Ltd.)) was added, and after adjusting the inner temperature to 0° C. in an ice bath, a solution obtained by dissolving 9.9 ml of 1-methylpiperazine in 17 ml of dehydrated toluene was added dropwise. Separately, 6.2 g of Compound (1a) was dissolved in 50 ml of dehydrated toluene and after adjusting the inner temperature to −40° C. in a dry ice bath, the SMEAH toluene solution prepared above was added dropwise thereto. The resulting solution was stirred for 4.5 hours, and concentrated hydrochloric acid was added until the pH became 1. Furthermore, water and ethyl acetate were added thereto, and the oil layer was washed with an aqueous sodium hydrogencarbonate solution. The oil layer was dried over magnesium sulfate and filtered, and the solvent was distilled off by an evaporator. The reaction mixture was purified on a silica gel column, and the solvent was distilled off to obtain 4.2 g of Compound (1b).

<Identification of Compound (1b)>

$^1$H NMR ($CDCl_3$) δ: 7.15-7.28 (4H, m), 7.34-7.47 (6H, m), 7.56-7.66 (3H, m), 7.78-7.87 (4H, m), 8.23 (1H, s), 10.10 (1H, s).

(Synthesis of Compound (1))

2.0 g of Compound (1b) and 1.3 g of benzoindandione were added to a mixed solvent of 15 ml of toluene and 20 ml of ethanol, and the mixture was refluxed for 2 hours. The reaction mixture was allowed to cool and suction-filtered, and the material obtained by filtration was dissolved in a small amount of chloroform, recrystallized with ethanol and then suction-filtered to obtain 2.2 g of Compound (1). The identification of the compound was performed by $^1$H-NMR.

<Identification of Compound (1)>

$^1$H NMR ($CDCl_3$) δ: 7.19 (1H, t), 7.25 (2H, d), 7.34-7.48 (7H, m), 7.58-7.73 (5H, m), 7.83 (2H, d), 7.88 (1H, d), 8.12 (3H, m), 8.52 (2H, m), 8.60 (1H, d), 9.01 (1H, s).

Molecular weight: 551.63

<Measurement of Melting Point>

The melting point of Compound (1) was measured using TG/DTA 6200 AST-2 manufactured by SII NanoTechnology Inc. and found to be 254° C.

<Measurement of Absorption Spectrum>

The absorption spectrum (in a chloroform solution) of Compound (1) was measured using UV-2550 manufactured by Shimadzu Corporation, as a result, the peak wavelength was 542 nm and the molar extinction coefficient at this wavelength was 54,000 $M^{-1}$ $cm^{-1}$.

<Fabrication of Photoelectric Conversion Device and Solid-State Imaging Device>

A solid-state imaging device including a photoelectric conversion device of an embodiment of FIG. 2 was fabricated. Here, the photoelectric conversion device was composed of a lower electrode 104, a photoelectric conversion film 107 and an upper electrode 108, and an organic photoelectric conversion film including a photoelectric conversion layer and an electron blocking layer was formed as the photoelectric conversion film 107.

That is, amorphous ITO was deposited on a CMOS substrate by sputtering to a thickness of 30 nm and patterned by photolithography so that one pixel could be present for each photodiode (PD) on the CMOS substrate, whereby a pixel electrode (lower electrode) was formed. Subsequently, EB-3 shown below was deposited thereon by vacuum heating vapor deposition to a thickness of 100 nm to form an electron blocking layer, and a layer formed by co-depositing Compound (1) and fullerene ($C_{60}$) to a thickness of 100 nm and 300 nm, respectively, in terms of a single layer was deposited thereon by vacuum heating vapor deposition to form a photoelectric conversion layer in which Compound (1) and fullerene ($C_{60}$) formed a bulk heterojunction structure. Furthermore, amorphous ITO as an upper electrode was deposited to a thickness of 10 nm by sputtering to form a transparent electrode (upper electrode), whereby a solid-state imaging device was fabricated. After forming an SiO film as a passivation layer by heating vapor deposition on the upper electrode, an aluminum oxide layer was formed thereon by an ALD method. For both the electron blocking layer and the photoelectric conversion layer, the vacuum vapor deposition was performed at a vacuum degree of $4\times10^{-4}$ Pa or less.

Example 2

<Synthesis of Compound (2)>

Compound (2b) and Compound (2) were synthesized in the same manner as in Example 1 except for changing N-phenyl-2-naphthylamine to 2,2'-dinaphthylamine (produced by Tokyo Chemical Industry Co., Ltd.).

<Identification of Compound (2b)>

$^1$H NMR ($CDCl_3$) δ: 7.39 (4H, dd), 7.43-7.47 (4H, m), 7.58-7.66 (5H, m), 7.80-7.89 (6H, m), 8.24 (1H, s), 10.10 (1H, s).

<Identification of Compound (2)>

$^1$H NMR ($CDCl_3$) δ: 7.39-7.49 (8H, m), 7.60-7.74 (7H, m), 7.84 (4H, d), 7.90 (1H, d), 8.12 (3H, m), 8.53 (2H, d), 8.60 (1H, d), 9.04 (1H, s).

Molecular weight: 601.69

<Measurement of Melting Point>

The melting point of Compound (2) was measured in the same manner as in Example 1 and found to be 309° C.

<Measurement of Absorption Spectrum>

The absorption spectrum (in a chloroform solution) of Compound (2) was measured in the same manner as in Example 1, as a result, the peak wavelength was 548 nm and the molar extinction coefficient at this wavelength was 54,000 $M^{-1}$ $cm^{-1}$.

<Fabrication of Photoelectric Conversion Device and Solid-State Imaging Device>

A solid-state imaging device including a photoelectric conversion device was fabricated in the same manner as in Example 1 except for changing Compound (1) in the photoelectric conversion layer to Compound (2).

Example 3

<Synthesis of Compound (3)>

Compound (3) was synthesized in the same manner as in Example 1 except for changing benzoindandione to indandione.

<Identification of Compound (3)>

$^1$H NMR ($CDCl_3$) δ: 7.18 (1H, t), 7.23 (1H, d), 7.32-7.49 (7H, d), 7.57-7.68 (4H, m), 7.79-7.88 (5H, m), 8.02 (3H, m), 8.53 (1H, d), 8.92 (1H, s).

Molecular weight: 501.57

<Measurement of Melting Point>

The melting point of Compound (3) was measured in the same manner as in Example 1 and found to be 253° C.

<Measurement of Absorption Spectrum>

The absorption spectrum (in a chloroform solution) of Compound (3) was measured in the same manner as in Example 1, as a result, the peak wavelength was 514 nm and the molar extinction coefficient at this wavelength was 40,000 $M^{-1}$ $cm^{-1}$.

<Fabrication of Photoelectric Conversion Device and Solid-State Imaging Device>

A solid-state imaging device including a photoelectric conversion device was fabricated in the same manner as in Example 1 except for changing Compound (1) in the photoelectric conversion layer to Compound (3).

Example 4

<Synthesis of Compound (4)>

Compound (4) was synthesized in the same manner as in Example 2 except for changing benzoindandione to indandione.

<Identification of Compound (4)>

$^1$H NMR ($CDCl_3$) δ: 7.39-7.47 (8H, d), 7.59-7.67 (5H, m), 7.79-7.90 (7H, m), 8.03 (3H, m), 8.54 (1H, d), 8.94 (1H, s)

Molecular weight: 551.63

<Measurement of Melting Point>

The melting point of Compound (4) was measured in the same manner as in Example 1 and found to be 261° C.

<Measurement of Absorption Spectrum>

The absorption spectrum (in a chloroform solution) of Compound (4) was measured in the same manner as in Example 1, as a result, the peak wavelength was 517 nm and the molar extinction coefficient at this wavelength was 43,000 $M^{-1}$ $cm^{-1}$.

<Fabrication of Photoelectric Conversion Device and Solid-State Imaging Device>

A solid-state imaging device including a photoelectric conversion device was fabricated in the same manner as in Example 1 except for changing Compound (1) in the photoelectric conversion layer to Compound (4).

Example 5

<Synthesis of Compound (5)>

Compound (5b) and Compound (5) were synthesized in the same manner as in Example 3 except for changing N-phenyl-2-naphthylamine to N,N-bis(9,9-dimethyl-2-fluorenyl) amine (synthesized according to a known method).

<Identification of Compound (5b)>

$^1$H NMR ($CDCl_3$) δ: 1.42 (12H, s), 7.15-7.50 (12H, m), 7.58-7.70 (5H, m), 7.85 (2H, d), 8.23 (1H, s), 10.10 (1H, s).

<Identification of Compound (5)>

$^1$H NMR ($CDCl_3$) δ: 1.45 (12H, s), 7.18-7.49 (12H, d), 7.60 (2H, d), 7.64-7.72 (3H, m), 7.78-7.85 (2H, m), 7.87 (1H, d), 8.03 (3H, m), 8.54 (1H, d), 8.93 (1H, s).

Molecular weight: 683.83

<Measurement of Melting Point>

The melting point of Compound (5) was measured in the same manner as in Example 1 and found to be 270° C.

<Measurement of Absorption Spectrum>

The absorption spectrum (in a chloroform solution) of Compound (5) was measured in the same manner as in Example 1, as a result, the peak wavelength was 541 nm and the molar extinction coefficient at this wavelength was 40,000 $M^{-1}$ $cm^{-1}$.

<Fabrication of Photoelectric Conversion Device and Solid-State Imaging Device>

A solid-state imaging device including a photoelectric conversion device was fabricated in the same manner as in Example 1 except for changing Compound (1) in the photoelectric conversion layer to Compound (5).

Example 6

<Synthesis of Compound (6)>

Compound (6b) and Compound (6) were synthesized in the same manner as in Example 1 except for changing N-phenyl-2-naphthylamine to 1,2'-dinaphthylamine (produced by Tokyo Chemical Industry Co., Ltd.).

<Identification of Compound (6b)>

$^1$H NMR ($CDCl_3$) δ: 7.13-7.29 (3H, m), 7.31-7.60 (9H, m), 7.76-7.85 (4H, m), 7.88 (1H, d), 7.93-7.99 (2H, m), 8.20 (1H, s), 10.07 (1H, s).

<Identification of Compound (6)>

$^1$H NMR ($CDCl_3$) δ: 7.23-7.63 (12H, m), 7.67-7.75 (2H m), 7.80 (2H, d), 7.85 (1H, d), 7.90 (1H, d), 7.96 (1H, d), 7.99 (1H, d), 8.09-8.14 (3H, m), 8.51 (2H, d), 8.57 (1H, d), 9.00 (1H, s).

Molecular weight: 601.69

<Measurement of Melting Point>

The melting point of Compound (6) was measured in the same manner as in Example 1 and found to be 300° C.

<Measurement of Absorption Spectrum>

The absorption spectrum (in a chloroform solution) of Compound (6) was measured in the same manner as in Example 1, as a result, the peak wavelength was 539 nm and the molar extinction coefficient at this wavelength was 50,000 $M^{-1}$ $cm^{-1}$.

<Fabrication of Photoelectric Conversion Device and Solid-State Imaging Device>

A solid-state imaging device including a photoelectric conversion device was fabricated in the same manner as in Example 1 except for changing Compound (1) in the photoelectric conversion layer to Compound (6).

Example 7

<Synthesis of Compound (7)>

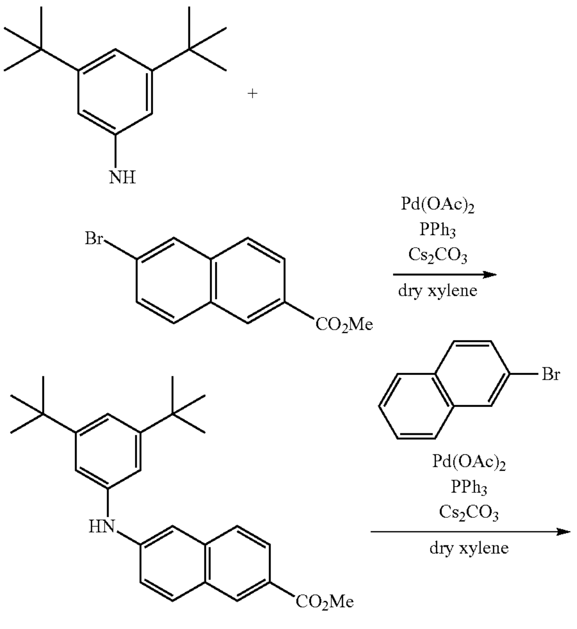

11a'

-continued

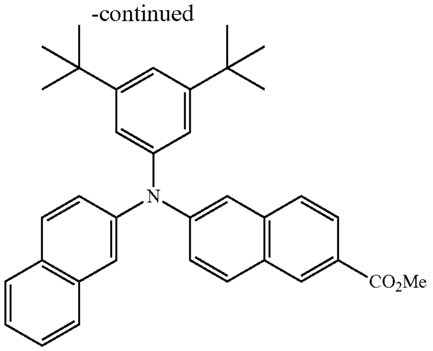

11a (Synthesis of Compound 7a')

To 40 ml of dehydrated xylene, 3.0 g of 3,5-di-tert-butylaniline (produced by Tokyo Chemical Industry Co., Ltd.), 3.5 g of methyl 6-bromo-2-naphthoate (produced by Wako Pure Chemical Industries, Ltd.), 90 mg of palladium acetate, 420 mg of triphenylphosphine and 8.7 g of cesium carbonate were added, followed by refluxing for 5 hours. The reaction mixture was suction-filtered and after distilling off the solvent by an evaporator, the residue was purified on a silica gel column (developing solvent: toluene). The solvent was distilled off to obtain 2.2 g of Compound (7a').

(Synthesis of Compound 7a)

To 20 ml of dehydrated xylene, 1.4 g of 2-bromonaphthalene (produced by Tokyo Chemical Industry Co., Ltd.), 2.2 g of Compound (7a'), 60 mg of palladium acetate, 300 mg of triphenylphosphine and 3.7 g of cesium carbonate were added, followed by refluxing for 5 hours. The reaction mixture was suction-filtered and after distilling off the solvent by an evaporator, the residue was purified on a silica gel column (developing solvent: toluene). The solvent was distilled off to obtain 2.4 g of Compound (7a).

The subsequent procedure was performed in the same manner as in Example 1 except for changing Compound (1a) to Compound (7a), whereby Compound (7) was synthesized.

<Identification of Compound (7)>

$^1$H NMR ($CDCl_3$) δ: 1.27 (18H, s), 7.09 (2H, d), 7.25-7.28 (1H, m), 7.35-7.47 (5H, m), 7.59-7.63 (2H, m), 7.67-7.73 (3H, m), 7.80-7.88 (3H, m), 8.11 (3H, m), 8.51 (2H, m), 8.59 (1H, d), 9.02 (1H, s).

Molecular weight: 663.84

<Measurement of Melting Point>

The melting point of Compound (7) was measured in the same manner as in Example 1 and found to be 299° C.

<Measurement of Absorption Spectrum>

The absorption spectrum (in a chloroform solution) of Compound (7) was measured in the same manner as in Example 1, as a result, the peak wavelength was 559 nm and the molar extinction coefficient at this wavelength was 51,000 $M^{-1}$ $cm^{-1}$.

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (7).

Example 8

<Synthesis of Compound (8)>

Compound (8) was synthesized in the same manner as in Example 1 except for changing N-phenyl-2-naphthylamine to N-phenyl-2-pyridylamine (synthesized by the method described in *J. Am. Chem. Soc.,* 2008, 130, 6586).

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (8).

Example 9

<Synthesis of Compound (9)>

Compound (9) was synthesized in the same manner as in Example 1 except for changing methyl 6-bromo-2-naphthoate to ethyl 6-bromo-4-benzyloxy-2-naphthoate (synthesized by the method described in *Chem. Eur. J.,* 2008, 14, 2811).

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (9).

Example 10

<Synthesis of Compound (10)>

Compound (10) was synthesized in the same manner as in Example 3 except for changing N-phenyl-2-naphthylamine to p,p'-ditolylamine (produced by Tokyo Chemical Industry Co., Ltd.) and changing methyl 6-bromo-2-naphthoate to ethyl 7-bromo-2-pyrenecarboxylate (synthesized by the method described in *Org. Lett.,* 2006, 8, 5037).

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (10).

Example 11

<Synthesis of Compound (11)>

Compound (11) was synthesized in the same manner as in Example 1 except for changing benzoindandione (1H-cyclopenta[b]naphthalene-1,3(2H)-dione) to 4,9-diphenyl-1H-cyclopenta[b]naphthalene-1,3(2H)-dione (synthesized by the method described in *J. Chem. Soc.*, Perkin Trans., 1, 1983, 2, 459).

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (11).

Example 12

<Synthesis of Compound (12)>

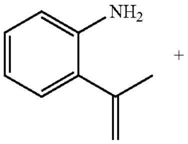

-continued

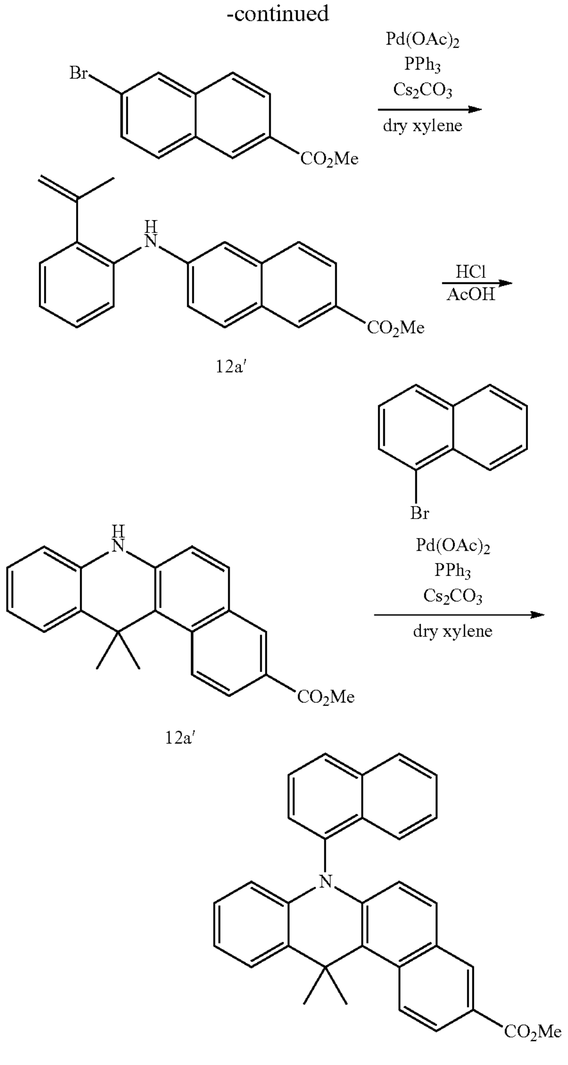

12a'

12a'

12a

<Synthesis of Compound 12a">

To 50 ml of dehydrated xylene, 4.2 g of 2-isopropenylaniline (produced by Aldrich Chemical Co. Inc.), 8.4 g of methyl 6-bromo-2-naphthoate (produced by Wako Pure Chemical Industries, Ltd.), 210 mg of palladium acetate, 740 mg of triphenylphosphine and 20.5 g of cesium carbonate were added, followed by refluxing for 4 hours. The reaction mixture was suction-filtered and after distilling off the solvent by an evaporator, the residue was purified on a silica gel column (developing solvent: toluene). The solvent was distilled off to obtain 7.8 g of Compound (12a").

(Synthesis of Compound 12a')

To 50 ml of acetic acid, 7.3 g of Compound (12a") and 10 ml of concentrated hydrochloric acid were added, followed by stirring under hating at 60° C. for 20 minutes. The reaction mixture was cooled to room temperature and after adding 200 ml of water, the precipitated solid was suction-filtered to obtain 6.0 g of Compound (12a')

(Synthesis of Compound 12a)

To 20 ml of dehydrated xylene, 1.0 g of 1-bromonaphthalene (produced by Tokyo Chemical Industry Co., Ltd.), 1.0 g of Compound (12a'), 150 mg of palladium acetate, 500 mg of triphenylphosphine and 2.1 g of cesium carbonate were added, followed by refluxing for 6 hours. The reaction mixture was suction-filtered and after distilling off the solvent by an evaporator, the residue was purified on a silica gel column (developing solvent: toluene). The solvent was distilled off to obtain 1.4 g of Compound (12a).

The subsequent procedure was performed in the same manner as in Example 1 except for changing Compound (1a) to Compound (12a), whereby Compound (12) was synthesized.

<Identification of Compound (12)>

$^1$H NMR ($CDCl_3$) δ: 2.40 (6H, d), 5.90 (1H, d), 6.46 (1H, d), 6.79 (1H, t), 6.95 (1H, t), 7.39-7.48 (2H, m), 7.52-7.60 (3H, m), 7.67-7.80 (4H, m), 8.00-8.15 (5H, m), 8.50 (2H, s), 8.61 (1H, d), 8.75 (2H, m).

Molecular weight: 591.70

<Measurement of Melting Point>

The melting point of Compound (12) was measured in the same manner as in Example 1 and found to be 350° C. or more.

<Measurement of Absorption Spectrum>

The absorption spectrum (in a chloroform solution) of Compound (12) was measured in the same manner as in Example 1, as a result, the peak wavelength was 560 nm and the molar extinction coefficient at this wavelength was 48,000 $M^{-1}$ $cm^{-1}$.

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (12).

Example 13

<Synthesis of Compound (13)>

Compound (13) was synthesized in the same manner as in Example 12 except for changing 1-bromonaphthalene to 2-bromonaphthalene (produced by Tokyo Chemical Industry Co., Ltd.).

<Identification of Compound (13)>

$^1$H NMR ($CDCl_3$) δ: 2.48 (6H, s), 6.22 (1H, d), 6.56 (1H, d), 7.28-7.38 (1H, m), 7.35-7.47 (2H, m), 7.49 (1H, t), 7.59-7.72 (5H, m), 7.86-7.98 (4H, m), 8.03 (1H, d), 8.09 (2H, m), 8.19 (1H, d), 8.47 (2H, d), 8.56 (1H, d), 9.31 (1H, s).

Molecular weight: 591.70

<Measurement of Melting Point>

The melting point of Compound (13) was measured in the same manner as in Example 1 and found to be 303° C.

<Measurement of Absorption Spectrum>

The absorption spectrum (in a chloroform solution) of Compound (13) was measured in the same manner as in Example 1, as a result, the peak wavelength was 563 nm and the molar extinction coefficient at this wavelength was 50,000 $M^{-1}$ $cm^{-1}$.

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (13).

Example 14

<Synthesis of Compound (14)>

Compound (14) was synthesized in the same manner as in Example 12 except for changing 1-bromonaphthalene to 1-bromo-4-tert-butylbenzene (produced by Tokyo Chemical Industry Co., Ltd.).

<Identification of Compound (14)>

$^1H$ NMR ($CDCl_3$) δ: 1.46 (9H, s), 2.30 (6H, s), 6.10 (1H, d), 6.55 (1H, d), 6.93 (2H, m), 7.21 (2H, d), 7.48 (1H, d), 7.54 (1H, d), 7.62-7.77 (4H, m), 8.04-8.15 (3H, m), 8.50 (2H, s), 8.56 (1H, d), 8.70 (1H, d), 8.79 (1H, s).

Molecular weight: 597.74

<Measurement of Melting Point>

The melting point of Compound (14) was measured in the same manner as in Example 1 and found to be 335° C.

<Measurement of Absorption Spectrum>

The absorption spectrum (in a chloroform solution) of Compound (14) was measured in the same manner as in Example 1, as a result, the peak wavelength was 568 nm and the molar extinction coefficient at this wavelength was 53,000 $M^{-1}$ $cm^{-1}$.

<Fabrication of Photoelectric Conversion Device and Solid-State Imaging Device>

A solid-state imaging device containing a photoelectric conversion device was fabricated in the same manner as in Example 1 except for changing Compound (1) in the photoelectric conversion layer to Compound (14).

Example 15

A solid-state imaging device containing a photoelectric conversion device was fabricated in the same manner as in Example 6 except for changing the ratio of Compound (6) and fullerene ($C_{60}$) in the photoelectric conversion layer to become a ratio of 200 nm and 200 nm each in terms of a single layer.

Example 16

A solid-state imaging device containing a photoelectric conversion device was fabricated in the same manner as in Example 6 except for changing the ratio of Compound (6) and fullerene ($C_{60}$) in the photoelectric conversion layer to become a ratio of 267 nm and 133 nm each in terms of a single layer.

Example 17

A solid-state imaging device containing a photoelectric conversion device was fabricated in the same manner as in Example 6 except for changing fullerene ($C_{60}$) in the photoelectric conversion layer to fullerene ($C_{70}$).

Example 18

A solid-state imaging device containing a photoelectric conversion device was fabricated in the same manner as in Example 1 except for changing EB-3 in the electron blocking layer to EB-4.

Reference Examples 1 to 4

Solid-state imaging devices containing a photoelectric conversion device were fabricated in the same manner as in Example 1 except for changing Compound (1) in the photoelectric conversion layer to the compound shown in the Table below (Compounds (15) to (18)).

Example 19

A solid-state imaging device containing a photoelectric conversion device was fabricated in the same manner as in Example 1 except for depositing Compound (1) alone to a thickness of 100 nm to form the photoelectric conversion layer.

Examples 20 to 25

Solid-state imaging devices containing a photoelectric conversion device were fabricated in the same manner as in Example 19 except for changing Compound (1) in the photoelectric conversion layer to the compound shown in the Table below (Compounds (2) to (7)).

Comparative Examples 1 to 2

Solid-state imaging devices including a photoelectric conversion device were fabricated in the same manner as in Example 1 except for changing Compound (1) in the photoelectric conversion layer to each of the compounds shown in the Table below (Compounds (19) to (20)).

Comparative Example 3

A solid-state imaging device containing a photoelectric conversion device was fabricated in the same manner as in Example 18 except for changing Compound (1) in the photoelectric conversion layer to Compound (19).

Comparative Examples 4 to 5

Solid-state imaging devices including a photoelectric conversion device were fabricated in the same manner as in Comparative Examples 1 to 2 except for forming the photoelectric conversion layer by depositing each of Compounds (19) to (20) alone to a thickness of 100 nm Compounds used above are shown below.

EB-3

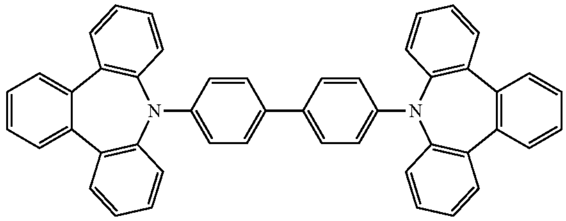

EB-4

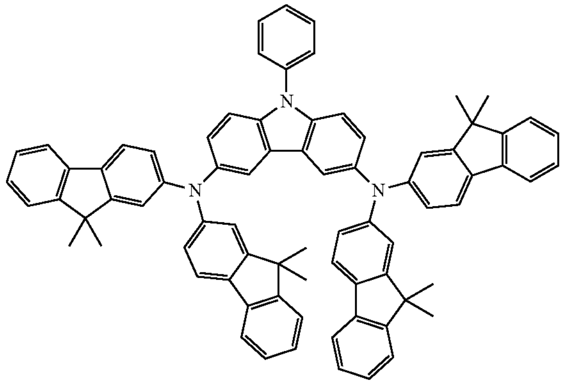

-continued
Compound (1)
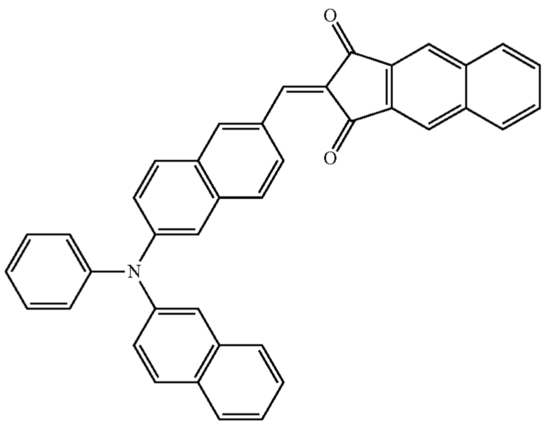
Compound (2)
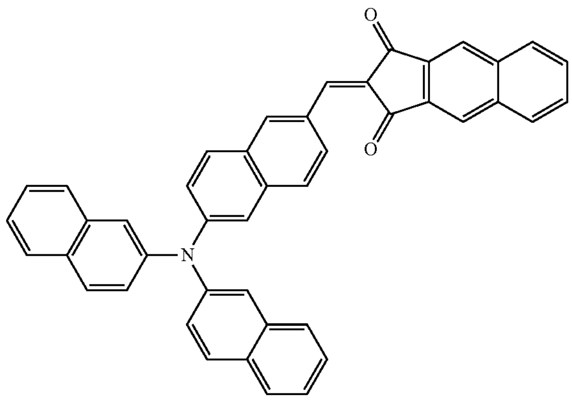
Compound (3)
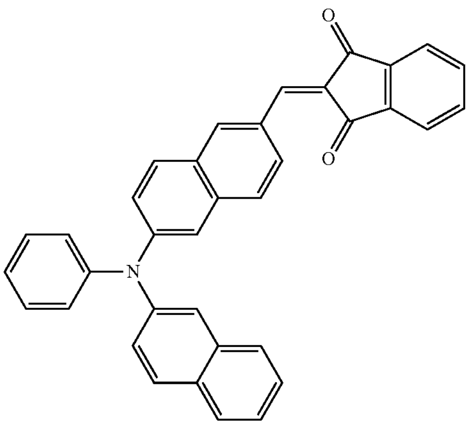
-continued
Compound (4)
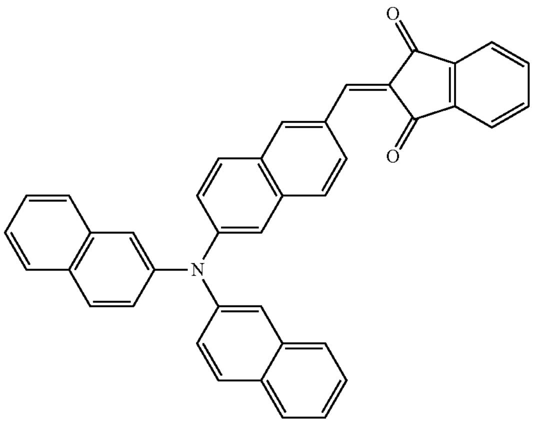
Compound (5)
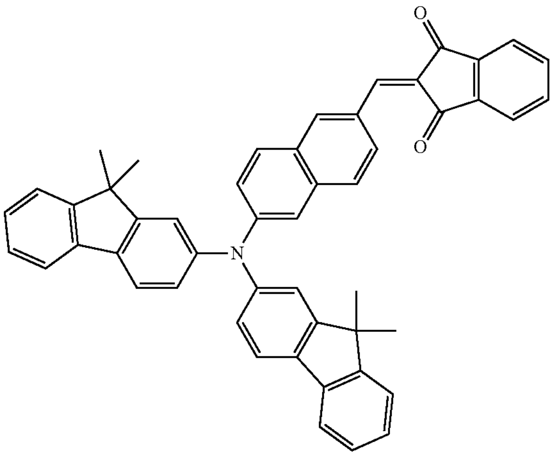
Compound (6)
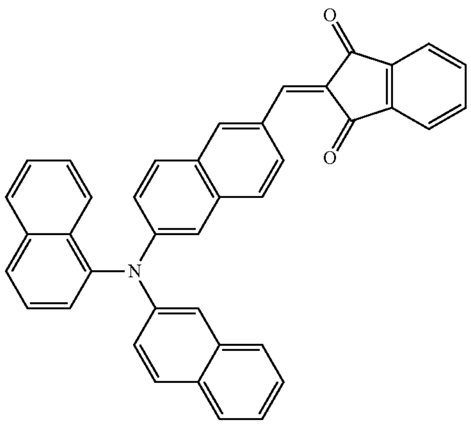

-continued
Compound (7)
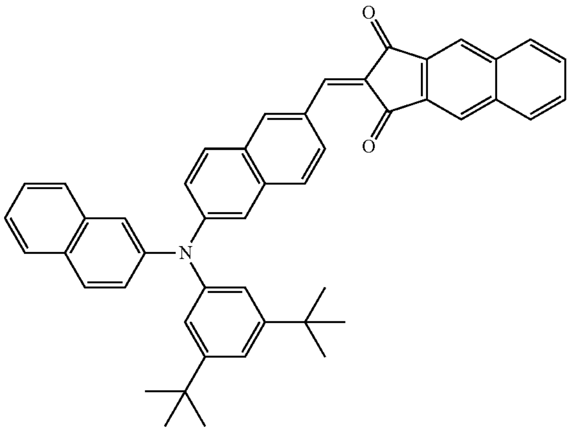
Compound (8)
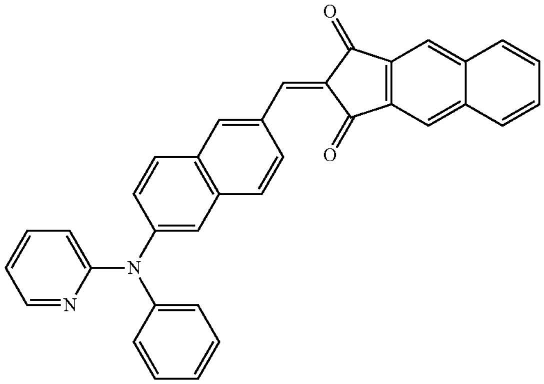
Compound (9)
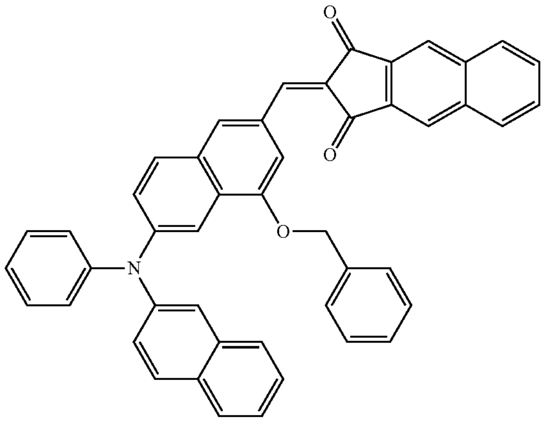
-continued
Compound (10)
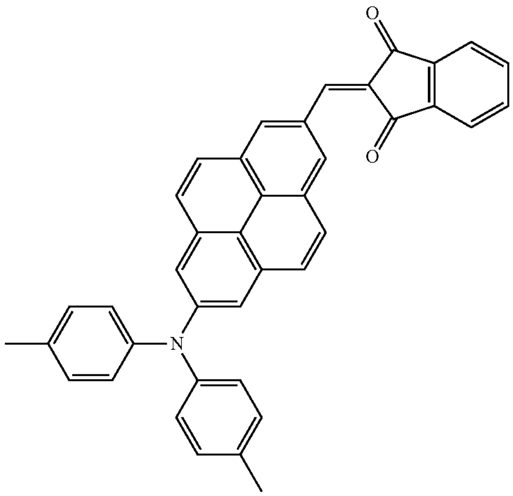
Compound (11)
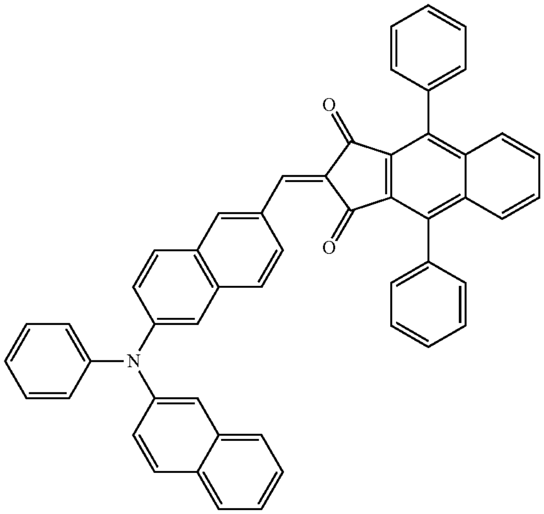
Compound (12)
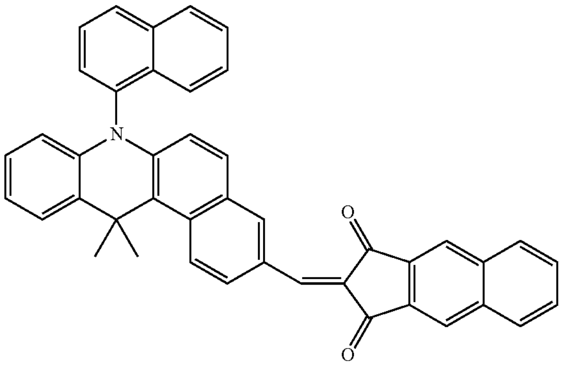

-continued
Compound (13)
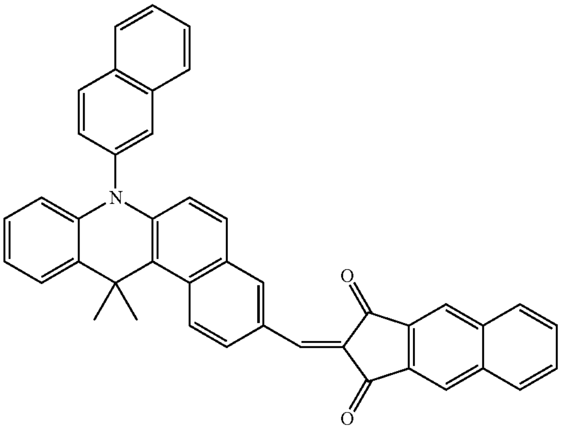
Compound (14)
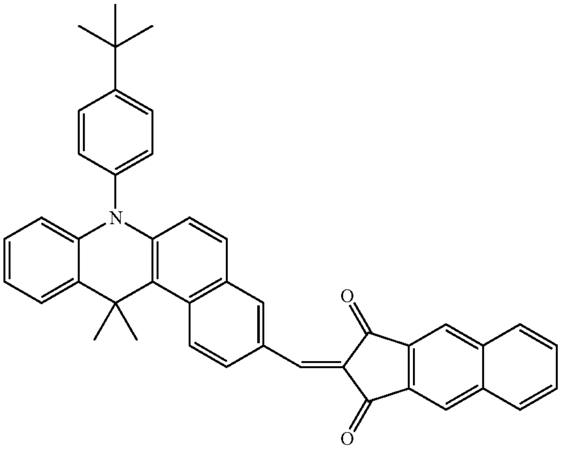
Compound (15)
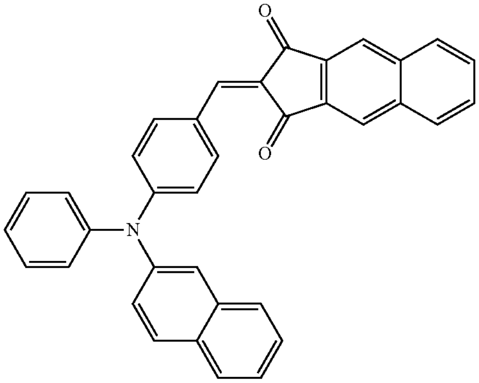
-continued
Compound (16)
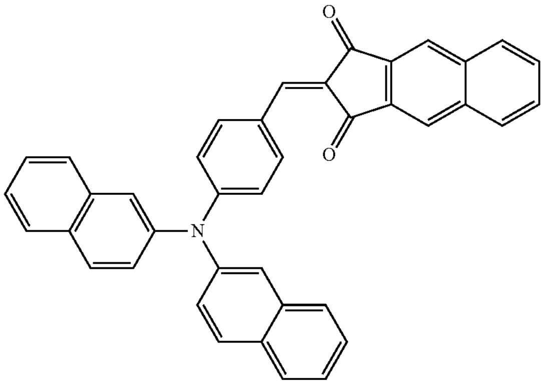
Compound (17)
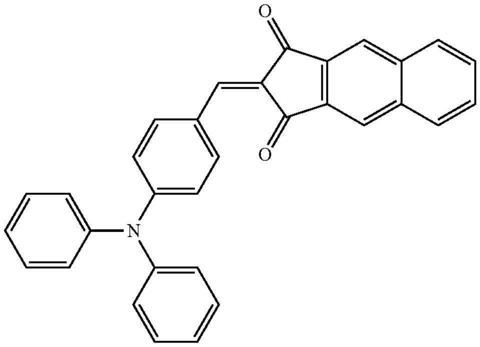
Compound (18)
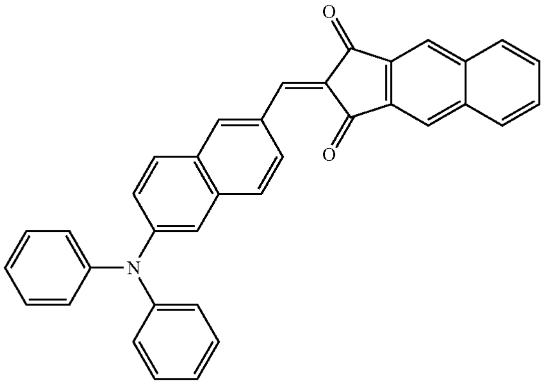
Compound (19)
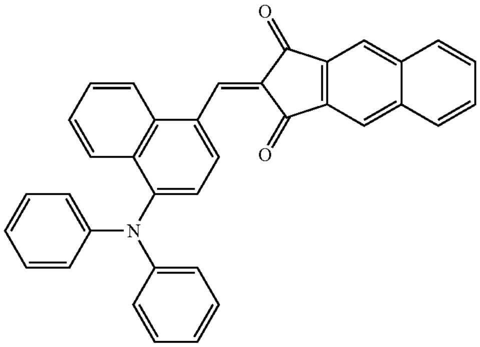

-continued

Compound (20)

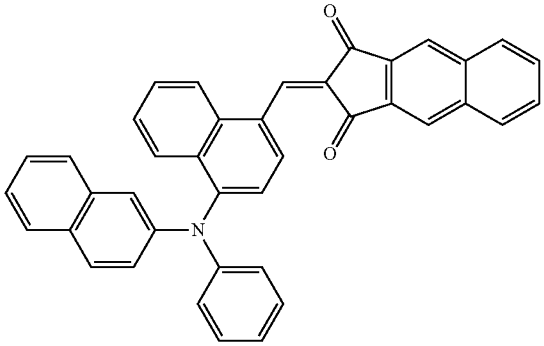

[Evaluation 1]

With respect to the solid-state imaging devices of Examples 1 to 18, Reference Examples 1 to 4 and Comparative Examples 1 to 3, the solid-state imaging device was aged on a hot plate heated to 190° C. for 30 minutes in the case of using EB-3 for the electron blocking layer or aged on a hot plate heated to 200° C. for 30 minutes in the case of using EB-4 for the electron blocking layer, the dark current was measured before and after the aging, and the heat resistance was rated C when the dark current after aging was increased to 10 times or more that before aging (room temperature of 20° C.), rated B when the dark current was increased to more than 1 times to less than 10 times, and rated A when the dark current was not changed (1 times) or the increase was not more than that. The external quantum efficiency (a relative value by taking that of Reference Example 4 as 100) at a maximum sensitivity wavelength when an electric field of $2\times10^5$ V/cm was applied to the photoelectric conversion device, and the relative response speed (the rising time (a relative value by taking that of Reference Example 4 as 1) from 0% to 98% in terms of the signal strength), in each of the solid-state imaging devices of Examples 1 to 18, Reference Examples 1 to 4 and Comparative Examples 1 to 3 are shown in the Table. Incidentally, in measuring the photoelectric conversion performance of each device, light was entered from the upper electrode (transparent electrically conductive film) side.

The evaluation results are shown in Table 1 below.

TABLE 1

| | Compound Used for Photoelectric Conversion Material | Compound Used for Electron Blocking Layer | Heat Resistance of Solid-State Imaging Device | External Quantum Efficiency at Maximum Sensitivity Wavelength (relative value) | Rising Time From 0% to 98% in Terms of Signal Strength (relative value) |
|---|---|---|---|---|---|
| Example 1 | Compound (1), $C_{60}$ | EB-3 | A | 101 | 2 |
| Example 2 | Compound (2), $C_{60}$ | EB-3 | A | 98 | 2 |
| Example 3 | Compound (3), $C_{60}$ | EB-3 | A | 96 | 1 |
| Example 4 | Compound (4), $C_{60}$ | EB-3 | A | 96 | 1.5 |
| Example 5 | Compound (5), $C_{60}$ | EB-3 | A | 120 | 1 |
| Example 6 | Compound (6), $C_{60}$ | EB-3 | A | 100 | 2 |
| Example 7 | Compound (7), $C_{60}$ | EB-3 | A | 110 | 2 |
| Example 8 | Compound (8), $C_{60}$ | EB-3 | A | 95 | 2.5 |
| Example 9 | Compound (9), $C_{60}$ | EB-3 | A | 93 | 3 |
| Example 10 | Compound (10), $C_{60}$ | EB-3 | A | 93 | 3.3 |
| Example 11 | Compound (11), $C_{60}$ | EB-3 | A | 92 | 2.7 |
| Example 12 | Compound (12), $C_{60}$ | EB-3 | A | 118 | 1.5 |
| Example 13 | Compound (13), $C_{60}$ | EB-3 | A | 115 | 2 |
| Example 14 | Compound (14), $C_{60}$ | EB-3 | A | 118 | 2 |
| Example 15 | Compound (6), $C_{60}$ | EB-3 | A | 100 | 2 |
| Example 16 | Compound (6), $C_{60}$ | EB-3 | A | 95 | 3 |
| Example 17 | Compound (6), $C_{70}$ | EB-3 | A | 100 | 2 |
| Example 18 | Compound (6), $C_{60}$ | EB-4 | A | 101 | 2 |
| Reference 1 | Compound (15), $C_{60}$ | EB-3 | B | 100 | 8 |
| Reference 2 | Compound (16), $C_{60}$ | EB-3 | B | 95 | 100 |
| Reference 3 | Compound (17), $C_{60}$ | EB-3 | B | 100 | 1 |
| Reference 4 | Compound (18), $C_{60}$ | EB-3 | B | 100 | 1 |
| Comparative Example 1 | Compound (19), $C_{60}$ | EB-3 | C | 40 | 1200 |
| Comparative Example 2 | Compound (20), $C_{60}$ | EB-3 | C | 45 | 1400 |
| Comparative Example 3 | Compound (19), $C_{60}$ | EB-4 | C | 40 | 1200 |

Also, the emission quantum efficiency of the co-deposited film of fullerene and each of Compounds (1) to (14) in Examples 1 to 18 was measured using SPEX Fluorolog-3 manufactured by HORIBA Jobin Yvon.

When the emission quantum efficiency of the co-deposited film of $C_{60}$ or $C_{70}$ and each of Compounds (1) to (14) was measured, the emission quantum efficiency was 0.1% or less in all cases, revealing that the co-deposited film is a non-luminescent film.

[Evaluation 2]

With respect to the solid-state imaging devices of Examples 19 to 25 and Comparative Examples 4 and 5, the solid-state imaging device was aged on a hot plate heated to 130° C. for 30 minutes, the dark current was measured before and after the aging, and the heat resistance was rated B when the dark current after aging was increased to 15 times or more that before aging (room temperature of 20° C.), and rated A when the dark current was not changed (1 times) or the increase was less than 15 times.

The external quantum efficiency (a relative value by taking that of Example 19 as 100) at a maximum sensitivity wavelength when an electric field of $2\times10^5$ V/cm was applied to the photoelectric conversion device, and the relative response speed (the rising time (a relative value by taking that of Example 19 as 1) from 0% to 98% in terms of the signal strength), in each of the solid-state imaging devices of Examples 19 to 25 and Comparative Examples 4 and 5 are shown in the Table. Incidentally, in measuring the photoelectric conversion performance of each device, light was entered from the upper electrode (transparent electrically conductive film) side.

The evaluation results are shown in Table 2 below.

TABLE 2

| | Compound Used for Photoelectric Conversion Material | Compound Used for Electron Blocking Layer | Heat Resistance of Solid-State Imaging Device | External Quantum Efficiency at Maximum Sensitivity Wavelength (relative value) | Rising Time From 0% to 98% in Terms of Signal Strength (relative value) |
|---|---|---|---|---|---|
| Example 19 | Compound (1) | EB-3 | A | 100 | 1 |
| Example 20 | Compound (2) | EB-3 | A | 104 | 1 |
| Example 21 | Compound (3) | EB-3 | A | 79 | 1.3 |
| Example 22 | Compound (4) | EB-3 | A | 79 | 1.6 |
| Example 23 | Compound (5) | EB-3 | A | 78 | 1.3 |
| Example 24 | Compound (6) | EB-3 | A | 96 | 1 |
| Example 25 | Compound (7) | EB-3 | A | 100 | 1 |
| Comparative Example 4 | Compound (19) | EB-3 | B | 26 | 3 |
| Comparative Example 5 | Compound (20) | EB-3 | B | 33 | 3.7 |

It is seen from Tables 1 and 2 that the imaging device of the present invention can make the imaging at a high response speed and a high S/N and also, is excellent in the heat resistance by using a compound in which a substituted amino group and a methine group are connected with a naphthylene group at the 2-position and 6-position as connection sites.

In the fabrication of a photoelectric conversion device, when three devices were fabricated using each of Compounds (1) to (14), the photoelectric conversion devices using each of the compounds exhibited a substantially equivalent performance. On the other hand, when photoelectric conversion devices were fabricated in the same manner except for changing the compound to each of Compounds (19) to (20), the photoelectric conversion performance was extremely low. In view of this fact, by using a compound in which a substituted amino group and a methine group are connected with a naphthylene group at the 2-position and 6-position as connection sites, the yield exhibits a value substantially close to 100%, and good results can be obtained in the productivity.

The entire disclosure of Japanese Patent Application No. 2009-207230 filed on Sep. 8, 2009, and Japanese Patent Application No. 2010-065204 filed on Mar. 19, 2010, from which the benefit of foreign priority has been claimed in the present application, and the entire disclosure of Japanese Patent Application No. 2010-200508 filed on Sep. 8, 2010 are incorporated herein by reference, as if fully set forth.

What is claimed is:

1. A compound represented by the following formula (II):

Formula (II):

(II)

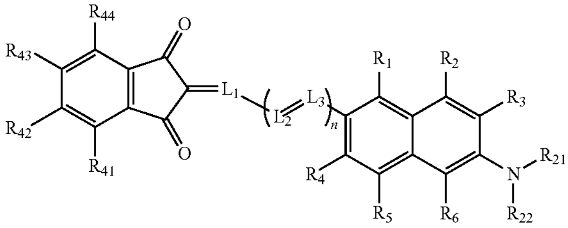

wherein each of $L_1$, $L_2$ and $L_3$ independently represents an unsubstituted methine group or a substituted methine group, n represents an integer of 0 or more, each of $R_1$, $R_2$, $R_3$, $R_4$, $R_5$ and $R_6$ independently represents a hydrogen atom or a substituent, $R_1$ and $R_2$, $R_2$ and $R_3$, $R_4$ and $R_5$, and $R_6$ may be combined with each other to form a ring, each of $R_{21}$ and $R_{22}$ independently represents a substituted aryl group, an unsubstituted aryl group, a substituted heteroaryl group or an unsubstituted heteroaryl group, provided that the case where both $R_{21}$ and $R_{22}$ are an unsubstituted phenyl group is excluded, and each of $R_{41}$, $R_{42}$, $R_{43}$ and $R_{44}$ independently represents a hydrogen atom or a substituent.

2. The compound according to claim 1, wherein each of $R_{43}$ to $R_{44}$ in formula (II) independently is a hydrogen atom, a halogen atom, an alkyl group, an aryl group, a heterocyclic group, an alkoxy group, an aryloxy group, an amino group, an alkylthio group, an alkenyl group or a cyano group.

3. The compound according to claim 1, wherein each of $R_1$ to $R_6$ in formula (II) independently is a hydrogen atom, an alkyl group, an aryl group, a heterocyclic group, an alkoxy group or an aryloxy group.

4. The compound according to claim 1, wherein in formula (II), each of $L_1$, $L_2$ and $L_3$ is an unsubstituted methine group.

5. The compound according to claim 1, wherein in formula (II), n is 0.

6. A photoelectric conversion material containing the compound according to claim 1.

7. A film containing the compound according to claim 1.

8. The film according to claim 7, which further comprises an n-type organic semiconductor.

9. The film according to claim 8, wherein the film is a non-luminescent film.

10. A photoelectric conversion device comprising an electrically conductive film, an organic photoelectric conversion film, and a transparent electrically conductive film, wherein the organic photoelectric conversion film contains the compound according to claim 1.

11. The photoelectric conversion device according to claim 10, wherein the organic photoelectric conversion film contains an n-type organic semiconductor.

12. The photoelectric conversion device according to claim 11, wherein the organic photoelectric conversion film is a non-luminescent film.

13. The photoelectric conversion device according to claim 11, wherein the n-type organic semiconductor is a fullerene or a fullerene derivative.

14. The photoelectric conversion device according to claim 13, wherein the fullerene is $C_{60}$.

15. The photoelectric conversion device according to claim 13, wherein the organic photoelectric conversion film has a bulk heterojunction structure formed by mixing the compound according to claim 1 and the fullerene or fullerene derivative.

16. The photoelectric conversion device according to claim 13, wherein the volume ratio of the fullerene or fullerene derivative to the compound represented by formula (II) according to claim 1, which are contained in the organic photoelectric conversion film, is 50% or more.

17. The photoelectric conversion device according to claim 10, wherein the photoelectric conversion device is fabricated by stacking the electrically conductive film, the organic photoelectric conversion film and said transparent electrically conductive film in this order.

18. The photoelectric conversion device according to claim 17, wherein the organic photoelectric conversion film is deposited by a vacuum deposition method.

19. The photoelectric conversion device according to claim 10, wherein light is incident on the organic photoelectric conversion film through the transparent electrically conductive film.

20. The photoelectric conversion device according to claim 10, wherein the transparent electrically conductive film comprises a transparent electrically conductive metal oxide.

21. The photoelectric conversion device according to claim 10, wherein the transparent electrically conductive film is formed directly on the organic photoelectric conversion film.

22. The photoelectric conversion device according to claim 10, which further comprises a charge blocking layer.

23. The photoelectric conversion device according to claim 10, wherein the absorption spectrum in a chloroform solution of the compound represented by formula (II) has a molar extinction coefficient of 30,000 $M^{-1}$ $cm^{-1}$ or more in the visible region at a wavelength of 400 to 700 nm.

24. A method of using the photoelectric conversion device according to claim 10, with the electrically conductive film and the transparent electrically conductive film defining a pair of electrodes, comprising a step of applying an electric field of $1\times10^{-4}$ to $1\times10^{7}$ V/cm between the pair of electrodes.

25. A method for producing the photoelectric conversion device according to claim 17, comprising a step of co-depositing the compound represented by formula (II) and a fullerene or fullerene derivative by vacuum heating deposition.

26. A photosensor comprising the photoelectric conversion device according to claim 10.

27. An imaging device containing the photoelectric conversion device according to claim 10.

* * * * *